US007902110B2

(12) United States Patent
Shimizu et al.

(10) Patent No.: US 7,902,110 B2
(45) Date of Patent: Mar. 8, 2011

(54) HOMOGENEOUS ASYMMETRIC HYDROGENATION CATALYST

(75) Inventors: Hideo Shimizu, Hiratsuka (JP); Daisuke Igarashi, Hiratsuka (JP); Wataru Kuriyama, Hiratsuka (JP); Yukinori Yusa, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 336 days.

(21) Appl. No.: 11/988,216

(22) PCT Filed: Jul. 6, 2006

(86) PCT No.: PCT/JP2006/313510
§ 371 (c)(1),
(2), (4) Date: Jan. 3, 2008

(87) PCT Pub. No.: WO2007/007646
PCT Pub. Date: Jan. 18, 2007

(65) Prior Publication Data
US 2009/0203927 A1    Aug. 13, 2009

(30) Foreign Application Priority Data
Jul. 7, 2005    (JP) .............................. 2005-199463

(51) Int. Cl.
*B01J 31/00* (2006.01)
(52) U.S. Cl. ...................... 502/152; 502/155
(58) Field of Classification Search ................. 502/152, 502/155
See application file for complete search history.

(56) References Cited

U.S. PATENT DOCUMENTS

| | | | |
|---|---|---|---|
| 3,732,329 A | 5/1973 | Thatcher et al. | |
| 4,120,870 A | 10/1978 | Townsend et al. | |
| 4,187,241 A * | 2/1980 | Townsend et al. | ............. 556/23 |

FOREIGN PATENT DOCUMENTS

| | | |
|---|---|---|
| EP | 0 771 812 | 5/1997 |
| EP | 0997470 A1 | 5/2000 |
| EP | 1 419 815 | 5/2004 |
| JP | 54-39052 | 3/1979 |
| JP | 9-124669 | 5/1997 |
| JP | 2004-161645 | 6/2004 |
| JP | 2005-41847 | 2/2005 |

| | | |
|---|---|---|
| WO | 01/19761 | 3/2001 |

OTHER PUBLICATIONS

International Search Report issued Oct. 10, 2006 in the International (PCT) Application of which the present application in the U.S. National Stage.
E. I. Klabunovskii et al., "Enantioselective Hydrogenation on Heterogeneous Metal Catalysts", React. Kinet. Catal. Lett., vol. 9, No. 1, pp. 73-77, 1978.
J. M. Townsend et al., "Novel Copper Complexes of Chiral Diphosphines: Preparation, Structure, and Use to Form Rhodium Complex Catalysts for Chiral Hydrogenations", J. Org. Chem., vol. 45, pp. 2995-2999, 1980.
E. I. Klabunovskii et al., "Asymmetrical Hydrogenation of Acetoacetic Ester on a Modified Raney Copper Catalyst", Inst. Org. Khim. Im. Zelinskogo, Moscow, USSR. Kinetika I Kataliz., 1975, 16(4), 1081 and its STN CA Abstract.
Ferraris, D., et al., Diastereo- and Enantioselective Alkylation of α-Imino Esters with Enol Silanes Catalyzed by (R)-Tol-BINAP-CuCIO$_4$ •(MeCN)$_2$, J. Org. Chem., 1998, 63, 6090-6091, In English, and see European Search Report dated Jun. 12, 2009.
Le Floch, Pascal., et al., "Biphosphinine-copper(I) complexes: chelate vs. polymeric helical structures," Chemical Abstract Services, database accession No. 1996:673485, In English, and see European Search Report dated Aug. 3, 2009.
Lipshutz, B.H., et al., "Copper(I)-Catalyzed Asymmetric Hydrosilylations of Imines at Ambient Temperatures" Angew. Chem. Int. Ed., 2004, 43, 2228-2230, In English, and see European Search Report dated Jun. 12, 2009.
Lipshutz, B.H., et al., "Scavenging and Reclaiming Phosphines Associated with Group 10 Metal-Mediated Couplings," Organic Letters, 2004, 6:14, 2305-2308, In English, and see European Search Report dated Jun. 12, 2009.
Schmizu, H., et al., "A novel approach for investigating enantioselectivity in asymmetric hydrogenation," Tetrahedron: Asymmetry, Jul. 26, 2004, 15:14, 2169-2172, In English, and see European Search Report dated Aug. 3, 2009.
Walther, D., et al., "Metal Complexes with 2,3-Bis(diphenylphosphino)-1,4-diazadiene Ligands: Synthesis, Structures, and an Intramolecular Metal-Mediated [4+2] Cycloaddition Employing a Benzene Ring as a Dienophile," Inorganic Chem., 2003, 42:2, 625-632, In English, and see European Search Report dated Aug. 3, 2009.
Wu, J., et al., "A remarkably effective copper(II)-dipyridylphosphine catalyst system for the asymmetric hydrosilylation of ketones in air," PNAS, Mar. 8, 2005, 102"10, 3570-3575, In English, and see European Search Report dated Jun. 12, 2009.

* cited by examiner

*Primary Examiner* — Taylor Victor Oh
(74) *Attorney, Agent, or Firm* — Sughrue Mion, PLLC

(57) ABSTRACT

Provide that a useful catalyst for homogeneous hydrogenation, particularly a catalyst for homogeneous asymmetric hydrogenation for hydrogenation, particularly asymmetric hydrogenation, which is obtainable with comparative ease and is excellent in economically and workability, and a process for producing a hydrogenated compound of an unsaturated compound, particularly an optically active compound using said catalyst with a high yield and optical purity.

11 Claims, No Drawings

HOMOGENEOUS ASYMMETRIC HYDROGENATION CATALYST

This application is a U.S. national stage of International Application No. PCT/JP2006/313510 filed July 6, 2006.

BACKGROUND OF THE INVENTION

1. Field of the Invention

The present invention relates to a novel catalyst useful as homogeneous hydrogenation, in particular as homogeneous asymmetric hydrogenation and, in detail, a process for producing a hydrogenated compound of an unsaturated compound, in particularly, an optically active compound using said catalyst.

2. Related Art

Recently, synthesis methods using copper as a catalyst have been widely studied in the field of asymmetric synthesis.

For example, WO01/19761 describes the asymmetric hydrosilylation of α,β-unsaturated ester. The method described in WO01/19761, however, has such problems that a silyl ether form of the above-mentioned α,β-unsaturated ester need to form and is necessary for an acid or alkali treatment to obtain the objective compound, therefore the method becomes to complicate operation, and result in high costs because a silane waste is produced in an equivalent or more amount theoretically, further a silane compound as a reducing agent used in hydrosilylation is highly expensive as compared with hydrogen gas.

U.S. Pat. No. 3,732,329 describes the hydrogenation of olefins by using a complex obtained by reacting copper(I) chloride with a phosphorus compound. In this U.S. Pat. No. 3,732,329, however, the phosphorus compound allowed to react with copper(I) chloride is not a chiral compound and the resulting complex is not a chiral complex, and there is no description of a reaction of a chiral ligand with a copper compound. Accordingly, the hydrogenation of the olefins described in this U.S. Pat. No. 3,732,329 is not an asymmetric hydrogenation.

React. Kinet. Catal. Lett., Vol. 9, No. 1, 73 (1978). describes the asymmetric hydrogenation of ethyl acetoacetate and acetylacetone by using a complex obtained from Raney copper and an optically active amino acid. However, the asymmetric hydrogenation described in this literature is a heterogeneous system. Accordingly, the literature has such problems that the reaction solution does not become homogeneous and the method described in this literature becomes inferior workability because Raney copper is required careful handling etc. In the reaction described in this literature, the catalyst activity and the asymmetric yield in the reaction system are extremely low and do not reach a practical level.

JP-A-54-39052 and J. Org. Chem., 45, 2995 (1980). describe that a rhodium complex is obtained by reacting a specific bisphosphine ligand with a copper salt to produce achiral copper complex once, and then the resulting copper complex is reacted with a rhodium complex to carry out copper-rhodium metal exchange reaction. They also describe an asymmetric hydrogenation using the resulting rhodium complex in a homogeneous system. However, in the method described in JP-A-54-39052, there is no description of an asymmetric hydrogenation using the copper complex as a catalyst, and the copper complex is used for only isolation and formation of the phosphine ligand. The catalyst species described in JP-A-54-39052 and J. Org. Chem., 45, 2995 (1980) are rhodium/phosphine complexes obtained by the metal exchange reaction. They have such problems that the methods described therein must be synthesized the copper complex first, therefore said methods become to complicate operation, in addition because rhodium is very expensive, the methods are poor economical efficiency.

Inst. Org. Khim. im. Zelinskogo, Moscow, USSR. Kinetika Kataliz., 16(4), 1081 (1975). described an asymmetric hydrogenation using a Raney copper-ruthenium alloy and optically active tartaric acid in a heterogeneous system, and an asymmetric hydrogenation using Raney copper and optically active tartaric acid in a heterogeneous system. However, the literature has such problems that because the method described in this literature is a heterogeneous asymmetric hydrogenation, the reaction solution does not become homogeneous, and Raney copper is required careful handling, therefore becomes inferior workability, further because Ruthenium is used in addition to copper, the method is costly.

Thus there is no practical and economical asymmetric hydrogenation in a homogeneous system using a copper complex having a chiral ligand and using copper as the only transition metal participating in the asymmetric hydrogenation.

SUMMARY OF THE INVENTION

Problem to be Resolved by the Invention

The present invention was made in view of the circumstances mentioned above. An object of the present invention is to provide a useful catalyst for homogeneous hydrogenation, particularly a catalyst for homogeneous asymmetric hydrogenation for hydrogenation, particularly asymmetric hydrogenation, which is obtainable with comparative ease and is excellent in economically and workability. Another object of the present invention is to provide a process for producing a hydrogenated compound of an unsaturated compound, particularly an optically active compound using said catalyst with a high yield.

The present inventors have conducted extensive research to solve the above-mentioned problem. As a result, it has been found that a desired hydrogenated compound of an unsaturated compound, particularly an optically active compound thereof can be obtained by hydrogenation, particularly asymmetric hydrogenation of an unsaturated compound in a homogeneous system using a chiral ligand and copper as a catalyst with a good yield, high economically and workability, and the present invention was completed.

That is, the present invention provides the following (1) to (18):

(1) A catalyst for homogeneous hydrogenation, which comprises a chiral copper complex having a chiral ligand.

(2) The catalyst for homogeneous hydrogenation according to the above-mentioned (1), wherein the chiral copper complex is a copper complex obtained by reacting a chiral ligand with a copper compound.

(3) A catalyst for homogeneous hydrogenation, which comprises a mixture of a chiral ligand and a copper compound.

(4) The catalyst for homogeneous hydrogenation according to any one of the above-mentioned (1) to (3), wherein the chiral ligand is at least one member selected from the group consisting of a monodentate ligand, a bidentate ligand, a tridentate ligand and a tetradentate ligand.

(5) The catalyst for homogeneous hydrogenation according to any one of the above-mentioned (1) to (4), further comprising an additive.

(6) The catalyst for homogeneous hydrogenation according to any one of the above-mentioned (3) to (5), which comprises a copper compound, a phosphorus compound represented by the formula (41):

$$PR^{151}{}_3 \qquad (41)$$

wherein three $R^{151}$s are the same or different and represent a hydrogen atom, an optionally substituted hydrocarbon group, an optionally substituted heterocyclic group, an optionally substituted alkoxy group, an optionally substituted aryloxy group, an optionally substituted aralkyloxy group, an amino group or a substituted amino group; and an optically active diphosphine compound.

(7) The catalyst for homogeneous hydrogenation according to any one of the above-mentioned (3) to (5), which comprises a copper complex represented by the formula (51):

$$[CuL^3(PR^{201}{}_3)_{n31}]_{n32} \qquad (51)$$

wherein $L^3$ represents a ligand, three $R^{201}$s are the same or different and represent a hydrogen atom, an optionally substituted hydrocarbon group, an optionally substituted heterocyclic group, an optionally substituted alkoxy group, an optionally substituted aryloxy group, an optionally substituted aralkyloxy group, an amino group or a substituted amino group; and n31 and n32 independently represent a natural number; and an optically active diphosphine compound.

(8) The catalyst according to any one of the above-mentioned (1) to (7), wherein the catalyst for homogeneous hydrogenation is a catalyst for homogeneous asymmetric hydrogenation.

(9) A process for producing a hydrogenated compound of an unsaturated compound, which comprises subjecting an unsaturated compound to a homogeneous hydrogenation in the presence of the catalyst for homogeneous hydrogenation according to any one of the above-mentioned (1) to (8).

(10) The process according to the above-mentioned (9), wherein the unsaturated compound is a prochiral compound, the catalyst for homogeneous hydrogenation is a catalyst for homogeneous asymmetric hydrogenation, and the obtained hydrogenated compound of the unsaturated compound is an optically active compound.

(11) A homogeneous hydrogenation method comprising using the catalyst for homogeneous hydrogenation according to any one of the above-mentioned (1) to (7).

(12) A homogeneous asymmetric hydrogenation method comprising using the catalyst for homogeneous asymmetric hydrogenation according to the above-mentioned (8).

(13) A chiral copper complex represented by the formula (61):

$$[L^{11}L^{12}CuL^{13}]_{n35} \qquad (61)$$

wherein $L^{11}$ represents a bidentate optically active phosphorus compound; $L^{12}$ represents a phosphorus compound different from $L^{11}$; $L^{13}$ represents a ligand; and n35 represents a natural number.

(14) A catalyst for homogeneous hydrogenation, which comprises the chiral copper complex according to the above-mentioned (13).

(15) The catalyst according to the above-mentioned (14), wherein the catalyst for homogeneous hydrogenation is a catalyst for homogeneous asymmetric hydrogenation.

(16) A process for producing an optically active compound, which comprises subjecting a prochiral compound to a homogeneous asymmetric hydrogenation in the presence of the catalyst for homogeneous asymmetric hydrogenation according to the above-mentioned (15).

(17) A homogeneous hydrogenation method comprising using the catalyst for homogeneous hydrogenation according to the above-mentioned (14).

(18) A homogeneous asymmetric hydrogenation method comprising using the catalyst for homogeneous asymmetric hydrogenation according to the above-mentioned (15).

The present invention is to provide a novel catalyst for homogeneous hydrogenation, in particularly, a novel catalyst for homogeneous asymmetric hydrogenation, which is useful in carrying out hydrogenation, particularly asymmetric hydrogenation in the presence of hydrogen gas, and carrying out transfer hydrogenation, particular asymmetric transfer hydrogenation in the coexistence with a hydrogen donor. Various unsaturated compounds are carrying out by hydrogenation, particularly asymmetric hydrogenation in the presence of the catalyst in a homogenous system to give hydrogenated compounds of said unsaturated compounds, particularly optically active compounds thereof, which are useful as intermediates of medicines and agrochemicals, perfumes and the like, efficiently with a good optical purity, in addition improving workability and economical efficiency. Thus, the present invention gets good results in the above-mentioned effect.

DETAILED DESCRIPTION OF THE INVENTION

In the present invention, the term "ligand" means an atom and atomic group forming a complex with copper (Cu), in addition to an atom and atomic group capable of forming the complex with copper (Cu).

[1] Catalyst for Homogeneous Hydrogenation

The catalyst for homogeneous hydrogenation of the present invention contains achiral copper complex having a chiral ligand. In addition, the catalyst for homogeneous hydrogenation of the present invention contains a mixture of a chiral ligand and a copper compound.

Here, in the present invention, the term "homogeneous" means a state in which a catalyst for homogeneous hydrogenation having catalytic activity is substantially dissolved on the occasion of hydrogenation, and a state in which said catalyst is dissolved and can be dissolved in the solution. The state in which the catalyst is dissolved in a solution is that the catalyst for homogeneous hydrogenation is dissolved at the start of the hydrogenation. Also, the state in which the catalyst can be dissolved in a solution is that the catalyst for homogeneous hydrogenation can be dissolved at the start of the hydrogenation. The state, for example, includes that the used catalyst for homogeneous hydrogenation is dissolved by a rise in reaction temperature or a progress of the reaction, and a reaction condition such as a kind of the used unsaturated compound or a solvent and reaction temperature. The state further includes that, in the case that a boundary surface exists in the reaction system, the property of the reaction system hardly change in the boundary surface, and the state is homogeneous or almost homogeneous through the whole reaction. As described above, the term "homogeneous" used in the present invention is a state in which the chiral copper complex or the copper compound used as the catalyst for homogenous hydrogenation is substantially dissolved on the occasion of hydrogenation, and a state that a substrate (unsaturated compound) used in the homogeneous hydrogenation, an additive used as necessary, or the inactivated the catalyst for homogeneous hydrogenation may exist as a solid in the reaction system.

In the present invention, further, the hydrogenation using the catalyst for homogeneous hydrogenation is a hydrogenation in which only copper is involved as a transition metal. That is, the catalyst for homogeneous hydrogenation of the present invention is a catalyst in which a transition metal other than copper is not substantially contained, and copper is used as a sole transition metal.

[1-1] Chiral Copper Complex

The chiral copper complex used in the catalyst for homogeneous hydrogenation of the present invention is, as described above, a chiral copper complex having a chiral ligand and is capable of using any chiral copper complex having a chiral ligand, and it is preferable for a chiral copper complex obtained by reacting a chiral ligand with a copper compound to use. Here, "the chiral copper complex obtained by reacting" includes a chiral copper complex which is reacted a chiral ligand and a copper compound, i) followed by post-treatment and the like as necessary to give, ii) followed by post-treatment and the like and then isolation and/or purification to give, iii) without post-treatment, isolation, purification or the like to give, that is used a reaction mixture as it stands, and the like.

The chiral copper complex having a chiral ligand used in the present invention (Hereinafter may be referred to simply as "a chiral copper complex") may be chiral copper complex having a chiral ligand as described above, and includes, for example, a chiral copper complex described in Handbook of Enantioselective Catalysis (VCH, 1993); J. Am. Chem. Soc. 2001, 123, 5843; J. Org. Chem., 1998, 63, 6090; Angew. Chem. Int., Ed. 2004, 43, 1679; Dalton. Trans. 2003, 1881; Organic Letters, Vol. 6, No. 14, 2305 (2004); and the like, and a chiral copper complex capable of using in an asymmetric synthesis and the like. The above-mentioned chiral copper complex used in the present invention is particularly preferably a chiral copper complex obtained by reacting a chiral ligand with a copper complex.

1) Chiral Ligand

The chiral ligand used in the present invention may be any ligand which has an optically active site, is an optically active compound, and usable as a chiral ligand. The above-mentioned chiral ligand includes, for example, chiral ligands described in Catalytic Asymmetric Synthesis (Wiley-VCH, 2000); Handbook of Enantioselective Catalysis with Transition Metal Complex (VCH, 1993); ASYMMETRIC CATALYSIS IN ORGANIC SYNTHESIS (John Wiley & Sons Inc. (1994)); WO 2005/070875; and the like.

In more detail, the chiral ligand used in the present invention includes, for example, a monodentate ligand, a bidentate ligand, a tridentate ligand, a tetradentate ligand, and the like.

The monodentate ligand includes, for example, an optically active phosphorus compound, an optically active amine compound, an optically active alcohol compound, an optically active sulfur compound an optically active carbene compound and the like.

The optically active phosphorus compound may be a phosphorus compound having an optically active site in its molecule to form an optically active compound, and includes, for example, an optically active phosphorus compound represented by the following formulae (6) to (8). These optically active phosphorus compounds represented by the formulae (6) to (8) are an optically active phosphorus compound having an optically active site in its molecule.

$$PR^1_3 \tag{6}$$

wherein three of $R^1$ are the same or different and represents an optionally substituted hydrocarbon group, an optionally substituted heterocyclic group, an optionally substituted alkoxy group, an optionally substituted aryloxy group, an optionally substituted aralkyloxy group, an amino group or a substituted amino group; and two or three in three of $R^1$ may be combined with each other to form a ring.

(7)

wherein $R^2$ represents an optionally substituted hydrocarbon group or a substituted amino group; $Q^1$ represents a spacer; $Z^1$ and $Z^2$ independently represent an oxygen atom, a sulfur atom or —$NR^4$— (wherein $R^4$ represents a hydrogen atom or a protecting group).

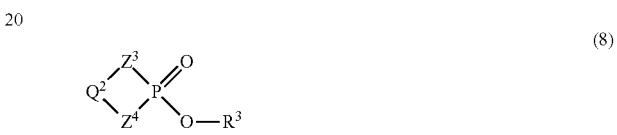

(8)

wherein $R^3$ represents a hydrogen atom or an optionally substituted hydrocarbon group; $Q^2$ represents a spacer; $Z^3$ and $Z^4$ independently represent an oxygen atom, a sulfur atom or —$NR^5$— (wherein $R^5$ represents a hydrogen atom or a protecting group).

The respective groups used in the formulae (6) to (8) are explained in detail.

The optionally substituted hydrocarbon group represented by $R^1$ to $R^3$ includes a hydrocarbon group and a substituted hydrocarbon group.

The hydrocarbon group includes, for example, an alkyl group, an alkenyl group, an alkynyl group, an alkadienyl group, an aryl group, an aralkyl group and the like.

The alkyl group may be linear, branched or cyclic and includes, for example, an alkyl group having 1 to 20, preferably 1 to 15, more preferably 1 to 10 carbon atom(s). Specific examples of the alkyl group include, for example, methyl, ethyl, n-propyl, 2-propyl, n-butyl, 1-methylpropyl, isobutyl, tert-butyl, n-pentyl, 1-methylbutyl, tert-pentyl, 2-methylbutyl, 3-methylbutyl, 2,2-dimethylpropyl, n-hexyl, 1-methylpentyl, 1-ethylbutyl, 2-methylpentyl, 3-methylpentyl, 4-methylpentyl, 2-methylpentan-3-yl, heptyl, octyl, nonyl, decyl, lauryl, stearyl, cyclopropyl, cyclobutyl, cyclopentyl, cyclohexyl and the like.

The alkenyl group may be linear or branched and includes, for example, an alkenyl group having 2 to 20, preferably 2 to 15, more preferably 2 to 10 carbon atoms. Specific examples of the alkenyl group include, for example, vinyl, propenyl, butenyl, pentenyl, hexenyl, heptenyl, octenyl, nonenyl, decenyl and the like.

The alkynyl group may be linear or branched and includes, for example, an alkynyl group having 2 to 20, preferably 2 to 15, more preferably 2 to 10 carbon atoms. Specific examples of the alkynyl group include, for example, ethynyl, propynyl, butynyl, pentynyl, hexynyl and the like.

The alkadienyl group may be linear, branched or cyclic and includes, for example, an alkadienyl group having two double bonds in arbitrary positions in the chain of the above-mentioned alkyl group and having 4 or more, preferably 4 to 20, more preferably 4 to 15, further preferably 4 to 10 carbon atoms. Specific examples of the alkadienyl group include, for example, 1,3-butadienyl, 2,3-dimethyl-1,3-butadienyl and the like.

The aryl group includes, for example, an aryl group having 6 to 20, preferably 6 to 15 carbon atoms. Specific examples of the aryl group include, for example, phenyl, naphthyl, anthryl, biphenyl and the like.

The aralkyl group includes, for example, an aralkyl group having 7 to 20, preferably 7 to 15 carbon atoms and an aralkyl group wherein at least one hydrogen atom of the above-mentioned alkyl group is substituted with the above-mentioned aryl group. Specific examples of the aralkyl group include, for example, benzyl, 1-phenylethyl, 2-phenylethyl, 1-phenylpropyl, 3-naphthylpropyl and the like.

The substituted hydrocarbon group (a hydrocarbon group having a substituent) includes a hydrocarbon group wherein at least one hydrogen atom of the above-mentioned hydrocarbon group is substituted with a substituent, and examples thereof include, for example, a substituted alkyl group, a substituted alkenyl group, a substituted alkynyl group, a substituted alkadienyl group, a substituted aryl group, a substituted aralkyl group and the like. The substituent will be described later (The same applies hereinafter).

Specific examples of the substituted alkyl group include, for example, methoxymethyl, ethoxymethyl and the like.

Specific examples of the substituted aryl group include, for example, tolyl (for example, 4-methylphenyl), xylyl (for example, 3,5-dimethylphenyl), 4-methoxy-3,5-dimethylphenyl, 4-methoxy-3,5-di-tert-butylphenyl and the like.

The optionally substituted heterocyclic group represented by $R^1$ includes a heterocyclic group and a substituted heterocyclic group. The heterocyclic group includes an aliphatic heterocyclic group and an aromatic heterocyclic group.

The aliphatic heterocyclic group includes, for example, an aliphatic heterocyclic group having 2 to 14 carbon atoms and a 3- to 8-membered, preferably 5- to 6-membered monocyclic, polycyclic or fused ring aliphatic heterocyclic group containing at least 1, preferably 1 to 3 heteroatom(s) such as a nitrogen atom, an oxygen atom and/or a sulfur atom. Specific examples of the aliphatic heterocyclic group include, for example, pyrrolidyl-2-one, piperidino, piperazinyl, morpholino, morpholinyl, tetrahydrofuryl, tetrahydropyranyl, thiolanyl and the like.

The aromatic heterocyclic group includes, for example, an aromatic heterocyclic group having 2 to 15 carbon atoms and a 3- to 8-membered, preferably 5- to 6-membered monocyclic, polycyclic or fused ring aromatic heterocyclic group containing at least 1, preferably 1 to 3 heteroatom(s) such as a nitrogen atom, an oxygen atom and/or a sulfur atom. Specific examples of the aromatic heterocyclic group include, for example, furyl, thienyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzoxazolyl, benzothiazolyl, acridyl, acrydinyl and the like.

The substituted heterocyclic group (a heterocyclic group having a substituent) includes a heterocyclic group wherein at least one hydrogen atom of the above-mentioned heterocyclic group is substituted with the substituent, and examples thereof include a substituted aliphatic heterocyclic group and a substituted aromatic heterocyclic group.

The optionally substituted alkoxy group includes an alkoxy group and a substituted alkoxy group.

The alkoxy group may be linear, branched or cyclic and includes, for example, an alkoxy group having 1 to 20 carbon atom(s). Specific examples of the alkoxy group include, for example, methoxy, ethoxy, n-propoxy, 2-propoxy, n-butoxy, 2-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, heptyloxy, octyloxy, nonyloxy, decyloxy, cyclohexyloxy and the like. The above-mentioned alkoxy group is particularly preferably an alkoxy group having 1 to 10, more preferably 1 to 6 carbon atom(s).

The substituted alkoxy group (an alkoxy group having a substituent) includes an alkoxy group in which at least one hydrogen atom of the above-mentioned alkoxy group is substituted with the substituent.

The optionally substituted aryloxy group includes an aryloxy group and a substituted aryloxy group.

The aryloxy group includes, for example, an aryloxy group having 6 to 20 carbon atoms. Specific examples of the aryloxy group include, for example, phenyloxy, naphthyloxy, anthryloxy and the like. The above-mentioned aryloxy group is particularly preferably an aryloxy group having 6 to 14 carbon atoms.

The substituted aryloxy group (an aryloxy group having a substituent) includes an aryloxy group in which at least one hydrogen atom of the above-mentioned aryloxy group is substituted with the substituent.

The optionally substituted aralkyloxy group includes an aralkyloxy group and a substituted aralkyloxy group.

The aralkyloxy group includes, for example, an aralkyloxy group having 7 to 20 carbon atoms. Specific examples of the aralkyloxy group include, for example, benzyloxy, 2-phenylethoxy, 1-phenylpropoxy, 2-phenylpropoxy, 3-phenylpropoxy, 1-phenylbutoxy, 2-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy and the like. The above-mentioned aralkyloxy group is particularly preferably an aralkyloxy group having 7 to 12 carbon atoms.

The substituted aralkyloxy group (an aralkyloxy group having a substituent) includes an aralkyloxy group wherein at least one hydrogen atom of the above-mentioned aralkyloxy group is substituted with the substituent.

The substituted amino group represented by $R^1$ and $R^2$ includes a linear or cyclic amino group wherein one or two hydrogen atom(s) is/are substituted with a substituent (s) such as an amino-protecting group and the like. The above-mentioned amino-protecting group may be any groups that are usually used as an amino-protecting group, and include, for example, groups described as an amino-protecting group in "PROTECTIVE GROUPS IN ORGANIC SYNTHESIS THIRD EDITION (JOHN WILEY & SONS INC. (1999))". Specific examples of the amino-protecting group include, for example, an optionally substituted hydrocarbon group (for example, an alkyl group, an aryl group, an aralkyl group and the like), an optionally substituted acyl group, an optionally substituted alkoxycarbonyl group, an optionally substituted aryloxycarbonyl group, an optionally substituted aralkyloxycarbonyl group, a substituted sulfonyl group and the like.

The optionally substituted hydrocarbon group as exemplified by specific examples of the amino-protecting group, such as, for example, the alkyl group, the aryl group, the aralkyl group and the like, may have the same meaning as the respective groups of the optionally substituted hydrocarbon group described above.

Specific examples of the amino group substituted with the alkyl group, that is, an alkyl-substituted amino group include, for example, a mono- or dialkylamino group such as N-methylamino, N,N-dimethylamino, N,N-diethylamino, N,N-diisopropylamino, N-cyclohexylamino and the like.

Specific examples of the amino group substituted with the aryl group, that is, an aryl-substituted amino group include, for example, a mono- or diarylamino group such as N-phenylamino, N,N-diphenylamino, N-naphthylamino, N-naphthyl-N-phenylamino and the like.

Specific examples of the amino group substituted with the aralkyl group, that is, an aralkyl-substituted amino group include, for example, a mono- or diaralkylamino group such as N-benzylamino, N,N-dibenzylamino and the like. Also, examples thereof include a di-substituted amino group such as N-methyl-N-phenylamino, N-benzyl-N-methylamino and the like.

The optionally substituted acyl group includes an acyl group and a substituted acyl group.

The acyl group may be linear, branched or cyclic and includes, for example, an acyl group having 1 to 20 carbon atom(s) derived from an acid such as carboxylic acid, sulfonic acid, sulfinic acid, phosphinic acid, phosphonic acid and the like.

The acyl group derived from carboxylic acid includes an acyl group derived from carboxylic acid such as aliphatic carboxylic acid and aromatic carboxylic acid, and includes, for example, an acyl group represented by the formula: —$COR^b$; wherein $R^b$ represents a hydrogen atom, an optionally substituted hydrocarbon group or an optionally substituted heterocyclic group (Said optionally substituted hydrocarbon group and said optionally substituted heterocyclic group may be the same respective groups as described above). Specific examples of the acyl group derived from carboxylic acid include, for example, formyl, acetyl, propionyl, butyryl, pivaloyl, pentanoyl, hexanoyl, lauroyl, stearoyl, benzoyl, 1-naphthoyl, 2-naphthoyl and the like. The above-mentioned acyl group is particularly preferably an acyl group having 2 to 18 carbon atoms.

The sulfonic acid-derived acyl group includes a sulfonyl group. The sulfonyl group includes a substituted sulfonyl group and includes, for example, a substituted sulfonyl group represented by the formula: $R^c$—$SO_2$—; wherein $R^c$ represents an optionally substituted hydrocarbon group, an optionally substituted heterocyclic group, an amino group, a substituted amino group, an optionally substituted alkoxy group, an optionally substituted aryloxy group or an optionally substituted aralkyloxy group (Said optionally substituted hydrocarbon group, said optionally substituted heterocyclic group, the substituted amino group, the optionally substituted alkoxy group, the optionally substituted aryloxy group and the optionally substituted aralkyloxy group may be the same respective groups as described above). Specific examples of the sulfonyl group include, for example, methanesulfonyl, trifluoromethanesulfonyl, benzenesulfonyl, p-toluenesulfonyl and the like. The sulfonyl group wherein $R^c$ is the amino group or the substituted amino group is an aminosulfonyl group. Specific examples of the aminosulfonyl group include, for example, aminosulfonyl, dimethylaminosulfonyl, diethylaminosulfonyl, diphenylaminosulfonyl and the like. The substituted sulfonyl group wherein $R^c$ is the optionally substituted alkoxy group, the optionally substituted aryloxy group or the optionally substituted aralkyloxy group is an alkoxxysulfonyl group. Specific examples of the alkoxysulfonyl group include, for example, methoxysulfonyl, ethoxysulfonyl, phenoxysulfonyl, benzyloxysulfonyl and the like.

The sulfinic acid-derived acyl group includes a sulfinyl group. The sulfinyl group includes a substituted sulfinyl group, and includes, for example, a substituted sulfinyl group represented by the formula: $R^d$—SO—; wherein $R^d$ represents an optionally substituted hydrocarbon group, a optionally substituted heterocyclic group or a substituted amino group (Said optionally substituted hydrocarbon group, said optionally substituted heterocyclic group and said substituted amino group may be the same respective groups as described above). Specific examples of the sulfinyl group include, for example, methanesulfinyl, tert-butylsulfinyl, benzenesulfinyl and the like.

The phosphinic acid-derived acyl group includes a phosphinyl group. The phosphinyl group includes a substituted phosphinyl group, and includes, for example, a substituted sulphinyl group represented by the formula: $(R^e)_2$—PO—; wherein two of $R^e$ may be the same or different and represent an optionally substituted hydrocarbon group (Said optionally substituted hydrocarbon group may be the same optionally substituted hydrocarbon group as described above). Specific examples of the phosphinyl group include, for example, dimethylphosphinyl, diphenylphosphinyl and the like.

The phosphonic acid-derived acyl group includes a phosphonyl group. The phosphonyl group includes a substituted phosphonyl group, and includes, for example, a substituted phosphonyl group represented by the formula: $(R^fO)_2$—PO—; wherein two of $R^f$ may be the same or different and represent an optionally substituted hydrocarbon group (Said the optionally substituted hydrocarbon group may be the same optionally substituted hydrocarbon group as described above). Specific examples of the phosphonyl group include, for example, dimethylphosphonyl, diphenylphosphonyl and the like.

The substituted acyl group (an acyl group having a substituent) includes an acyl group where in at least one hydrogen atom of the above-mentioned acyl group is substituted with the substituent.

Specific examples of the amino group substituted with the optionally substituted acyl group, that is, an acylamino group includes, for example, formylamino, acetylamino, propionylamino, pivaloylamino, pentanoylamino, hexanoylamino, benzoylamino and the like.

Specific examples of the amino group substituted with the sulfonyl group among the acyl group, that is, a sulfonylamino group include, for example, —$NHSO_2CH_3$, —$NHSO_2C_6H_5$, —$NHSO_2C_6H_4$—$CH_3$, —$NHSO_2CF_3$, —$NHSO_2OCH_3$, —$NHSO_2NH_2$ and the like.

Specific examples of the amino group substituted with the optionally substituted alkoxy group, the optionally substituted aryloxy group or the optionally substituted aralkyloxy group among the acyl group, that is, an alkoxysulfonylamino group include, for example, methoxysulfonylamino, ethoxysulfonylamino, phenoxysulfonylamino, benzyloxysulfonylamino and the like.

The optionally substituted alkoxycarbonyl group includes an alkoxycarbonyl group and a substituted alkoxycarbonyl group.

The alkoxycarbonyl group may be linear, branched or cyclic and includes, for example, an alkoxycarbonyl group having 2 to 20 carbon atoms. Specific examples of the alkoxycarbonyl group include, for example, methoxycarbonyl, ethoxycarbonyl, n-propoxycarbonyl, 2-propoxycarbonyl, n-butoxycarbonyl, tert-butoxycarbonyl, pentyloxycarbonyl, hexyloxycarbonyl, 2-ethylhexyloxycarbonyl, lauryloxycarbonyl, stearyloxycarbonyl, cyclohexyloxycarbonyl and the like.

The substituted alkoxycarbonyl group (an alkoxycarbonyl group having a substituent) includes an alkoxycarbonyl group wherein at least one hydrogen atom of the above-mentioned alkoxycarbonyl group is substituted with the substituent.

Specific examples of the amino group substituted with the optionally substituted alkoxycarbonyl group, that is, an alkoxycarbonylamino group includes, for example, methoxycarbonylamino, ethoxycarbonylamino, n-propoxycarbonylamino, n-butoxycarbonylamino, tert-butoxycarbonylamino, pentyloxycarbonylamino, hexyloxycarbonylamino and the like.

The optionally substituted aryloxycarbonyl group includes an aryloxycarbonyl group and a substituted aryloxycarbonyl group.

The aryloxycarbonyl group includes, for example, an aryloxycarbonyl group having 7 to 20 carbon atoms. Specific examples of the aryloxycarbonyl group include, for example, phenoxycarbonyl, naphthyloxycarbonyl and the like.

The substituted aryloxycarbonyl group (an aryloxycarbonyl group having a substituent) includes an aryloxycarbonyl group wherein at least one hydrogen atom of the above-mentioned aryloxycarbonyl group is substituted with the substituent.

Specific examples of the amino group substituted with the optionally substituted aryloxycarbonyl group, that is, an aryloxycarbonylamino group includes, for example, an amino group wherein one hydrogen atom of an amino group is substituted with the above-mentioned aryloxycarbonyl group, and specific examples thereof include, for example, phenoxycarbonylamino, naphthyloxycarbonylamino and the like.

The optionally substituted aralkyloxycarbonyl group includes an aralkyloxycarbonyl group and a substituted aralkyloxycarbonyl group.

The aralkyloxycarbonyl group includes, for example, an aralkyloxy carbonyl group having 8 to 20-carbon atoms. Specific examples of the aralkyloxycarbonyl group include, for example, benzyloxycarbonyl, phenethyloxycarbonyl, 9-fluorenylmethyloxycarbonyl and the like.

The substituted aralkyloxycarbonyl group (an aralkyloxycarbonyl group having a substituent) includes an aralkyloxycarbonyl group wherein at least one hydrogen atom of the above-mentioned aralkyloxycarbonyl group is substituted with the substituent.

Specific examples of the amino group substituted with the optionally substituted aralkyloxycarbonyl group, that is, an aralkyloxycarbonylamino group includes, for example, benzyloxycarbonylamino, phenethyloxycarbonylamino, 9-fluorenylmethyloxycarbonylamino and the like.

Also, the cyclic amino group includes, for example, an amino group in which a nitrogen-containing ring is formed by bonding through an alkylene group. Said alkylene group may be linear or branched and includes, for example, an alkylene group having 1 to 6 carbon atom(s). Specific examples of the alkylene group include, for example, methylene, ethylene, propylene, trimethylene, 2-methylpropylene, 2,2-dimethylpropylene, 2-ethylpropylene and the like. The above-mentioned alkylene group may have an oxygen atom, a nitrogen atom, a carbonyl group and the like, or a double bond in an arbitrary position of at the terminal position or in the chain of the alkylene group.

The spacer represented by $Q^1$ and $Q^2$ includes an optionally substituted divalent organic group and the like. Specific examples of the optionally substituted divalent organic group include, for example, an alkylene group, an arylene group, a heteroarylene group and the like. Also, the divalent organic group may have at least one heteroatom or heteroatomic group such as an oxygen atom, a carbonyl group, a sulfur atom, an imino group, a substituted imino group and the like, in an arbitrary position of the terminal position or in the chain of said organic group. Further, the spacer may have an optically active site.

The alkylene group may be linear or branched and includes, for example, an alkylene group having 1 to 10 carbon atom(s). Specific examples of the alkylene group include, for example, methylene, ethylene, propylene, trimethylene, tetramethylene, pentamethylene, hexamethylene, heptamethylene octamethylene, nonamethylene, decamethylene, 2-methylpropylene, 2,2-dimethylpropylene, 2-ethylpropylene and the like.

The arylene group includes, for example, an arylene group having 6 to 20 carbon atoms. Specific examples of the arylene group include, for example, phenylene, biphenyldiyl, binaphthalenediyl, bisbenzodioxoldiyl and the like.

The heteroarylene group includes, for example, a heteroarylene group having 2 to 20 carbon atoms and a 3- to 8-membered, preferably 5- to 6-membered monocyclic, polycyclic or fused ring heteroarylene group containing at least 1, preferably-1 to 3 heteroatom(s) such as a nitrogen atom, an oxygen atom and/or a sulfur atom. Specific examples of the heteroarylene group include, for example, bipyridinediyl, bisbenzothioldiyl, bisthioldiyl and the like.

The substituted imino group includes an imino group wherein the hydrogen atom of an imino group (—NH—) is substituted with an amino-protecting group. The amino-protecting group may be the same amino-protecting group as described above in the substituted amino group.

The divalent organic group having a heteroatom or a heteroatomic group includes —CH$_2$—O—CH$_2$—, —C$_6$H$_4$—O—C$_6$H$_4$— and the like.

These divalent organic groups may be substituted with a substituent described later.

When the spacer has an optically active site, specific examples of the spacer having an optically active site include, for example, 1,2-dimethylethylene, 1,2-cyclohexylene, 1,2-diphenylethylene, 1,2-di(4-methylphenyl)ethylene, 1,2-dicyclohexylethylene, 1,3-dimethyltrimethylene, 1,3-diphenyltrimethylene, 1,4-dimethyltetramethylene, 1,3-dioxolane-4,5-diyl, biphenyldiyl, binaphthalenediyl and the like. These spacer shaving an optically active site include those in (R), (S), (R,R) or (S,S) form.

The protecting group represented by $R^4$ in —NR$^4$-represented by $Z^1$ and $Z^2$, and the protecting group represented by $R^5$ in —NR$^5$— represented by $Z^3$ and $Z^4$, may be the same amino-protecting group as described above in the substituted amino group.

The substituent includes, for example, an optionally substituted hydrocarbon group, an optionally substituted heterocyclic group, a halogen atom, a halogenated hydrocarbon group, an optionally substituted alkoxy group, an optionally substituted aryloxy group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an oxo group and the like.

As the substituent, the optionally substituted hydrocarbon group, the optionally substituted heterocyclic group, the optionally substituted alkoxy group, the optionally substituted aryloxy group, the optionally substituted aralkyloxy group, the optionally substituted acyl group, the optionally substituted alkoxycarbonyl group, the optionally substituted aryloxycarbonyl group, the optionally substituted aralkyloxycarbonyl group, and the substituted amino group may be the same respective groups as described above and the respective groups explained in the substituted amino group.

The halogen atom includes fluorine, chlorine, bromine, iodine and the like.

The halogenated hydrocarbon group includes those groups wherein at least one hydrogen atom of the above-mentioned hydrocarbon group is halogenated (for example, fluorinated, chlorinated, brominated or iodinated). The halogenated hydrocarbon group includes, for example, a halogenated alkyl group, a halogenated aryl group and a halogenated aralkyl group.

The halogenated alkyl group includes, for example, a halogenated alkyl group having 1 to 20 carbon atom(s). Specific examples thereof include, chloromethyl, bromomethyl, chloroethyl, bromopropyl, fluoromethyl, fluoroethyl, fluoropropyl, fluorobutyl, fluoropentyl, fluorohexyl, fluoroheptyl, fluorooctyl, fluorononyl, fluorodecyl, difluoromethyl, difluoroethyl, fluorocyclohexyl, trifluoromethyl, 2,2,2-trifluoroethyl, 3,3,3-trifluoropropyl, pentafluoroethyl, 3,3,4,4,4-pentafluorobutyl, perfluoro-n-propyl, perfluoroisopropyl, perfluoro-n-butyl, perfluoroisobutyl, perfluoro-tert-butyl, perfluoro-sec-butyl, perfluoropentyl, perfluoroisopentyl, perfluoro-tert-pentyl, perfluoro-n-hexyl, perfluoroisohexyl, perfluoroheptyl, perfluorooctyl, perfluorononyl, perfluorodecyl, perfluorooctylethyl, perfluorocyclopropyl, perfluorocyclopentyl, perfluorocyclohexyl and the like. The above-mentioned halogenated alkyl group is particularly preferably a halogenated alkyl group having 1 to 10 carbon atom(s).

The halogenated aryl group includes, for example, a halogenated aryl group having 6 to 20 carbon atoms. Specific examples thereof include 2-fluorophenyl, 3-fluorophenyl, 4-fluorphenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-trichloromethylphenyl, 3-trichloromethylphenyl, 4-trichloromethylphenyl, perfluorophenyl, perfluoronaphthyl, perfluoroanthryl, perfluorobiphenyl and the like. The above-mentioned halogenated aryl group is particularly preferably a halogenated aryl group having 6 to 15 carbon atoms.

The halogenated aralkyl group includes those groups wherein at least one hydrogen atom of the above-mentioned aralkyl group is substituted with the halogen atom, and includes, for example, a halogenated aralkyl group having 7 to 20 carbon atoms. Specific examples thereof include 2-fluorobenzyl, 3-fluorobenzyl, 4-fluorobenzyl, 2-chlorobenzyl, 3-chlorobenzyl, 4-chlorobenzyl, 4-bromobenzyl, 4-iodobenzyl, 2-trifluoromethylbenzyl, 3-trifluoromethylbenzyl, 4-trifluoromethylbenzyl, 4-trichloromethylbenzyl, perfluorobenzyl and the like. The above-mentioned halogenated aralkyl group is particularly preferably a having 6 to 15 carbon atoms.

The optionally substituted heteroaryloxy group includes a heteroaryloxy group and a substituted heteroaryloxy group.

The heteroaryloxy group includes, for example, a heteroaryloxy group having 2 to 20 carbon atoms, preferably C2 to C15 carbon atoms, heteroaryloxy groups each containing at least 1, preferably 1 to 3, heteroatom(s) such as a nitrogen atom, an oxygen atom and a sulfur atom. Specific examples of the heteroaryloxy group include 2-pyridyloxy, 2-pyrazyloxy, 2-pyrimidyloxy, 2-quinolyloxy and the like.

The substituted heteroaryloxy group (a heteroaryloxy group having a substituent) includes a heteroaryloxy group wherein at least one hydrogen atom of the above-mentioned aralkyloxy group is substituted with the substituent. The substituent may be the same substituent as described above unless otherwise specified (The same applies hereinafter).

The optionally substituted alkylthio group includes an alkylthio group and a substituted alkylthio group.

The alkylthio group may be linear, branched or cyclic and includes, for example, an alkylthio group having 1 to 20 carbon atom(s). Specific examples of the alkylthio group include, for example, methylthio, ethylthio, n-propylthio, 2-propylthio, n-butylthio, 2-butylthio, isobutylthio, tert-butylthio, pentylthio, hexylthio, cyclohexylthio and the like. The above-mentioned alkylthio group is particularly preferably an alkylthio group having 1 to 10, more preferably 1 to 6 carbon atom(s).

The substituted alkylthio group (an alkylthio group having a substituent) includes an alkylthio group wherein at least one hydrogen atom of the above-mentioned alkylthio group is substituted with the substituent.

The optionally substituted arylthio group includes an arylthio group and a substituted arylthio group.

The arylthio group includes, for example, an arylthio group having 6 to 20 carbon atoms. Specific examples of the arylthio group include phenylthio, naphthylthio and the like.

The above-mentioned arylthio group is particularly preferably an arylthio group having 6 to 14 carbon atoms.

The substituted arylthio group (an arylthio group having a substituent) includes an arylthio group wherein at least one hydrogen atom of the above-mentioned arylthio group is substituted with the substituent.

The optionally substituted aralkylthio group includes an aralkylthio group and a substituted aralkylthio group.

The aralkylthio group includes, for example, an aralkylthio group having 7 to 20 carbon atoms. Specific examples of the aralkylthio group include, for example, benzylthio, 2-phenethylthio and the like. The above-mentioned aralkylthio group is particularly preferably an aralkylthio group having 7 to 12 carbon atoms.

The substituted aralkylthio group (an aralkylthio group having a substituent) includes an aralkylthio group wherein at least one hydrogen atom of the above-mentioned aralkylthio group is substituted with the substituent.

The optionally substituted heteroarylthio group includes a heteroarylthio group and a substituted heteroarylthio group.

The heteroarylthio group includes, for example, a heteroarylthio group having 2 to 20 carbon atoms, preferably 2 to 15 carbon atoms, containing at least 1, preferably 1 to 3, heteroatom(s) such as a nitrogen atom, an oxygen atom and a sulfur atom. Specific examples of the heteroarylthio group include, for example, 4-pyridylthio, 2-benzimidazolylthio, 2-benzoxazolylthio, 2-benzothiazolylthio and the like.

The substituted heteroarylthio group (a heteroarylthio group having a substituent) includes a heteroarylthio group wherein at least one hydrogen atom of the above-mentioned heteroarylthio group is substituted with the substituent.

The optionally substituted acyloxy group includes an acyloxy group and a substituted acyloxy group.

The acyloxy group includes, for example, an acyloxy group having 2 to 20 carbon atoms derived from a carboxylic acid such as an aliphatic carboxylic acid and an aromatic carboxylic acid. Specific examples of the acyloxy group include, for example, acetoxy, propionyloxy, butyryloxy, pivaloyloxy, pentanoyloxy, hexanoyloxy, lauroyloxy, stearoyloxy, benzoyloxy and the like. The acyloxy group is particularly preferably a having 2 to 18 carbon atoms acyloxy group.

The substituted acyloxy group (an acyloxy group having a substituent) includes an acyloxy group wherein at least one hydrogen atom of the above-mentioned acyloxy group is substituted with the substituent.

The optionally substituted alkoxythiocarbonyl group includes an alkoxythiocarbonyl group and a substituted alkoxythiocarbonyl group.

The alkoxythiocarbonyl group may be linear, branched or cyclic and includes, for example, an alkoxythiocarbonyl group having 2 to 20 carbon atoms. Specific examples of the alkoxythiocarbonyl group include, for example, methoxythiocarbonyl, ethoxythiocarbonyl, n-propoxythiocarbonyl, 2-propoxythiocarbonyl, n-butoxythiocarbonyl, tert-butoxythiocarbonyl, pentyloxythiocarbonyl, hexyloxythiocarbonyl, 2-ethylhexyloxythiocarbonyl, lauryloxythiocarbonyl, stearyloxythiocarbonyl, cyclohexyloxythiocarbonyl and the like.

The substituted alkoxythiocarbonyl group (an alkoxythiocarbonyl group having a substituent) includes an alkoxythiocarbonyl group wherein at least one hydrogen atom of the above-mentioned alkoxythiocarbonyl group is substituted with the substituent.

The optionally substituted aryloxythiocarbonyl group includes an aryloxythiocarbonyl group and a substituted aryloxythiocarbonyl group.

The aryloxythiocarbonyl group includes, for example, an aryloxythiocarbonyl group having 7 to 20 carbon atoms. Specific examples of the aryloxythiocarbonyl group include, for example, phenoxythiocarbonyl, naphthyloxythiocarbonyl and the like.

The substituted aryloxythiocarbonyl group (an aryloxythiocarbonyl group having a substituent) includes an aryloxythiocarbonyl group wherein at least one hydrogen atom of the above-mentioned aryloxythiocarbonyl group is substituted with the substituent.

The optionally substituted aralkyloxythiocarbonyl group includes an aralkyloxythiocarbonyl group and a substituted aralkyloxythiocarbonyl group.

The aralkyloxythiocarbonyl group includes, for example, an aralkyloxythiocarbonyl group having 8 to 20 carbon atoms. Specific examples of the aralkyloxythiocarbonyl group include, for example, benzyloxythiocarbonyl, phenethyloxythiocarbonyl, 9-fluorenylmethyloxythiocarbonyl and the like.

The substituted aralkyloxythiocarbonyl group (an aralkyloxythiocarbonyl group having a substituent) includes an aralkyloxythiocarbonyl group wherein at least one hydrogen atom of the above-mentioned aralkyloxythiocarbonyl group is substituted with the substituent.

The optionally substituted alkylthiocarbonyl group includes an alkylthiocarbonyl group and a substituted alkylthiocarbonyl group.

The alkylthiocarbonyl group may be linear, branched or cyclic and includes, for example, an alkylthiocarbonyl group having 2 to 20 carbon atoms. Specific examples of the alkylthiocarbonyl group include, for example, methylthiocarbonyl, ethylthiocarbonyl, n-propylthiocarbonyl, for example, 2-propylthiocarbonyl, n-butylthiocarbonyl, tert-butylthiocarbonyl, pentylthiocarbonyl, hexylthiocarbonyl, 2-ethylhexythiocarbonyl, laurylthiocarbonyl, stearylthiocarbonyl, cyclohexylthiocarbonyl and the like.

The substituted alkylthiocarbonyl group (an alkylthiocarbonyl group having a substituent) includes an alkylthiocarbonyl group wherein at least one hydrogen atom of the above-mentioned alkylthiocarbonyl group is substituted with the substituent.

The optionally substituted arylthiocarbonyl group includes an arylthiocarbonyl group and a substituted arylthiocarbonyl group.

The arylthiocarbonyl group includes, for example, an arylthiocarbonyl group having 7 to 20 carbon atoms. Specific examples of the arylthiocarbonyl group include phenylthiocarbonyl, naphthylthiocarbonyl and the like.

The substituted arylthiocarbonyl group (an arylthiocarbonyl group having a substituent) includes an arylthiocarbonyl group wherein at least one hydrogen atom of the above-mentioned arylthiocarbonyl group is substituted with the substituent.

The optionally substituted aralkylthiocarbonyl group includes an aralkylthiocarbonyl group and a substituted aralkylthiocarbonyl group.

The aralkylthiocarbonyl group includes, for example, an aralkylthiocarbonyl group having 8 to 20 carbon atoms. Specific examples of the aralkylthiocarbonyl group include, for example, benzylthiocarbonyl, phenethylthiocarbonyl, 9-fluorenylmethylthiocarbonyl and the like.

The substituted aralkylthiocarbonyl group (an aralkylthiocarbonyl group having a substituent) includes an aralkylthiocarbonyl group wherein at least one hydrogen atom of the above-mentioned aralkylthiocarbonyl group is substituted with the substituent.

The optionally substituted carbamoyl group includes a carbamoyl group and a substituted carbamoyl group.

The substituted carbamoyl group includes a carbamoyl group wherein one or two hydrogen atom(s) of an amino group in the carbamoyl group are substituted with a substituent such as an optionally substituted hydrocarbon group and the like. The optionally substituted hydrocarbon group is the same hydrocarbon group as described above. Specific examples of the substituted carbamoyl group include, for example, N-methylcarbamoyl, N,N-diethylcarbamoyl, N-phenylcarbamoyl and the like.

The substituted phosphino group includes a phosphino group wherein one or two hydrogen atom(s) is substituted with a substituent such as an optionally substituted hydrocarbon group and the like. The optionally substituted hydrocarbon group is the same hydrocarbon group as described above. Specific examples of the substituted phosphino group include, for example, dimethylphosphino, diethylphosphino, diphenylphosphino, methylphenylphosphino and the like.

The substituted silyl group includes, for example, a tri-substituted silyl group wherein three hydrogen atoms in a silyl group are substituted with a substituent such as the above-mentioned optionally substituted hydrocarbon group and the above-mentioned optionally substituted alkoxy group. Specific examples of the substituted silyl group include, for example, trimethylsilyl, triethylsilyl, tri(2-propyl)silyl, tert-butyldimethylsilyl, tert-butyldiphenylsilyl, triphenylsilyl, tert-butylmethoxyphenylsilyl, tert-butoxydiphenylsilyl and the like.

The substituted silyloxy group includes, for example, a tri-substituted silyloxy group having 1 to 18 carbon atom(s) tri-substituted silyloxy groups wherein 1 to 3 hydrogen atom(s) in a silyloxy group is substituted with a substituent such as the above-mentioned optionally substituted hydrocarbon group and the above-mentioned optionally substituted alkoxy group. Specific examples of the substituted silyloxy group include, for example, trimethylsilyloxy, triethylsilyloxy, tri(2-propyl)silyloxy, tert-butyldimethylsilyloxy, tert-butyldiphenylsilyloxy, triphenylsilyloxy, tert-butylmethoxyphenylsilyloxy, tert-butoxydiphenylsilyloxy and the like.

The optionally substituted alkylenedioxy group includes an alkylenedioxy group and a substituted alkylenedioxy group.

The alkylenedioxy group includes, for example, an alkylenedioxy group having 1 to 3 carbon atom(s). Specific examples of the alkylenedioxy group include, for example, methylenedioxy, ethylenedioxy, trimethylenedioxy, propylenedioxy and the like.

The substituted alkylenedioxy group (an alkylenedioxy group having a substituent) includes an alkylenedioxy group wherein at least one hydrogen atom of the above-mentioned alkylenedioxy group is substituted with the substituent. Specific examples of the substituted alkylenedioxy group include difluoromethylenedioxy and the like.

Specific examples of the optically active phosphorus compound include, for example, optically active phosphorus compounds shown below:

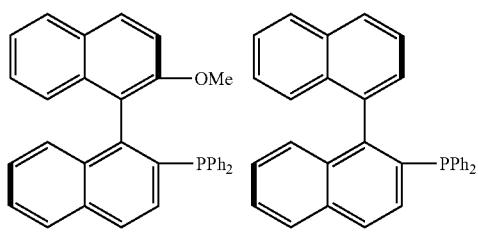

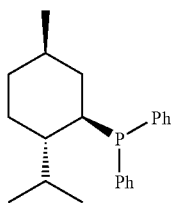

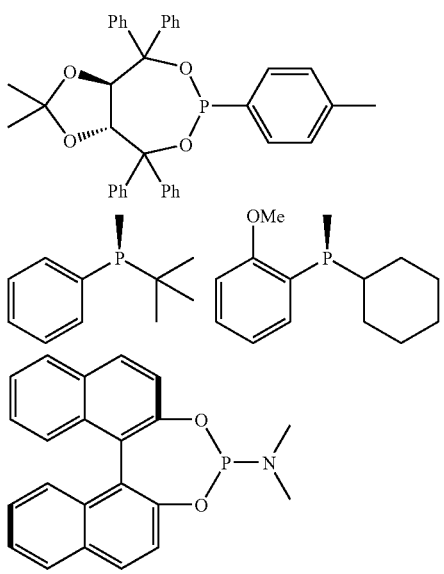

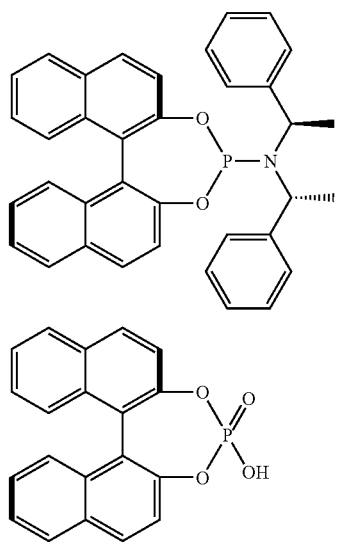

-continued

The optically active amine compound may be an amine compound having an optically active site in its molecule to form an optically active compound.

The optically active amine compound includes an optically active aliphatic amine compound, an optically active aromatic amine compound, an optically active nitrogen-containing heterocyclic compound and the like.

Specific examples of the optically active aliphatic amine compound include, for example, optically active menthylamine, optically active 1-phenylethylamine and the like. Specific examples of the optically active aromatic amine compound include, for example, an aniline compound having an optically active site and the like. Specific examples of the optically active nitrogen-containing compound include, for example, the compounds such as pyridine, piperidine, piperazine and oxazoline, having an optically active site, and the like. Here, the optically active oxazoline compound of the monodentate ligand is also included in the optically active amine compound.

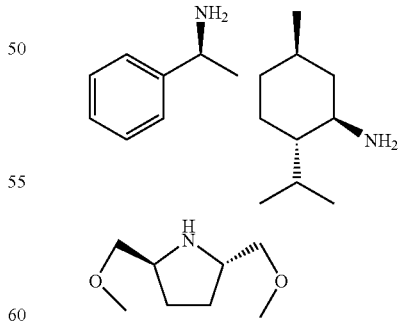

The optically active alcohol compound may be an alcohol compound having an optically active site in its molecule to form an optically active compound. Specific examples of the optically active alcohol compound include, for example, the optically active alcohol compounds shown below:

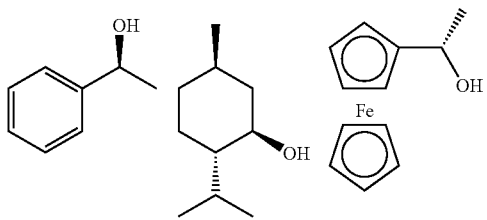

The optically active sulfur compound may be a sulfur compound having an optically active site in its molecule to form an optically active compound. Specific examples of the optically active sulfur compound include, for example, the optically active sulfur compound shown below:

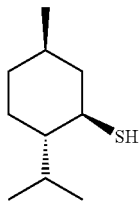

The optically active carbene compound may be a carbene compound having an optically active site in its molecule to form an optically active compound. Specific examples of the optically active carbene compound include, for example, the optically active carbene compounds shown below:

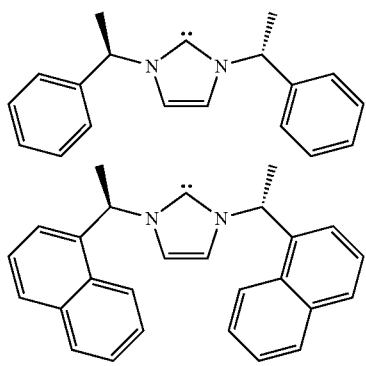

The bidentate ligand includes a bidentate optically active phosphorus compound such as an optically active diphosphine compound, a phosphine-phosphite compound and the like, an optically active diamine compound, an optically active aminoalcohol compound, an optically active diol compound, an optically active aminophosphine compound, an optically active phosphinoalcohol compound, an optically active aminothiol compound, an optically active bisoxazoline compound and the like.

The bidentate optically active phosphorus compound may be a bidentate phosphorus compound having an optically active site in its molecule to form an optically active compound, and includes, for example, an optically active phosphorus compound represented by the following formula (10).

The optically active phosphorus compound represented by the formula (10) is a phosphorus compound having an optically active site in its molecule.

$$R^6R^7P-Q^3-PR^8R^9 \quad (10)$$

wherein $R^6$ to $R^9$ independently represent an optionally substituted hydrocarbon group, an optionally substituted heterocyclic group, an optionally substituted alkoxy group, an optionally substituted aryloxy group, or an optionally substituted aralkyloxy group; and $Q^3$ represents a spacer. Also, $R^6$ and $R^7$ and P and/or $R^8$ and $R^9$ and P or $R^6$ and/or $R^7$ and $Q^3$ or $R^8$ and/or $R^9$ and $Q^3$ may be combined to form a ring. Provided that, $R^6$ to $R^9$ and $Q^3$ may be such a group that the phosphorus compound represented by the formula (10) is capable of forming the optically active phosphorus compound.

In the formula (10), the optionally substituted hydrocarbon group, the optionally substituted heterocyclic group, the optionally substituted alkoxy group, the optionally substituted aryloxy group and the optionally substituted aralkyloxy group represented by $R^6$ to $R^9$ may be the same respective groups as described above. The spacer represented by $Q^3$ may also be the same as the spacer explained in the above-mentioned $Q^1$ and $Q^2$.

Specific examples of the above-mentioned optically active phosphorus compound include, for example, an optically active diphosphine compound, that is an optically active form, such as 1,2-bis(anisylphenylphosphino)ethane (DI-PAMP), 1,2-bis(alkylmethylphosphino)ethane (BisP*), 2,3-bis(diphenylphosphino)butane (CHIRAPHOS), 1,2-bis (diphenylphosphino)propane (PROPHOS), 2,3-bis (diphenylphosphino)-5-norbornene (NORPHOS), 2,3-O-isopropylidene-2,3-dihydroxy-1,4-bis(diphenylphosphino) butane (DIOP), 1-cyclohexyl-1,2-bis(diphenylphosphino) ethane (CYCPHOS), 1-substituted-3,4-bis (diphenylphosphino)pyrrolidine (DEGPHOS), 2,4-bis-(diphenylphosphino)pentane (SKEWPHOS), 1,2-bis (substituted phospholano)benzene (DuPHOS), 1,2-bis (substituted phospholano)ethane (BPE), 1-((substituted phospholano)-2-(diphenylphosphino)benzene (UCAP-Ph), 1-(bis(3,5-dimethylphenyl)phosphino)-2-(substituted phospholano)benzene (UCAP-DM), 1-((substituted phospholano)-2-(bis(3,5-di(tert-butyl)-4-methoxyphenyl)phosphino) benzene (UCAP-DTBM), 1-((substituted phospholano)-2-(di-naphthalen-1-yl-phosphino)benzene (UCAP-(1-Nap)), 2,2'-bis(diphenylphosphino)-1,1'-bicylopentane (BICP), 2,2'-bis(diphenylphosphino)-1,1'-binaphthyl (BINAP), 2,2'-bis(diphenylphosphino)-1,1'-(5,5',6,6',7,7',8,8"-octa hydronaphthyl) ($H_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis (diphenylphosphino)-6,6'-dimethyl-1,1'-biphenyl (BICHEP), (4,4'-bi-1,3-benzodioxol)-5,5'-diylbis(diphenylphosphine) (SEGPHOS), (4,4'-bi-1,3-benzodioxol)-5,5'-diylbis[bis(3,5-dimethylphenyl)phosphine] (DM-SEGPHOS), [(4S)-[4,4'-bi-1,3-benzodioxol]-5,5'-diyl]bis[bis[3, 5-bis(1,1-dimethylethyl)-4-methoxyphenyl]phosphine] (DTBM-SEGPHOS) and the like. In addition, the optically active phosphorus compound includes optically active phosphorus compounds shown below:

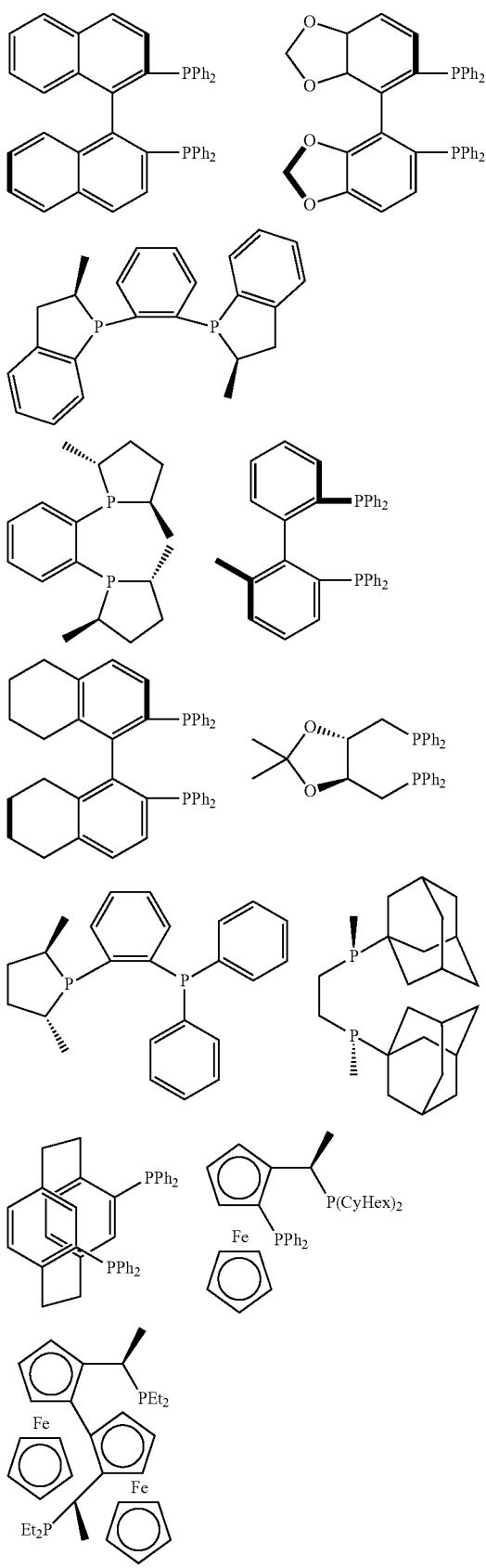

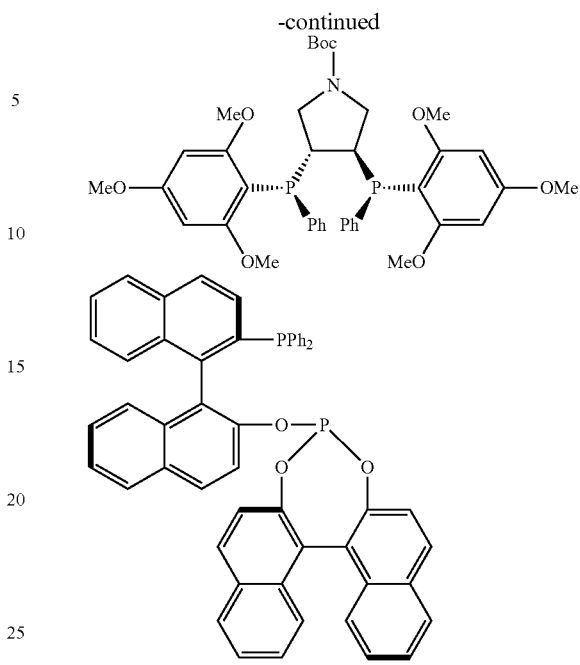

The bidentate optically active diamine compound may be a diamine compound having an optically active site in its molecule to form an optically active compound, and includes, for example, an optically active diamine compound represented by the following formula (11). The optically active diamine compound represented by the following formula (11) is a diamine compound having an optically active site in its molecule.

$$R^{10}R^{11}N-C_f(R^4R^5)-Q^4-C_g(R^{16}R^{17})-NR^{12}R^{13} \quad (11)$$

wherein $R^{10}$ to $R^{13}$ independently represent a hydrogen atom, an optionally substituted hydrocarbon group, an optionally substituted heterocyclic group, a substituted sulfonyl group or a protecting group; $R^{14}$ to $R^{17}$ independently represent a hydrogen atom, an optionally substituted hydrocarbon group or an optionally substituted heterocyclic group; $Q^4$ represents a spacer or a direct link; and f and g independently represent 0 or 1; provided that $R^{14}$ and $R^{15}$ and $C_f$, and/or $R^{16}$ and $R^{17}$ and $C_g$ may be combined to form a ring; $R^{10}$ or $R^{11}$ and $R^{14}$ or $R^{15}$ and $C_f$ and N, and/or $R^{12}$ or $R^{13}$ and $R^{16}$ or $R^{17}$ and $C_g$ and N may be combined to form a ring such as a carbon ring, an aliphatic ring and the like; $R^{14}$ or $R^{15}$ and $R^{16}$ or $R^{17}$ may be combined to form a ring; $R^{10}$ and $R^{11}$ and N, and/or $R^{12}$ and $R^{13}$ and N may be combined to form a ring; $R^{10}$ and $R^{11}$ and N, and/or $R^{12}$ and $R^{13}$ and N may be combined to form a heterocyclic ring such as a pyridine ring and the like; and $R^{14}$ or $R^{15}$ and $R^{16}$ or $R^{17}$ and $C_f$ and $Q^4$ and $C_g$ may be combined to form a ring such as an aromatic ring, an aliphatic ring and the like.

In the formula (11), the respective groups represented by $R^{10}$ to $R^{17}$, that is, an optionally substituted hydrocarbon group, an optionally substituted heterocyclic group, a substituted sulfonyl group and a protecting group may be the same respective groups as described above. The spacer represented by $Q^4$ may be the same spacer as explained in the above-mentioned $Q^1$, $Q^2$ and the like. The ring formed by combining $R^{14}$ and $R^{15}$, and/or $R^{16}$ and $R^{17}$; $R^{10}$ or $R^{11}$ and $R^{14}$ or $R^{15}$, and/or $R^{12}$ or $R^{13}$ and $R^{16}$ or $R^{17}$; $R^{14}$ or $R^{15}$ and $R^{16}$ or $R^{17}$; and $R^{10}$ and $R^{11}$, and/or $R^{12}$ and $R^{13}$ include, for example, a ring such as a carbon ring, a heterocyclic ring and the like, formed by bonding through an alkylene group. The alkylene group may be the same alkylene group as explained in the spacer of $Q^1$ and $Q^2$ in the formulae (7) and (8). Specific examples of the formed ring include, for example, a carbon ring such as aliphatic rings such as a cyclohexane ring and a benzene ring; a heterocyclic ring such as a pyridine ring and a piperidine ring; and the like. These formed rings may further have substituents described above.

The optically active diamine compound includes an optically active aromatic diamine an optically active aliphatic diamine, an optically active bisoxazoline compounds and the like.

The optically active bisoxazoline compound in the optically active diamine compound is a bidentate optically active bisoxazoline compound. The bidentate optically active bisoxazoline compound may be a bisoxazoline compound having an optically active site in its molecule to form an optically active compound, and includes, for example, an optically active bisoxazoline compound represented by the following formula (17). The optically active bisoxazoline compound represented by the following formula (17) is a bisoxazoline compound having an optically active site in its molecule. Provided that, the above-mentioned optically active oxazoline compound may be a tridentate or tetradentate ligand depending on a type of the spacer or the substituent on the oxazoline ring.

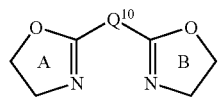
(17)

wherein the oxazoline rings A and B represent an optionally substituted oxazoline ring; and $Q^{10}$ represents a spacer or a direct link.

In the formula (17), the oxazoline ring represented by the oxazoline rings A and B includes an oxazoline ring (that is, an oxazoline ring not having a substituent) and a substituted oxazoline ring (that is, an oxazoline ring having a substituent). The substituent on the optionally substituted oxazoline ring may be the same substituent as described above. The spacer represented by $Q^{10}$ may be the same spacer as described above as $Q^1$ and $Q^2$.

Specific examples of the optically active diamine compound include, for example, 1,2-diphenylethylenediamine, 1,2-bis(4-methoxyphenyl)ethylenediamine, 1,2-dicyclohexylethylenediamine, 1,2-di(4-N,N-dimethylaminophenyl)ethylenediamine, 1,2-di(4-N,N-diethylaminophenyl)ethylenediamine, 1,2-di(4-N,N-dipropylaminophenyl)ethylenediamine, 1,2-(N-benzenesulfonyl)-1,2-di(4-N,N-dimethylaminophenyl)ethylenediamine, 1,2-(N-p-toluenesulfonyl)-1,2-di(4-N,N-dimethylaminophenyl)ethylenediamine, 1,2-(N-methanesulfonyl)-1,2-di(4-N,N-dimethylaminophenyl)ethylenediamine, 1,2-(N-trifluoromethanesulfonyl)-1,2-di(4-N,N-dimethylaminophenyl)ethylenediamine, 1,2-(N-benzenesulfonyl)-1,2-di(4-N,N-diethylaminophenyl)ethylenediamine, 1,2-(N-benzenesulfonyl)-1,2-di(4-N,N-dipropylaminophenyl)ethylenediamine, 1,2-di(4-sulfonylphenyl)ethylenediamine, 1,2-di(4-sodium oxysulfonylphenyl)ethylenediamine, 1,2-cyclohexanediamine, 1,2-cycloheptanediamine, 2,3-dimethylbutanediamine, 1-methyl-2,2-diphenylethylenediamine, 1-isobutyl-2, 2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine, 1-isopropyl-2,2-dinaphthylethylenediamine, bis[N-(2,4,6-trimethylphenyl)methyl-1,2-diphenylethylenediamine, N,N'-bis(phenylmethyl)-1,2-diphenyl-1,2-ethylenediamine, N,N'-bis(mesitylmethyl)-1,2-diphenyl-1,2-ethylenediamine, N,N'-bis(naphthylmethyl)-1,2-diphenyl-1,2-ethylenediamine and the like, that are the optically active form. In addition, the optically active diamine compound includes optically active diamine compounds shown below:

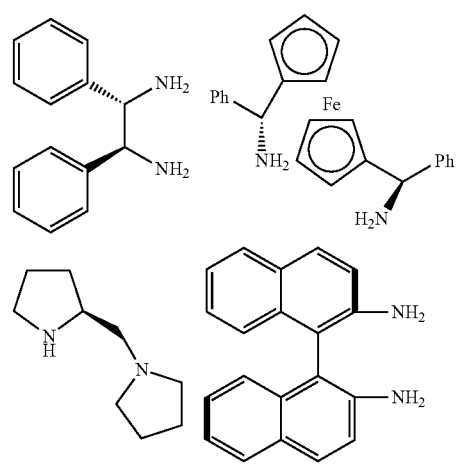

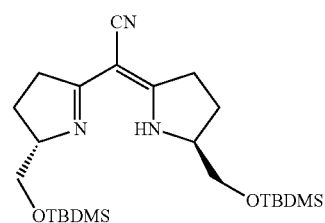

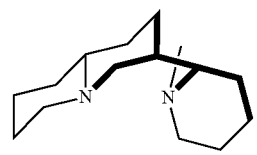

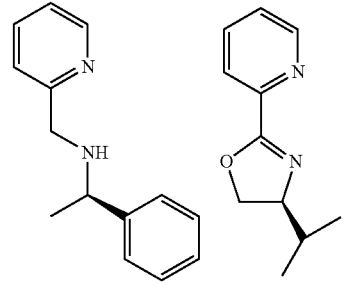

-continued

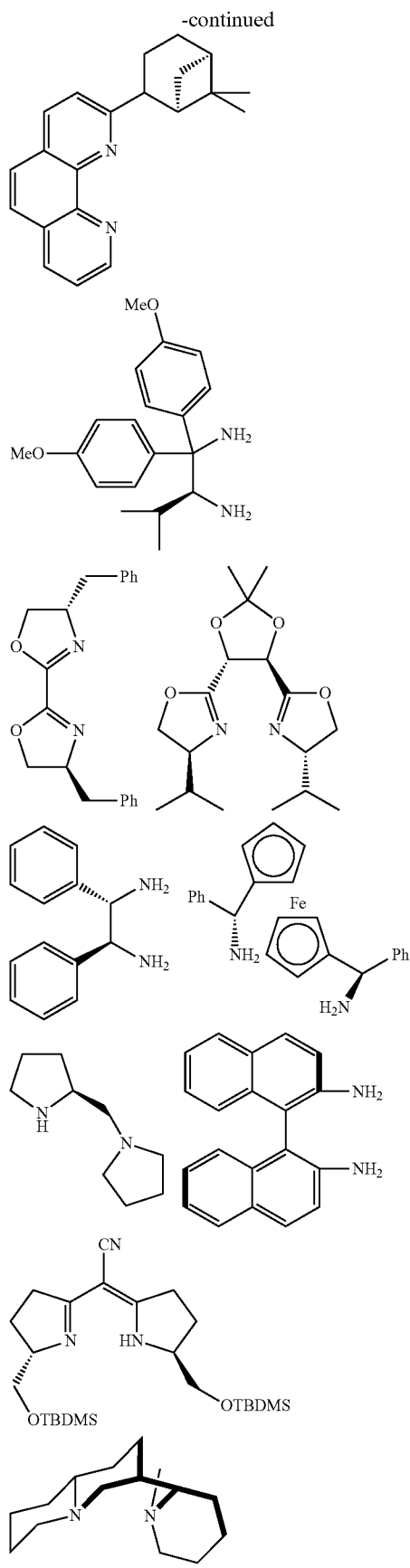

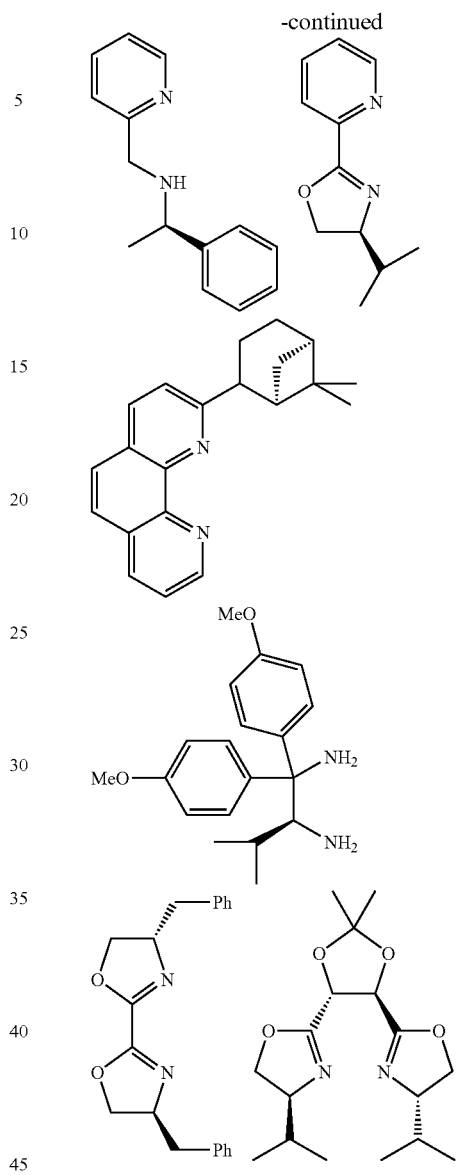

These optically active diamine compounds include (1R, 2R), (1S,2S), (1R,2S) and (1S,2R) as the optically active form, and these optically active diamine compounds are particularly preferably the (1R,2R) and (1S,2S) forms (here, unless otherwise specified with respect to the optically active form, the same applies to compounds having a similar structure, such as an optically active aminoalcohol compound described later). Specific examples of the (1R,2R) and (1S, 2S) form of the optically active diamine compound include, for example, (1R,2R)-1,2-diphenylethylenediamine,
(1S,2S)-1,2-diphenylethylenediamine,
(1R,2R)-1,2-di(4-N,N-dimethylaminophenyl)ethylenediamine,
(1S,2S)-1,2-di(4-N,N-dimethylaminophenyl)ethylenediamine,
(1R,2R)-1,2-di(4-N,N-diethylaminophenyl)ethylenediamine,
(1S,2S)-1,2-di(4-N,N-diethylaminophenyl)ethylenediamine, (1R,2R)-1,2-di(4-N,N-dipropylaminophenyl)ethylenediamine,
(1S,2S)-1,2-di(4-N,N-dipropylaminophenyl)ethylenediamine and the like.

Also, specific examples of the optically active bisoxazoline compound include, for example,
(S,S)-2,6-bis(4-isopropyl-2-oxazolin-2-yl)pyridine,
(R,R)-2,6-bis(4-isopropyl-2-oxazolin-2-yl)pyridine,
(S,S)-2,6-bis(4-phenyl-2-oxazolin-2-yl)pyridine,
(R,R)-2,6-bis(4-phenyl-2-oxazolin-2-yl)pyridine,
(S,S)-2,2'-isopropylidenebis(4-phenyl-2-oxazoline),
(R,R)-2,2'-isopropylidenebis(4-phenyl-2-oxazoline),
(S,S)-(−)-2,2'-isopropylidenebis(4-tert-butyl-2-oxazoline),
2,2'-methylenebis[(4R or 4S)-phenyl-5,5-dimethyloxazoline],
2,2'-methylenebis[(4R or 4S)-phenyl-5,5-diethyloxazoline],
2,2'-methylenebis[(4R or 4S)-phenyl-5,5-di-n-propyloxazoline], 2,2'-methylenebis[(4R or 4S)-phenyl-5,5-di-1-propyloxazoline],
2,2'-methylenebis[(4R or 4S)-phenyl-5,5-dicyclohexyloxazoline],
2,2'-methylenebis [(4R or 4S)-phenyl-5,5-diphenyloxazoline],
2,2'-methylenebis[(4R or 4S)-phenyl-5,5-di-(2-methylphenyl)oxazoline],
2,2'-methylenebis[(4R or 4S)-phenyl-5,5-di-(3-methylphenyl)oxazoline],
2,2'-methylenebis[(4R or 4S)-phenyl-5,5-di-(4-methylphenyl)oxazoline],
2,2'-methylenebis[(4R or 4S)-phenyl-5,5-di-(2-methoxyphenyl)oxazoline],
2,2'-methylenebis[(4R or 4S)-phenyl-5,5-di-(3-methoxyphenyl)oxazoline],
2,2'-methylenebis[(4R or 4S)-phenyl-5,5-di-(4-methoxyphenyl)oxazoline],
2,2'-methylenebis[spiro((4R or 4S)-phenyloxazoline-5,1'-cyclobutane)],
2,2'-methylenebis[spiro((4R or 4S)-phenyloxazoline-5,1'-cyclopentane)],
2,2'-methylenebis[spiro((4R or 4S)-phenyloxazoline-5,1'-cyclohexane)],
2,2'-methylenebis[spiro((4R or 4S)-phenyloxazoline-5,1'-cycloheptane)] and the like.

The bidentate optically active aminoalcohol compound may be an aminoalcohol compound having an optically active site in its molecule to form an optically active compound, and includes, for example, an optically active aminoalcohol compound represented by the following formula (12). The optically active aminoalcohol compound represented by the following formula (12) is an aminoalcohol compound having an optically active site in its molecule.

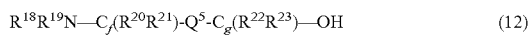

wherein $R^{18}$ and $R^{19}$ independently represent a hydrogen atom, an optionally substituted hydrocarbon group, an optionally substituted heterocyclic group, a substituted sulfonyl group or a protecting group; $R^{20}$ to $R^{23}$ independently represent a hydrogen atom, an optionally substituted hydrocarbon group or an optionally substituted heterocyclic group; $Q^5$ represents a spacer or a direct link; and f and g have the same meanings as defined above; provided that $R^{20}$ and $R^{21}$ and $C_f$ and/or $R^{22}$ and $R^{23}$ and $C_g$ may be combined to form a ring; $R^{18}$ or $R^{19}$ and $R^{20}$ or $R^2$ and N and $C_f$ may be combined to form a ring such as a carbon ring and an aliphatic ring; $R^{18}$ and $R^{19}$ may be combined to form a ring; $R^{18}$ and $R^{19}$ and N may be combined to form a heterocyclic ring such as a pyridine ring and the like; and $R^{20}$ and $R^2$ and $C_f$ and $Q^5$ may be combined to form a ring such as an aliphatic ring and an aromatic ring.

In the formula (12), the respective groups represented by $R^{18}$ to $R^{23}$, that is, an optionally substituted hydrocarbon group, an optionally substituted heterocyclic group, a substituted sulfonyl group and a protecting group may be the same respective groups as described above. The spacer represented by $Q^5$ may be the same spacer as explained in the above-mentioned $Q^1$ and $Q^2$.

The above-mentioned optically active aminoalcohol compound includes an optically active aromatic aminoalcohol, an optically active aliphatic aminoalcohol and the like. Specific examples of the optically active aminoalcohol compound include, for example, the optically active aliphatic aminoalcohol such as 1-amino-2-propanol, 2-amino-1-butanol, alaminol, leucinol, isoleucinol, 2-aminocyclohexanol, 4-aminocyclohexanol and 2-aminocyclohexanemethanol; the optically active aromatic aminoalcohol such as phenylglycinol, phenylalaminol, ephedrine, norephedrine, pseudoephedrine, 2-amino-1,2-diphenylethanol and 2-benzylaminocyclohexane methanol; and the like. In addition, the optically active aminoalcohol compound includes optically active aminoalcohols shown below:

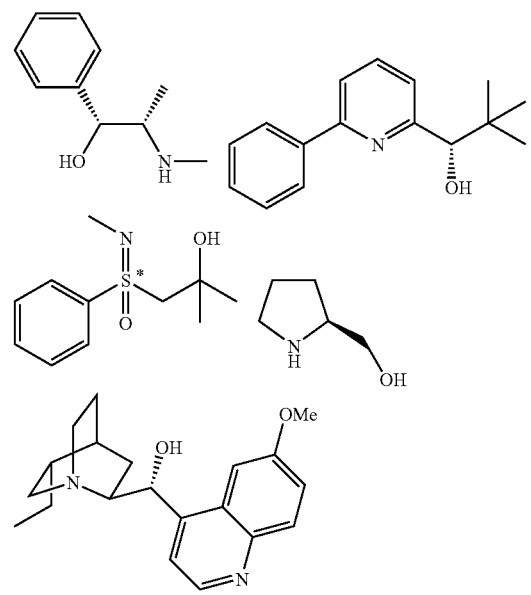

These optically active aminoalcohol compounds include (1R,2R), (1S,2S), (1R,2S) and (1S,2R) as the optically active form, and these optically active aminoalcohol compounds are particularly preferably the (1R,2R) and (1S,2S) form.

The bidentate optically active diol compound may be a diol compound having an optically active site in its molecule to form an optically active compound, and includes, for example, optically active diol compounds represented by the following formula (13). The optically active diol compound represented by the following formula (13) is a diol compound having an optically active site in its molecule.

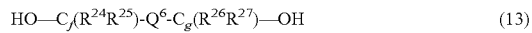

wherein $R^{24}$ to $R^{27}$ independently represent a hydrogen atom, an optionally substituted hydrocarbon group or an optionally substituted heterocyclic group; $Q^6$ represents a spacer or a direct link; and f and g have the same meanings as defined above; provided that $R^{24}$ and $R^{25}$ and $C_f$, and/or $R^{26}$ and $R^{27}$ and $C_g$ may be combined to form a ring; and $R^{24}$ or $R^{25}$ and $C_f$ and $Q^6$ and $C_g$ and $R^{26}$ or $R^{27}$ may be combined to form a ring such as an aliphatic ring and an aromatic ring.

In the formula (13), the optionally substituted hydrocarbon group and the optionally substituted heterocyclic group represented by $R^{24}$ to $R^{27}$ may be the same respective groups as described above. The spacer represented by $Q^6$ may be the same spacer as described above as $Q^1$ and $Q^2$.

Specific examples of the optically active diol compound include, for example, optically active diol compounds shown below:

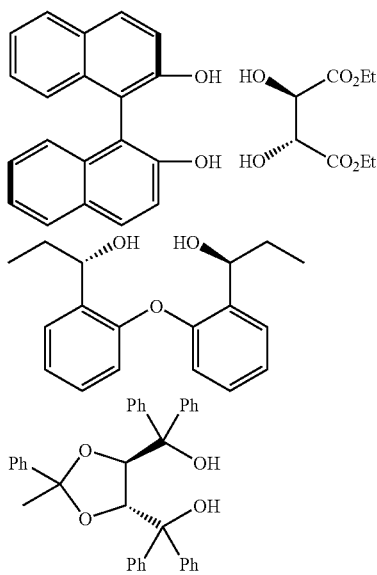

These optically active diol compounds include (1R,2R), (1S,2S), (1R,2S) and (1S,2R) as the optically active form, and these optically active diol compounds are particularly preferably the (1R,2R) and (1S,2S) form.

The bidentate optically active aminophosphine compound may be an aminophosphine compound having an optically active site in its molecule to form an optically active compound, and includes, for example, an optically active aminophosphine compound represented by the following formula (14). The optically active aminophosphine compound represented by the following formula (14) is an aminophosphine compound having an optically active site in its molecule.

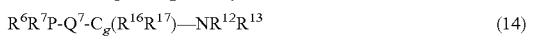

$$R^6R^7P-Q^7-C_g(R^{16}R^{17})-NR^{12}R^{13} \quad (14)$$

wherein $Q^7$ represents a spacer or a direct link; and $R^6$, $R^7$, $R^{12}$, $R^{13}$, $R^{16}$ and $R^{17}$ and g have the same meanings as defined above; provided that $R^6$ and $R^7$ and P, $R^6$ and/or $R^7$ and P and $Q^7$, $R^{16}$ and $R^{17}$ and $C_g$, $R^{12}$ or $R^{13}$ and $R^{16}$ or $R^{17}$ and $C_g$, and/or $R^{12}$ and $R^{13}$ and N may be combined to form a ring; $R^{12}$ and $R^{13}$ and N may be combined to form a heterocyclic ring such as a pyridine ring and the like; and $R^{16}$ or $R^{17}$ may be combined to form ring such as an aromatic ring and an aliphatic ring.

In the formula (13), the spacer represented by $Q^7$ may also be the same spacer as explained in the above-mentioned $Q^1$ and $Q^2$.

Specific examples of the optically active aminophosphine compound include, for example, optically active compounds shown below:

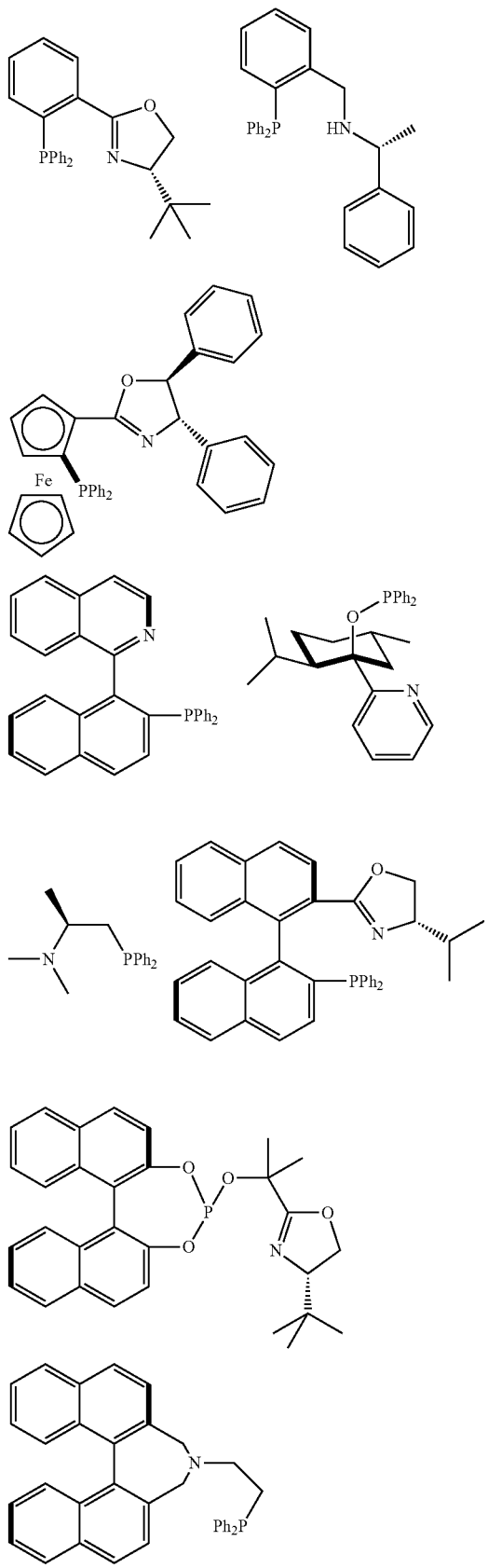

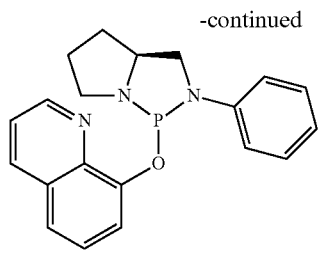

The bidentate optically active phosphinoalcohol compound may be a phosphinoalcohol compound having an optically active site in its molecule to form an optically active compound, and includes, for example, optically active phosphinoalcohol compounds represented by the following formula (15). The optically active phosphinoalcohol compound represented by the following formula (15) is a phosphinoalcohol compound having an optically active site in its molecule.

$$R^6R^7P-Q^8-C_g(R^{26}R^{27})-OH \quad (15)$$

wherein $Q^8$ represents a spacer or a direct link; and $R^6$, $R^7$, $R^{26}$ and $R^{27}$ and g have the same meanings as defined above; provided that $R^6$ and $R^7$ and P, $R^{26}$ and/or $R^{27}$ and $C_g$ and $Q^8$, $R^{26}$ and $R^{27}$ and $C_g$, $R^2$ or $R^{27}$ and $C_g$ and $Q^8$ may be combined to form a ring.

In the formula (15), the spacer represented by $Q^8$ may also be the same spacer as explained in the above-mentioned $Q^1$ and $Q^2$.

Specific examples of the optically active phosphinoalcohol compound include, for example, optically active compounds shown below:

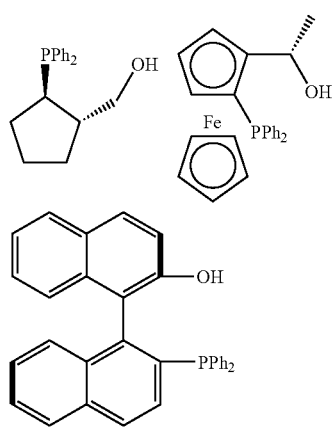

The bidentate optically active aminothio compound may be an aminothio compound having an optically active site in its molecule to form an optically active compound, and includes, for example, an optically active aminothio compound represented by the following formula (16). The optically active aminothio compound represented by the following formula (16) is an aminothio compound having an optically active site in its molecule.

$$R^{18}R^{19}N-C_f(R^{20}R^{21})-Q^9-C_g(R^{22}R^{23})-SR^{28} \quad (16)$$

wherein $R^{28}$ represents a hydrogen atom, an optionally substituted hydrocarbon group or an optionally substituted heterocyclic group; $Q^9$ represents a spacer or a direct link; and $R^{18}$, $R^{19}$, $R^{20}$ to $R^{23}$ and f and g have the same meanings as defined above; provided that $R^{20}$ and $R^{21}$ and $C_f$, and/or $R^{22}$ and $R^{23}$ and $C_g$ may be combined to form a ring; $R^{18}$ or $R^{19}$ and $R^{20}$ or $R^{21}$ and N and $C_f$ may be combined to form a ring; $R^{18}$ and $R^{19}$ and N may be combined to form a ring such as a heterocycle such as a pyridine ring and a piperidine ring; and $R^{20}$ or $R^{21}$ and $C_f$ and $Q^9$ and $C_g$ and $R^{22}$ or $R^{23}$ may be combined to form a ring such as an aromatic ring and an aliphatic ring.

In the formula (16), the optionally substituted hydrocarbon group and the optionally substituted heterocyclic group represented by $R^{28}$ may be the same respective groups as described above. The spacer represented by $Q^9$ may also be the same spacer as explained in the above-mentioned $Q^1$ and $Q^2$.

Specific examples of the optically active aminothio compound include, for example, compounds shown below:

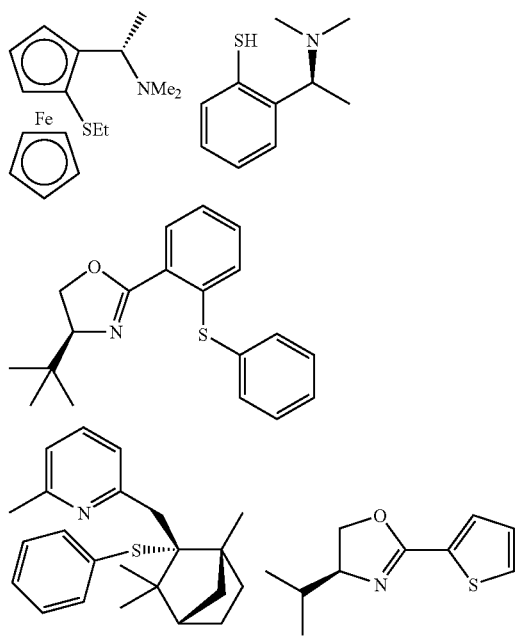

The tridentate ligand includes, for example, compounds shown below:

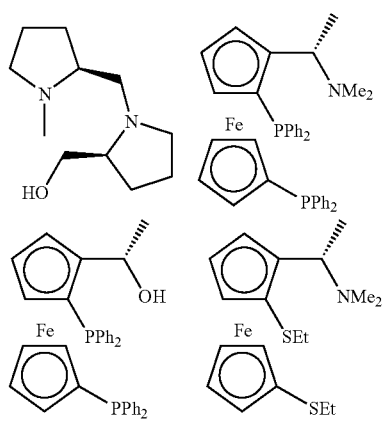

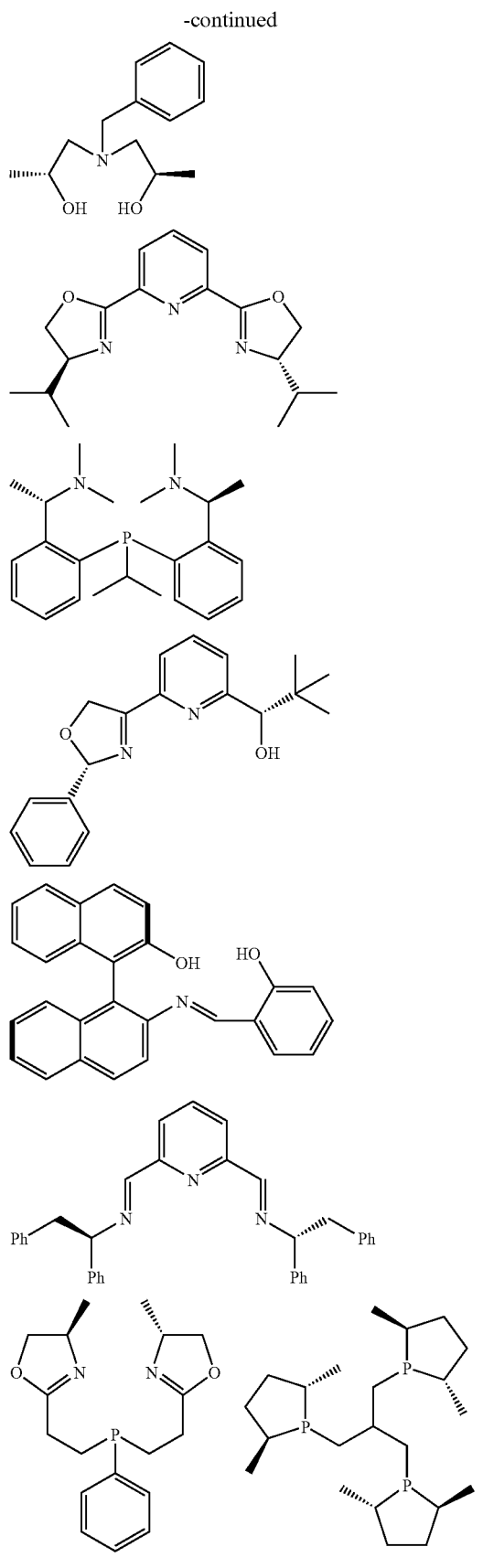
The tetradentate ligand includes, for example, compounds shown below:
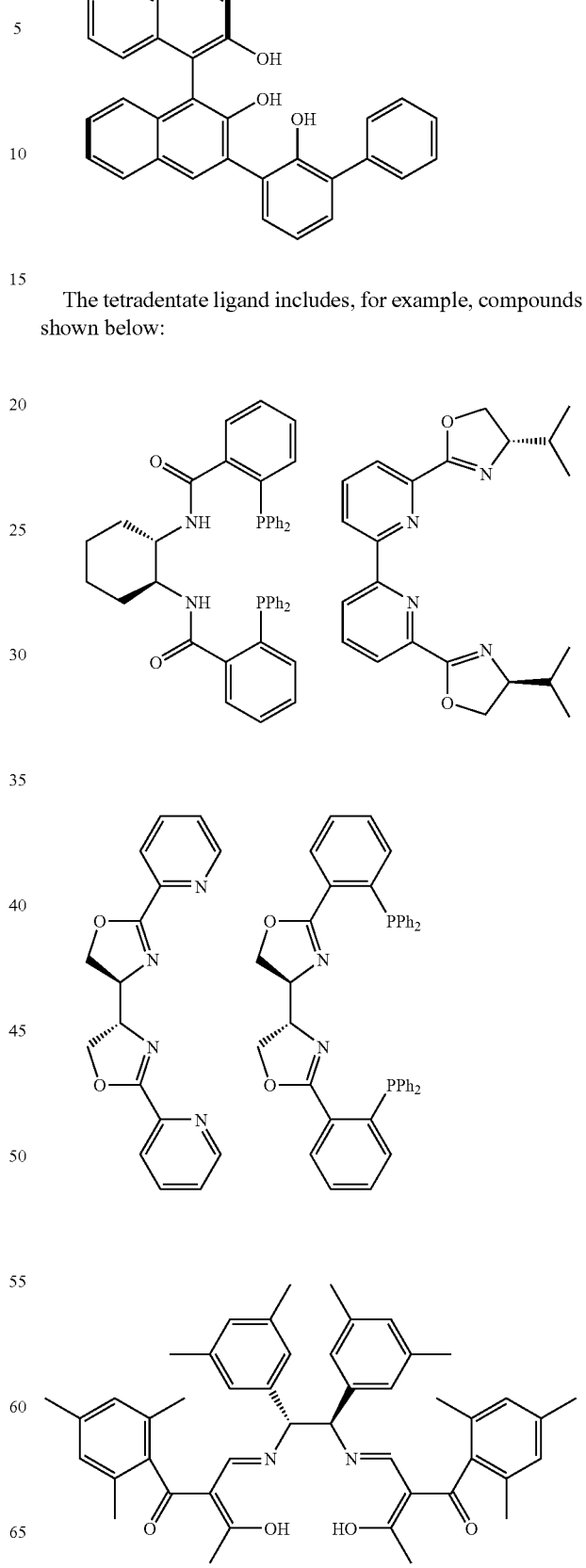

-continued

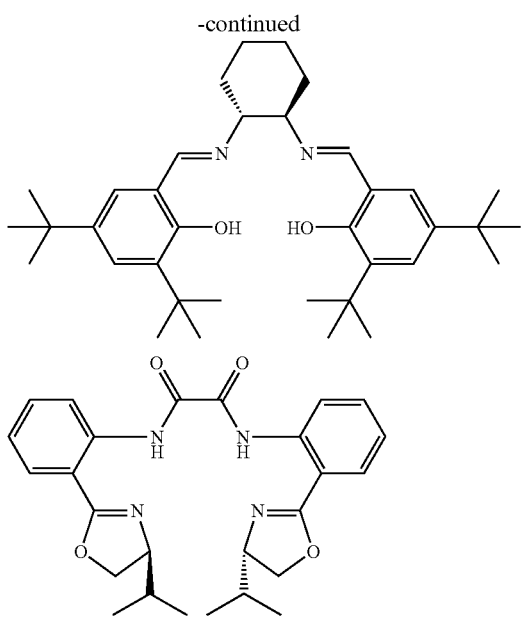

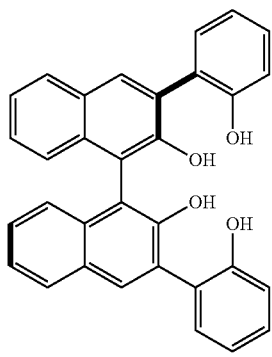

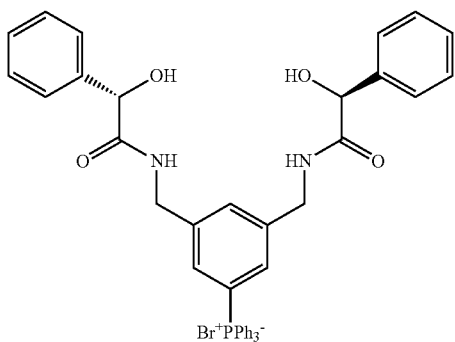

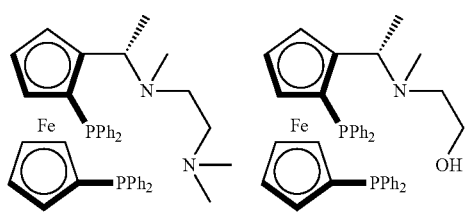

-continued

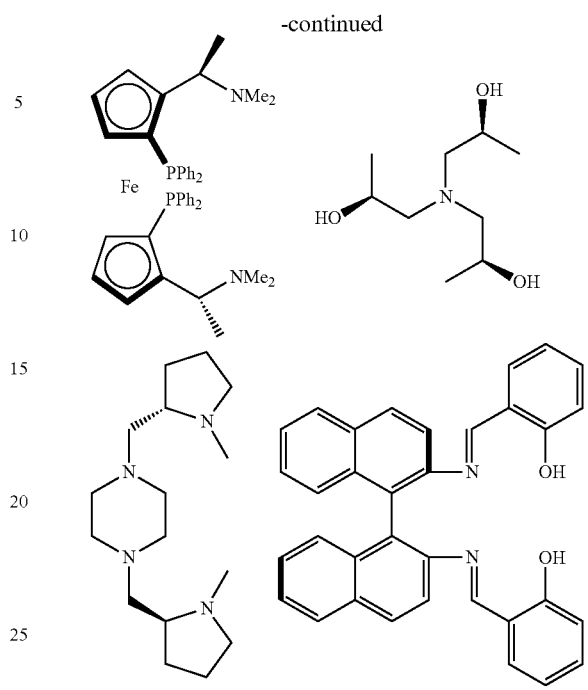

Provided that, the above-mentioned chiral ligand used in the present invention may be acted as a ligand in a different coordinated state depending on reaction conditions and the like.

The above-mentioned chiral ligand may be used alone or in a suitable combination of two or more thereof. These chiral ligands may also be combined arbitrarily with said ligand to form a chiral ligand.

Further, the chiral ligand may be either a commercial product or a chiral ligand produced properly by a conventional method or a method described in literatures described above and the like.

2) Copper Compound

The copper compound used in the present invention may be any copper compound which can be reacted with a chiral ligand to give a chiral copper complex, and which does not have a harmful effect in homogeneous hydrogenation when the obtained chiral copper complex is used as the catalyst for homogeneous hydrogenation.

The copper compound used in the present invention includes a monovalent or divalent copper-containing compound, and includes, for example, copper salt, other copper compound, copper complex and the like. Specific examples of these copper compounds used in the present invention include, for example, copper compounds described in Organocopper Reagent A Practical Approach (OXFORD UNIVERSITY PRESS, 1994), and the like.

The copper salt includes, for example, a copper salt represented by the following formula (2-1):

$$[Cu_{n11}X^1{}_{n21}]_{n13} \qquad (2\text{-}1)$$

wherein $X^1$s whose number is n12 may be the same or different and each represent an anion; and n11 to n13 independently represent a natural number.

The anion represented by $X^1$ includes nitrate ion, nitrite ion, halide ion, sulfate ion, sulfite ion, sulfonate ion, sulfamate ion, carbonate ion, hydroxide ion, carboxylate ion, sulfide ion, thiocyanate ion, phosphate ion, pyrophosphate ion, oxide ion, phosphide ion, chlorate ion, perchlorate ion, iodate ion, hexafluorosilicate ion, cyanide ion, borate ion, metaborate ion, borofluoride ion and the like.

The halide ion includes fluoride ion, chloride ion, bromide ion, iodide ion and the like.

The sulfonate ion includes a group represented by $R^{105}SO_3^-$ (wherein $R^{105}$ represents an optionally substituted hydrocarbon group, and the optionally substituted hydrocarbon group is the same as described above) and the like. Specific examples of the sulfonate ion include, for example, methanesulfonate ion, benzenesulfonate ion, trifluoromethanesulfonate ion, p-toluenesulfonate ion and the like.

The carboxylate ion includes a group represented by $R^{106}COO^-$ (wherein $R^{106}$ represents an optionally substituted hydrocarbon group, and the optionally substituted hydrocarbon group is the same as described above.) and the like. Specific examples of the carboxylate ion include, for example, acetate ion, formate ion, propionate ion, gluconate ion, oleate ion, oxalate ion, benzoate ion, phthalate ion, trifluoroacetate ion and the like.

The n11 and n12 independently represent a natural number, preferably a natural number of 1 to 10.

Specific examples of the copper salt include, for example, copper nitrate such as copper(I) nitrate and copper(II) nitrate; copper nitrite such as copper(I) nitrite and copper(II) nitrite; copper halide such as copper(I) chloride, copper(II) chloride, copper(I) bromide, copper(II) bromide, copper(I) fluoride, copper(II) fluoride, copper(I) iodide and copper(II) iodide; copper sulfate such as copper(II) sulfate; copper sulfite such as copper(II) sulfite; copper sulfonate such as copper(I) methanesulfonate, copper (II) methanesulfonate, copper (I) p-toluenesulfonate, copper(II) p-toluenesulfonate, copper(I) trifluoromethanesulfonate and copper (II) trifluoromethanesulfonate; copper sulfamate such as copper (II) sulfamate; copper carbonate such as copper(II) carbonate; copper hydroxide such as copper(II) hydroxide; copper carboxylate such as copper(I) acetate, copper(II) acetate, copper(II) formate, copper(II) propionate, copper(II) gluconate, copper(II) oleate, copper(II) oxalate, copper(II) benzoate, copper(II) phthalate, copper(II) caprylate, copper(II) citrate, copper(II) salicylate, copper(II) tartrate, copper(II) stearate, copper naphthenate, copper(II) lactate and copper(II) laurate; copper sulfide such as copper(I) sulfide and copper(II) sulfide; copper thiocyanate such as copper(I) thiocyanate and copper (II) thiocyanate; copper phosphate such as copper(II) phosphate and copper(II) pyrophosphate; copper oxide such as copper(I) oxide and copper(II) oxide; copper perhalate such as copper(I) chlorate and copper(II) perchlorate; copper halide such as copper(II) iodate; copper silicate such as copper hexafluorosilicate; copper cyanide such as copper(I) cyanide and copper(II) cyanide; and copper borate such as copper borate, copper metaborate and copper tetrafluoroborate; and the like.

Said other copper compound includes, for example, a copper compound represented by the following formula (2-2):

wherein $X^2$s whose number is n15 may be the same or different and represent an optionally substituted hydrocarbon group, $OR^{101}$ (wherein $R^{101}$ represents an optionally substituted hydrocarbon group), $NR^{102}_2$ (wherein two $R^{102}$ may be the same or different and represent a hydrogen atom or an optionally substituted hydrocarbon group), $PR^{103}_2$ (wherein two $R^{103}$ s may be the same or different and represent an optionally substituted hydrocarbon group), $SR^{104}$ (wherein $R^{104}$ represents an optionally substituted hydrocarbon group) and a 1,3-dicarbonyl compound or an enolate or hydrido thereof; and n14 to n16 independently represent a natural number.

In the formula (2-2), n14 and n15 independently represent a natural number, preferably a natural number of 1 to 10.

The optionally substituted hydrocarbon group represented by $X^2$ and the optionally substituted hydrocarbon groups represented by $R^{101}$, $R^{102}$, $R^{103}$ and $R^{104}$ in $OR^{101}$, $NR^{102}_2$, $PR^{103}_2$ and $SR^{104}$ may be the same optionally substituted hydrocarbon group as described above.

Specific examples of $OR^{101}$ represented by $X^2$ include methoxy, ethoxy, n-propoxy, isopropoxy, n-butoxy, s-butoxy, tert-butoxy, phenoxy and the like.

Specific examples of $NR^{102}_2$ include dimethylamino, diethylamino, dicyclohexylamino, diphenylamino and the like.

Specific examples of $PR^{103}_2$ include dimethylphosphino, diethylphosphino, di(tert-butyl)phosphino, dicyclohexylphosphino, diphenylphosphino and the like.

Specific examples of $SR^{104}$ include SMe, SEt, SBu, SPh, $S(CH_3C_6H_5)$ and the like.

Specific examples of the 1,3-dicarbonyl compound or an enolate thereof include 2,5-pentanedione (acac), 1,1,1-trifluoro-2,5-pentanedione, 1,1,1,3,3,3-hexafluoropentanedione (hfac), benzoylacetone, methyl acetoacetate, ethyl acetoacetate and the like.

Specific examples of the copper compound represented by the formula (2-2) include, for example, copper alkoxide such as copper dimethoxide, copper diethoxide, copper diisopropoxide and copper tert-butoxide; copper phenoxide such as copper phenoxide; copper phosphide such as copper di(tert-butylphosphide), copper dicyclohexylphosphide and copper diphenylphosphide; copper amide such as copper dicyclohexylamide; copper thiolate such as copper butanethiolate and copper thiophenolate; copper 1,3-dicarbonyl compound or an enolate thereof such as copper-2,4-pentanedionate, copper benzoylacetonate, copper 1,3-diphenyl-1,3-propanedionate, copper ethylacetoacetate, copper trifluoropentanedionate and copper hexafluoropentanedionate; copper hydride; copper hydrocarbon such as mesityl copper and ethynyl copper; silylated copper such as trimethylsilylethynyl copper; and the like.

Also, other copper compound includes a copper compound represented by the following formula (2-3):

wherein three $R^{107}$s are the same or different and represent an optionally substituted hydrocarbon group; and n17 represents a natural number.

Specific examples of the copper compound represented by the formula (2-3) include, for example, hydrido(triphenylphosphine)copper(I) hexamer (Stryker's reagent) and the like.

Specific examples of the copper compound represented by the formula (2-3) include, for example, copper(I) hydride (triphenylphosphine) hexamer and the like.

The copper compound such as the above-mentioned copper salt and the above-mentioned other copper compound may form double salt with a salt of an alkali metal (for example, lithium, sodium, potassium, rubidium, caesium and the like) and an alkaline earth metal (for example, magnesium, calcium, strontium, barium and the like). Specific examples of the formed double salt include, for example, $KCuF_3$, $K_3[CuF_6]$, $CuCN.LiCl$, $Li_2CuCl_4$, $Li_2CuCl_3$, LiCuBr$_2$ and the like. These copper salts and the above-mentioned other copper compounds may be anhydride or hydrate.

The copper complex used as the copper compound include any of a copper complex that i) has a ligand other than the chiral ligand, and is reacted with the chiral ligand to form the chiral copper complex capable of using as the catalyst for homogeneous hydrogenation, particularly the catalyst for homogeneous asymmetric hydrogenation, ii) is a copper complex, together with the chiral ligand, capable of using as the catalyst for homogeneous hydrogenation, particularly the catalyst for homogeneous asymmetric hydrogenation, or iii) is used as the chiral copper complex precursor which is reacted with the chiral ligand to form the chiral copper complex. The above-mentioned copper complex includes, for example, copper complexes described in "Comprehensive Organometallic Chemistry II (Pergamon, 1995)", "Comprehensive Organometallic Chemistry (Pergamon, 1982)", "WO2005/016943", "The Forth Series of Experimental Chemistry (Jikken Kagaku Kouza 4$^{th}$ edition), Vol. 17 (Inorganic Complex/Chelate Complex) and Vol. 18 (Organometallic Complex) 1991, edited by The Chemical Society of Japan (Maruzen)", "Inorg. Chem., 1382 (1965)." and the like.

The copper complex used as the copper compound has a complicated structure, and therefore it is not necessarily appropriate to express in a general formula. If the copper complex is daringly expressed by a structural formula, the complexcanbe represented, for example, by the following formula (2-4):

$$[Cu_{n21}L^2_{n22}]_{n23}X^3_{n24} \tag{2-4}$$

wherein L$^2$s whose number is n22 may be the same or different and represent a ligand; X$^3$s whose number is n24 may be the same or different and represent an anion or cation; n21 to n23 independently represent a natural number; and n24 represents 0 or a natural number.

In the formula (2-4), the ligand represented by L$^2$ may be a compound bonded or coordinated to copper. The ligand includes, for example, a ligand such as monodentate, bidentate, tridentate, tetradentate and the like.

Specific examples of the ligand represented by the above-mentioned L$^2$ include, for example, a halogen atom, carbon monoxide (CO), nitriles, cyanides, a neutral ligand, hydrocarbon groups, a hydrido group, a phosphorus compound, an amine compound, a sulfur compound, an anion, an optionally substituted hydrocarbon group, OR$^{101}$ (R$^{101}$ is the same as defined above), NR$^{102}$$_2$ (R$^{102}$ is the same as defined above), PR$^{103}$$_2$ (R$^{103}$ is the same as defined above), SR$^{104}$ (R$^{104}$ is the same as defined above), a 1,3-dicarbonyl compound or an enolate thereof (the 1,3-dicarbonyl compound and an enolate thereof are the same as defined above) and the like.

The halogen atom includes fluorine, chlorine, bromine, iodine and the like.

The nitriles include, for example, nitriles represented by R$^{110}$CN (wherein R$^{110}$ represents an optionally substituted hydrocarbon group). The optionally substituted hydrocarbon group represented by R$^{110}$ is the same optionally substituted hydrocarbon group as described above. Specific examples of the nitriles include, for example, acetonitrile, benzonitrile and the like.

The cyanides include, for example, cyanides represented by R$^{111}$NC (wherein R$^{111}$ represents an optionally substituted hydrocarbon group). The optionally substituted hydrocarbon group represented by R$^{111}$ is the same optionally substituted hydrocarbon group as described above. Specific examples of the cyanides include, for example, methyl isocyanide, phenyl isocyanide and the like.

The neutral ligand includes, for example, an aromatic compound, hydrocarbons such as olefins and diolefins, other neutral ligands and the like. The aromatic compound includes benzene, p-cymene, 1,3,5-trimethylbenzene (mesitylene), hexamethylbenzene and the like. The olefins include ethylene, propylene, cyclooctene and the like. The olefins include butadiene, cyclooctadiene (cod) norbornadiene (nbd) and the like. Said other neutral ligands include, for example, N,N-dimethylformamide (DMF), acetone, chloroform and the like.

The hydrocarbon groups include cyclopentadienyl (Cp), tetramethylcyclopentadienyl and the like.

The phosphorus compound includes, for example, phosphorus compounds represented by the formula (41):

$$PR^{151}_3 \tag{41}$$

wherein three R$^{151}$s are the same or different and represent a hydrogen atom, an optionally substituted hydrocarbon group, an optionally substituted heterocyclic group, an optionally substituted alkoxy group, an optionally substituted aryloxy group, an optionally substituted aralkyloxy group, an amino group or a substituted amino group.

The optionally substituted hydrocarbon group, the optionally substituted heterocyclic group, the optionally substituted alkoxy group, the optionally substituted aryloxy group, the optionally substituted aralkyloxy group and the substituted amino group, represented by R$^{151}$, may be the same respective groups as described above.

In the formula (41), the optionally substituted hydrocarbon group, the optionally substituted heterocyclic group, the optionally substituted alkoxy group, the optionally substituted aryloxy group, the optionally substituted aralkyloxy group and the substituted amino group, represented by R$^{151}$ may be the same respective groups as described above. Also, two phosphorus compounds may be combined with each other to form a diphosphine compound, for example a diphosphine compound represented by the formula (42):

$$R^{151}_2P-Q^{21}-PR^{151}_2 \tag{42}$$

wherein Q$^{21}$ represents a spacer, and four R$^{15}$'s may be the same or different and have the same meaning as defined above.

In the formula (42), the spacer represented by Q$^{21}$ is a group derived from R$^{151}$ and may be the same alkylene group as described above.

Specific examples of the above-mentioned phosphorus compound include, for example, a phosphane compound such as triphenylphosphine, tritolylphosphine, trimethylphosphine, triethylphosphine, methyl diphenylphosphine, dimethyl phenylphosphine, diphenylphosphinomethane (dppm), diphenylphosphinoethane (dppe), diphenylphosphinopropane (dppp), diphenylphosphinobutane (dppb) and diphenylphosphinoferrocene (dppf); a phosphite compound such as trimethyl phosphite, triethyl phosphite and triphenyl phosphate; and the like.

The amine compound includes, for example, ammonia; aliphatic amines such as methylamine, ethylamine, n-propylamine, isopropylamine, n-butylamine, s-butylamine, tert-butylamine and cyclohexylamine; aromatic amines such as aniline and dimethylaniline; nitrogen-containing aromatic heterocycles such as pyridine (py) and dimethylaminopyridine, nitrogen-containing aliphatic heterocycles such as pyrrolidine and piperazine; diamines such as ethylene diamine (en), propylene diamine, triethylene diamine, tetramethylethylene diamine (TMEDA), bipyridine (bpy) and phenanthroline (phen); and the like.

The sulfur compound includes, for example, dimethyl sulfide, diethyl sulfide, dipropyl sulfide, dibutyl sulfide and the like.

The anion may be the same anion as $X^1$ described in the formula (2-1). The optionally substituted hydrocarbon group may also be the same optionally substituted hydrocarbon group as described above.

The anion represented by X includes, for example, halide ion, $BR^{112}_4$ (four $R^{112}$s may be the same or different and represent a hydrogen atom, an optionally substituted hydrocarbon group or a halogen atom), $ClO_4$, $BrO_3$, OTf, $NO_3$, $PF_6$, $SbF_6$, $AsF_6$, $I_3$, sulfate ion, and $CuR^{113}_2$ (two $R^{113}$s may be the same or different and represent a halogen atom or an optionally substituted hydrocarbon group). Herein, Tf represents a trifluoromethanesulfonyl group ($SO_2CF_3$). The halogen atom, the halide ion and the optionally substituted hydrocarbon group are the same respective groups as described above.

Specific examples of $BR^{112}_4$ include, for example, $BH_4$, $BPh_4$, $BF_4$ and the like.

Specific examples of $CuR^{113}_2$ wherein $R^{113}$ is the halogen atom include, for example, $CuCl_2$, $CuBr_2$, $CuI_2$, $CuF_2$ and the like. Specific examples of $CuR^{113}_2$ wherein $R^{113}$ is the optionally substituted hydrocarbon group include, for example, $CuMe_2$, $CuPh_2$, $Cu(Mes)_2$ and the like. Here, Mes represents a mesityl group.

The cation includes an alkali metal ion, an alkaline earth metal ion, an ammonium ion, a phosphonium ion and the like.

The alkali metal ion includes, for example, lithium ion, sodium ion, potassium ion, caesium ion and the like.

The alkaline earth metal ion includes, for example, magnesium ion, calcium ion, barium ion and the like.

The ammonium ion includes ammonium ion and a substituted ammonium ion. Specific examples of the substituted ammonium ion include, for example, methylammonium ion, dimethylammonium ion, trimethylammonium ion, tetramethylammonium ion, ethylammonium ion, diethylammonium ion, triethylammonium ion, tetraethylammonium ion, tetrabutylammonium ion, tetraphenylammonium ion and the like.

The phosphonium ion includes phenylphosphonium ion, diphenylphosphonium ion, triphenylphosphonium ion, tetraphenylphosphonium ion and the like.

n21 represents a natural number, preferably a natural number of 1 to 10. n22 represents a natural number, preferably a natural number of 1 to 20.

Specific examples of the copper complex used as the above-mentioned copper compound include, for example, the following copper compounds as an example:

CuBr—$SMe_2$, $CuI.SMe_2$, $CuBr.P(OMe)_3$, $CuI.P(OMe)_3$, $CuI.P(OEt)_3$, $CuI.PBu_3$, CuO-tert-Bu.$PEt_3$, $CuI.PPh_3$, CuBr.$(SBu_2)_2$, $CuI.(SBU_2)_2$, $CuBr.[P(OMe)_3]_2$, $CuI.[P(OMe)_3]_2$, CuI.TMEDA, CuCl(cod), CuBr(cod), CuI(cod), $[Cu(BF_4)(PPh_3)_3]$, $[CuBr(PPh_3)]_n$, $Cu(PEt_3)Cp$, $Cu(PPh_3)CpCu(cod)$ (hfac), $Cu(C_2Me_2)(hfac)$, $[Cu(en)_2](ClO_4)_2$, $[Cu(en)_2]SO_4$, $[CuI(py)]$, $[CuI(MeNC)]$, $[Cu(MeCN)_4][BF_4]$, $[Cu(MeCN)_4][ClO_4]$, $[Cu(bpy)_2][BF_4]$, $[Cu(bpy)_2][ClO_4]$, $[Cu(phen)_2][ClO_4]$, $[Cu(cod)]_2[ClO_4]$, $[Cu(cod)]_2[OTf]$, $[Cu(cod)]_2[BF_4]$, $[Cu(cod)]_2[PF_6]$, $[Cu(CO)(en)][BPh_4]$, $[Cu(NH_3)_4]SO_4$, $[Cu(py)_4]ClO_4$, $[Cu(py)_6][ClO_4]_2$, $[Cu(NH_3)_6]Cl_2$, $[CuCl(PPh_3)_3]$, $[CuI(PEt_3)_3]$, $CuCl(C_8H_{12}N_2)$, $\{[Cu(CNMe)_2][CuI_2]\}_n$, $K_2[Cu(C_2O_4)_2]$, $(NH_4)_2[CuCl_4]$, $K_3[Cu(CN)_4]$, $K_3[Cu(NO_2)_5]$, $Li[CuMe_2]$, $Li[Cu(C_3H_5)(SPh)]$, and $Cu(NH_4)_2(SO_4)_2$.

These copper compounds described above, that is, copper compounds used as the copper compound such as the copper salt, said other copper compound, the copper complex may be anhydride or hydrate. These copper compounds may be used alone or in a suitable combination of two or more thereof.

The above-mentioned copper compound may be either a commercial product or a copper compound produced properly by a conventional method or a method described in literatures mentioned above in the present specification and the like.

3) Chiral Copper Complexes

Specific examples of the chiral copper complex used in the present invention include, for example, chiral copper complexes described in "Handbook of Enantioselective Catalysis (VCH, 1993)", "J. Am. Chem. Soc. 2001, 123, 5843", "J. Org. Chem. 1998, 63, 6090", "Angew. Chem. Int. Ed. 2004, 43, 1679", "Dalton. Trans. 2003, 1881", "ORGANIC LETTERS, Vol. 6, No. 14, 2305 (2004)" and the like. The chiral complexes shown below may also be included as specific examples of the chiral copper complex having the chiral ligand used in the present invention:

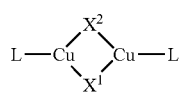

L: Bidentate ligand
BINAP, SEGPHOS, DM-SEGPHOS, DTBM-SEGPHOS, etc.
$X^1$, $X^2$: Cl, Br, I, F, OTf, OMe, O-t-Bu, H, etc.

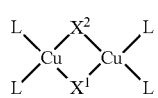

L: Monodentate ligand CAMP, MonoPHOS, etc
$X^1$, $X^2$: Cl, Br, I, F, OTf, OMe, O-t-Bu, H, etc.

L—CuH

L: Bidentate ligand
BINAP, SEGPHOS, DM-SEGPHOS, DTBM-SEGPHOS, etc.

[L—CuH]$_n$

L: Monodentate ligand CAMP, MonoPHOS, etc n: Natural number

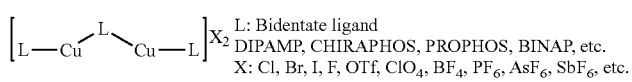

L: Bidentate ligand
DIPAMP, CHIRAPHOS, PROPHOS, BINAP, etc.
X: Cl, Br, I, F, OTf, $ClO_4$, $BF_4$, $PF_6$, $AsF_6$, $SbF_6$, etc.

| | |
|---|---|
| [L—Cu—L] X | L: Bidentate ligand<br>BINAP, SEGPHOS, DM-SEGPHOS, DTBM-SEGPHOS, etc.<br>X: Cl, Br, I, F, OTf, ClO$_4$, BF$_4$, PF$_6$, AsF$_6$, SbF$_6$, etc. |
| [L—Cu—L$^2$] X | L: Bidentate ligand<br>BINAP, SEGPHOS, DM-SEGPHOS, DTBM-SEGPHOS, etc.<br>L$^2$: cod, nbd, etc.<br>X: Cl, Br, I, F, OTf, ClO$_4$, BF$_4$, PF$_6$, AsF$_6$, SbF$_6$, etc. |
| 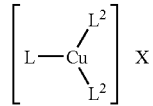 | L: Bidentate ligand<br>BINAP, SEGPHOS, DM-SEGPHOS, DTBM-SEGPHOS, etc.<br>L$^2$: MeCN, CO, H$_2$O, NH$_3$, etc.<br>X: Cl, Br, I, F, OTf, ClO$_4$, BF$_4$, PF$_6$, AsF$_6$, SbF$_6$, etc. |
| 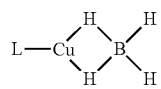 | L: Bidentate ligand<br>BINAP, SEGPHOS, DM-SEGPHOS, DTBM-SEGPHOS, etc. |
| 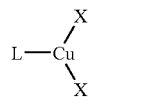 | L: Bidentate ligand<br>DPEN, DAIPEN, BINAP, SEGPHOS, etc.<br>X: Cl, Br, I, F, OTf, ClO$_4$, BF$_4$, PF$_6$, AsF$_6$, SbF$_6$, etc. |
| L—Cu | L: Tetradentate ligand<br>TROST LIGAND, Jacobsen Ligand, etc. |
| [L—Cu] X | L: Tetradentate ligand<br>TROST LIGAND, Jacobsen Ligand, etc.<br>X: Cl, Br, I, F, OTf, ClO$_4$, BF$_4$, PF$_6$, AsF$_6$, SbF$_6$, etc. |

These chiral copper complexes may be used alone or, if necessary, in a suitable combination of two or more thereof. The chiral copper complex having the chiral ligand may also be anhydride or hydrate. The chiral copper complex used in the present invention may be either a commercial product or a chiral copper complex produced properly by a conventional method, a method described in literatures mentioned above or a method described later and the like.

The chiral copper complex used in the present invention may be any chiral copper complex having the chiral ligand as explained in "1) Chiral ligand" mentioned above. The chiral copper complex has a complicated structure, and therefore it is not necessarily appropriate to express in a general formula. If the copper complex is daringly expressed by a structural formula, the complex can be represented, for example, by the following formula (1):

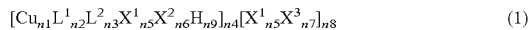  (1)

wherein L$^1$s whose number is n2 may be the same or different and each represent a chiral ligand; L$^2$S whose number is n3 may be the same or different and represent a ligand; X$^1$s whose number is n5 may be the same or different and represent an anion; X$^2$s whose number is n6 may be the same or different and represent an optionally substituted hydrocarbon group, OR$^{101}$ (wherein R$^{101}$ represents an optionally substituted hydrocarbon group), NR$^{102}_2$ (wherein two R$^{102}$S may be the same or different and represent an optionally substituted hydrocarbon group), PR$^{103}_2$ (wherein two R$^{103}$s may be the same or different and represent an optionally substituted hydrocarbon group), SR$^{104}$ (wherein R$^{104}$ represents an optionally substituted hydrocarbon group) or a 1,3-dicarbonyl compound or an enolate or hydride thereof; X$^3$s whose number is n7 may be the same or different and represent an anion or a cation; n1, n2 and n4 independently represent a natural number; n3 and n6 to n9 independently represent 0 or a natural number; and two n5s may be the same or different and represent 0 or a natural number.

In the formula (1), the chiral ligand represented by L$^1$ is the chiral ligand as explained in "1) Chiral ligand" mentioned above. The ligand represented by L$^2$, the anion represented by X$^1$, the optionally substituted hydrocarbon group, OR$^{101}$, NR$^{102}_2$, PR$^{103}_2$, SR$^{104}$ and the 1,3-dicarbonyl compound or the enolate thereof represented by X$^2$, and the anion and the cation represented by X$^3$ may be the same as described above, respectively.

The n1 represents a natural number, preferably a natural number of 1 to 10. Then 2 represents a natural number, preferably a natural number of 1 to 12. The n3 represents 0 or a natural number, preferably 0 or a natural number of 1 to 20. The n5 represents a natural number, preferably a natural number of 1 to 10. The n6 represents 0 or a natural number, preferably 0 or a natural number of 1 to 10.

The above-mentioned chiral copper complex represented by the formula (1) includes, for example, a chiral copper complex represented by the formula (61):

  (61)

wherein L$^{11}$ represents a bidentate optically active phosphorus compound; L$^{12}$ represents a phosphorus compound different from L$^{11}$; L$^{13}$ represents a ligand; and n35 represents a natural number.

In the formula (61), the bidentate optically active phosphorus compound represented by L$^{11}$ may be the same optically active phosphorus compound as explained in the above-mentioned Chiral ligand. The bidentate optically active phosphorus compound represented by L$^{11}$ is particularly preferably an optically active diphosphine compound. The above-mentioned optically active diphosphine compound may be the same optically active phosphorus compound as explained in the above-mentioned Chiral ligand. The phosphorus compound different from L$^{11}$, represented by L$^{12}$, may be any phosphorus compound different from the bidentate optically active phosphorus compound represented by L$^{11}$, or may be an optically active form (a chiral ligand) or a non-chiral ligand, and, for example, may be the same optically active phosphorus compound as explained in the above-mentioned Chiral ligand or the phosphorus compound as explained in the ligand represented by $L^2$ in the above-mentioned formula (2-4) in the present specification. The ligand represented by $L^{13}$ may be the same ligand as explained in the ligand represented by $L^2$ in the above-mentioned formula (2-4).

Specific examples of the chiral copper complex represented by the formula (61) include, for example, [CuF(PPh$_3$)(L$^{20}$)]$_n$, [CuCl(PPh$_3$)(L$^{20}$)]$_n$, [CuBr(PPh$_3$)(L$^{20}$)]$_n$, [CuI(PPh$_3$)(L$^{20}$)]$_n$, [CuH(PPh$_3$)(L$^{20}$)]$_n$, [CuOTf(PPh$_3$)(L$^{20}$)]$_n$, [Cu(NO$_3$)(PPh$_3$)(L$^{20}$)]$_n$, [Cu(OAc)(PPh$_3$)(L$^{20}$)]$_n$, [CuCl(P(3,5-xylyl)$_3$)(L$^{20}$)]$_n$ and the like;

wherein $L^{20}$ represents the same optically active diphosphine compound as that of $L^{11}$: ((R)-BINAP, (S)-BINAP, (R)-DM-BINAP, (S)-DM-BINAP, (R)-SEGPHOS, (S)-SEGPHOS, (R)-DM-SEGPHOS, (S)-DM-SEGPHOS, (R)-DTBM-SEGPHOS, (S)-DTBM-SEGPHOS, (R,R)-SKEWPHOS, (S,S)-Me-DuPHOS, (S,S)-Me-DuPHOS, (R,S)-Josiphos, (S,R)-Josiphos and the like); and n represents a natural number.

The chiral copper complex used in the present invention may be, for example, produced based on a method described in the literatures in the present specification and the like.

That is, the chiral copper complex can be easily obtained by reacting the chiral ligand with the copper compound, in a suitable solvent if necessary.

The amount of the chiral ligand and the copper compound used are not particularly limited because it varies depending on the kind of the copper compound and the chiral ligand used and the like. The amount of the chiral ligand used is suitably selected usually in the range of 0.000001 to 100 equivalents, preferably 0.00001 to 10 equivalents relative to the copper compound.

The solvent used as necessary includes, for example, aliphatic hydrocarbons such as pentane, hexane, heptane, octane, decane and cyclohexane; aromatic hydrocarbons such as benzene, toluene and xylene; halogenated hydrocarbons such as dichloromethane, 1,2-dichloroethane, chloroform, carbon tetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane and 1,3-dioxolane; alcohols such as methanol, ethanol, 2-propanol, n-butanol, s-butanol, tert-butanol, 2-ethoxyethanol and benzyl alcohol; ketones such as acetone, methyl ethyl ketone, methyl isobutyl ketone and cyclohexanone; esters such as methyl acetate, ethyl acetate, n-butyl acetate and methylpropionate; amides such as formamide, N,N-dimethylformamide and N,N-dimethylacetamide; sulfoxides such as dimethyl sulfoxide; cyano-containing organic compounds such as acetonitrile; N-methylpyrrolidone; water and the like. These solvents may be used alone or in a suitable combination of two or more thereof.

The amount of the solvent used is suitably selected usually in the range of 1 to 1000 times by volume, preferably 5 to 200 times by volume relative to the copper compound.

The reaction of the chiral ligand and the copper compound may be carried out in the presence of other reagent, if necessary.

Said other reagent includes an acid, a base, a reducing agent, a halogenating agent and the like.

The acid includes an inorganic acid, an organic acid, a Lewis acid and the like.

The inorganic acid includes, for example, hydrochloric acid, hydrobromic acid, sulfuric acid, phosphoric acid, tetrafluoroboric acid, perchloric acid, periodic acid and the like.

The organic acid includes, for example, carboxylic acid such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid and glycolic acid; sulfonic acid such as methanesulfonic acid, benzenesulfonic acid, p-toluenesulfonic acid and trifluoromethanesulfonic acid; and the like.

The Lewis acid includes, for example, aluminum halide such as aluminum chloride and aluminum bromide; dialkylaluminum halide such as diethylaluminum chloride, diethylaluminum bromide and diisopropylaluminum chloride; trialkoxy aluminum such as triethoxy aluminum, triisopropoxy aluminum, and tri-tert-butoxy aluminum; titanium halides such as titanium tetrachloride; tetraalkoxy titanium such as tetraisopropoxy titanium; boron halide such as boron trifluoride, boron trichloride, boron tribromide and boron trifluoride-diethyl ether complex; zinc halide such as zinc chloride and zinc bromide; and the like.

The base includes an inorganic base, an organic base and the like. The inorganic base includes, for example, alkali metal hydroxides such as lithium hydroxide, sodium hydroxide and potassium hydroxide; metal carbonates such as sodium carbonate, potassium carbonate, magnesium carbonate and calcium carbonate; metal hydrogen carbonates such as sodium hydrogen carbonate and potassium hydrogen carbonate; metal hydrides such as lithium hydride, sodium hydride and potassium hydride; ammonia, and the like. The organic base includes, for example, alkali metal-alkaline earth metal salts such as lithium methoxide, lithium ethoxide, lithium-tert-butoxide, sodium methoxide, sodium ethoxide, sodium tert-butoxide, potassium methoxide, potassium ethoxide, potassium tert-butoxide, potassium naphthalenide, sodium acetate, potassium acetate, magnesium acetate, calcium acetate, lithium diethylamide, lithium diisopropylamide, lithium bis(trimethylsilyl)amide, sodium bis(trimethylsilyl)amide, potassium bis(trimethylsilyl)amide, lithium diphenylphosphide, sodium diphenylphosphide and potassium diphenylphosphide; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organometallic compounds such as methyl lithium, ethyl lithium, n-propyl lithium, isopropyl lithium, n-butyl lithium, s-butyl lithium, tert-butyl lithium, phenyl lithium, methyl magnesium chloride, ethyl magnesium chloride, n-propyl magnesium chloride, isopropyl magnesium chloride, n-butyl magnesium chloride, s-butyl magnesium chloride, tert-butyl magnesium chloride, phenyl magnesium chloride, methyl magnesium bromide, ethyl magnesium bromide, n-propyl magnesium bromide, isopropyl magnesium bromide, n-butyl magnesium bromide, s-butyl magnesium bromide, tert-butyl magnesium bromide and phenyl magnesium bromide; the optically active forms of the diamine compounds exemplified above as the chiral ligand (the optically active diamine compound) and racemic form thereof; and the like.

The reducing agent includes, for example, lithium aluminum hydride, sodium borohydride and the like.

The halogenating agent includes, for example, a quaternary ammonium salt such as tetrabutylammonium fluoride, tetrabutylammonium bromide and tetrabutylammonium triphenyl difluorosilicate; a halogen such as iodine and bromine; and the like.

These other reagents may be used alone or in a suitable combination of two or more thereof.

The amount of said other reagents used is suitably selected usually in the range of 0.001 to 100 equivalents, preferably 0.01 to 100 equivalents relative to the copper compound.

The reaction temperature of the chiral ligand with the copper compound varies depending on the kind of the solvent and the like. The temperature is suitably selected usually in the range of −100° C. to 150° C., preferably −80° C. to 120° C.

The reaction time is suitably selected usually in the range of 1 minute to 100 hours, preferably 10 minutes to 24 hours.

After the reaction, the obtained chiral copper complex may be used as it stands without post-treatment and the like and as the catalyst for homogeneous hydrogenation, particularly the catalyst for homogeneous asymmetric hydrogenation, or may be used as said catalyst after carrying out with post-treatment, purification, isolation and the like, if necessary. Specific a method of the post-treatment include separation and purification of a method known per se, such as solvent extraction, salting out, crystallization, recrystallization, various kinds of chromatography and the like.

There are some cases where thus obtained chiral copper complex may be a mixture of so-called monomer and(or) polymer. That is, there are some cases where thus obtained chiral copper complex may be mixed with the chiral copper complexes of the above-mentioned formula (1) wherein n4 is 1 (monomers) and the chiral copper complexes of the above-mentioned formula (1) wherein n4 is 2 or more (polymers).

[1-2] Catalyst for Homogeneous Hydrogenation

The catalyst for homogeneous hydrogenation containing the chiral copper complex and the catalyst for homogeneous hydrogenation containing the mixture of the chiral ligand and the copper compound of the present invention may be a solid or liquid state, and may be added other components to said catalyst. Said other components added as necessary may be any components which does not have a harmful effect in homogeneous hydrogenation, and include, for example, the solvent, said other reagents and the like mentioned above.

In the catalyst for homogeneous hydrogenation containing the mixture of the chiral ligand and the copper compound of the present invention, a mixing ratio of the chiral ligand and the copper compound may be suitably selected such that the copper compound is usually used in the range of 0.000001 to 10 equivalents, preferably 0.0001 to 1 equivalent relative to the chiral ligand.

[2] Process for Producing a Hydrogenated Compound of an unsaturated Compound

The process for producing a hydrogenated compound of an unsaturated compound of the present invention can be carried out by hydrogenation of an unsaturated compound as a starting material (substrate) in a homogeneous system in the presence of the catalyst for homogeneous hydrogenation to give a desired hydrogenated compound of the unsaturated compound, which is easily and with a good yield. Here, when a prochiral compound is used as the unsaturated compound and the catalyst for homogeneous asymmetric hydrogenation is used as the catalyst for homogenous hydrogenation, the resulting hydrogenated compound of the unsaturated compound can be obtained as an optically active compound thereof.

In the production process of the present invention, the homogeneous hydrogenation may be carried out in the presence of the above-mentioned copper complex or may be carried out by mixing the chiral ligand and the copper compound with the unsaturated compound.

Also, the production process of the present invention may be carried out by further adding the catalyst for homogeneous hydrogenation containing the copper complex having the chiral ligand, the catalyst for homogeneous hydrogenation containing the mixture of the chiral ligand and the copper compound, the chiral ligand and/or the copper compound, if necessary, to the reaction system (the reaction mixture).

1) Unsaturated Compound

The unsaturated compound used in the present invention includes, for example, an unsaturated compound such as an alkene, a ketone, an imine, a ketocarboxylic acid, a ketoalkene and the like.

The alkene is preferably a prochiral alkene and includes, for example, an alkene represented by the following formula (21):

(21)

The ketone is preferably a prochiral ketone and includes, for example, a ketone represented by the following formula (22)

(22)

The imine is preferably a prochiral imine and includes, for example, an imine represented by the following formula (23)

(23)

The ketocarboxylic acid is preferably a prochiral ketocarboxylic acid and include, for example, a ketocarboxylic acid represented by the following formula (24):

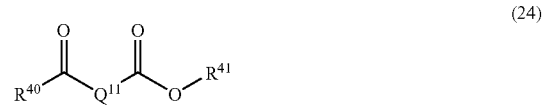

(24)

The ketoalkene is preferably a prochiral ketoalkene and include, for example, a ketoalkene represented by the following formula (25):

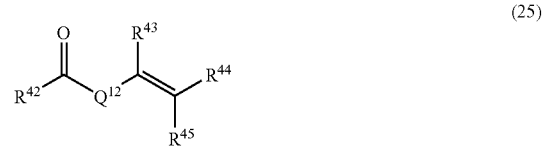

(25)

In the above-mentioned formulae (21) to (25), the groups represented by $R^{31}$ to $R^{45}$ may be such groups that the respective compounds can exist and include, for example, the groups suitably selected from a hydrogen atom, an optionally substituted hydrocarbon group, an optionally substituted heterocyclic group, a halogen atom, a halogenated hydrocarbon group, an optionally substituted alkoxy group, an optionally substituted aryloxy group, an optionally substituted aralkyloxy group, an optionally substituted heteroaryloxy group, an optionally substituted alkylthio group, an optionally substituted arylthio group, an optionally substituted aralkylthio group, an optionally substituted heteroarylthio group, an optionally substituted acyl group, an optionally substituted acyloxy group, an optionally substituted alkoxycarbonyl group, an optionally substituted aryloxycarbonyl group, an optionally substituted aralkyloxycarbonyl group, an optionally substituted alkylenedioxy group, a nitro group, an amino group, a substituted amino group, a cyano group, a sulfo group, a substituted silyl group, a substituted silyloxy group, a hydroxy group, a carboxy group, an optionally substituted alkoxythiocarbonyl group, an optionally substituted aryloxythiocarbonyl group, an optionally substituted aralkyloxythiocarbonyl group, an optionally substituted alkylthiocarbonyl group, an optionally substituted arylthiocarbonyl group, an optionally substituted aralkylthiocarbonyl group, an optionally substituted carbamoyl group, a substituted phosphino group, an aminosulfonyl group, an alkoxysulfonyl group and the like. In the formulae (24) and (25), $Q^{11}$ and $Q^{12}$ represent a spacer or a direct link. Provided that, $R^{31}$ and $R^{32}$, $R^{31}$ and $R^{33}$, $R^{31}$ and $R^{34}$, $R^{32}$ and $R^{33}$, $R^{32}$ and $R^{34}$, $R^{33}$ and $R^{34}$, $R^{35}$ and $R^{36}$, $R^{38}$ and $R^{39}$, $R^{38}$ or $R^{39}$ and $R^{37}$, $R^{40}$ and $Q^{11}$, $R^{40}$ and $R^{41}$, $R^{41}$ and $Q^{11}$, $R^{42}$ and $Q^{12}$, $R^{44}$ and $Q^{12}$, $R^{2}$ and $R^{43}$, $R^{42}$ and $R^{44}$ or $R^{45}$, $R^{43}$ and $R^{44}$, $R^{43}$ and $R^{45}$, or $R^{44}$ and $R^{45}$ may be combined with each other to form a ring. Said formed ring includes, for example, the ring(s) formed by bonding through an alkylene group or an alkylenedioxy group. Provided that, these formed rings may have further substituents.

In the above-mentioned formulae (21) to (25), the respective groups represented by $R^{31}$ to $R^{45}$ and the alkylene or alkylenedioxy group when the ring(s) is/are formed may be the same respective groups as explained in the above-mentioned [1] and the respective groups as explained in the substituent, or respective groups described later unless otherwise specified (The same applies hereinafter). The spacer represented by $Q^{11}$ and $Q^{12}$ may also the same spacer as explained in the above-mentioned [1].

Also, in the formula (24), the group represented by $R^{41}$ may be a metal atom such as an alkali metal and the like. The above-mentioned carboxy group and sulfo group may also form a metal salt of a metal atom such as an alkali metal and the like. The alkali metal includes lithium, sodium, potassium, rubidium, caesium and the like.

In the formulae (21) to (25) when the respective groups of $R^{31}$ to $R^{45}$ forms ring(s), that is, for example, when $R^{31}$ and $R^{32}$, $R^{31}$ and $R^{33}$, $R^{32}$ and $R^{34}$, $R^{33}$ and $R^{34}$, $R^{35}$ and $R^{36}$, $R^{38}$ and $R^{39}$, $R^{38}$ or $R^{39}$ and $R^{37}$, $R^{40}$ and $Q^{11}$, $R^{40}$ and $R^{41}$, $R^{41}$ and $Q^{11}$, $R^{42}$ and $Q^{12}$, $R^{42}$ and $R^{43}$, $R^{43}$ and $R^{42}$ or $R^{45}$, $R^{43}$ and $R^{44}$, or $R^{44}$ and $R^{45}$ are combined with each other to form a ring, the formed ring include, for example, a ring formed by bonding through a carbon chain such as the optionally substituted alkylene group, the optionally substituted alkylenedioxy group and the like. The formed ring may be a monocyclic, polycyclic or fused ring and includes, for example, an aliphatic ring, an aromatic ring, and the like, such as a 4- to 8-membered ring and the like.

The optionally substituted alkylene group includes an alkylene group and a substituted alkylene group. The alkylene group may be linear or branched and includes, for example, an alkylene group having 1 to 10 carbon atom(s). Specific examples of the alkylene group include, for example, methylene, ethylene, propylene, trimethylene, tetramethylene, pentamethylene, hexamethylene, heptamethylene, octamethylene, nonamethylene, decamethylene, 2-methylpropylene, 2,2-dimethylpropylene, 2-ethylpropylene and the like. A carbon chain of the forming ring may contain an oxygen atom, a sulfur atom, an imino group, a substituted imino group, a carbonyl group (C=O), a thiocarbonyl group (C=S) and the like. When the ring is formed, specific examples of the ring include a cyclopentane ring, a cyclohexane ring, for example a 5- to 7-membered lactone ring, for example, a 5- to 7-membered lactam ring, cyclopentanone ring and cyclohexanone ring. These formed rings may be rings that a carbon atom at a moiety to be asymmetrically hydrogenated can become an asymmetric carbon atom by homogeneous asymmetric hydrogenation. A substituent on the substituted imino group is the same substituent as described above.

The substituted alkylene group (an alkylene group having a substituent) includes an alkylene group wherein at least one hydrogen atom of the above-mentioned alkylene group is substituted with a substituent.

The optionally substituted alkylenedioxy group includes an alkylenedioxy group and a substituted alkylenedioxy group. The alkylenedioxy group includes, for example, an alkylenedioxy group having 1 to 3 carbon atom(s). Specific examples of the alkylenedioxy group include, for example, methylenedioxy, ethylenedioxy, trimethylenedioxy, propylenedioxy and the like.

The substituted alkylenedioxy group (an alkylenedioxy group having a substituent) includes an alkylenedioxy group wherein at least one hydrogen atom of the above-mentioned alkylenedioxy group is substituted with a substituent. Specific examples of the substituted alkylenedioxy group include difluoromethylenedioxy and the like.

The spacer includes an optionally substituted divalent organic group such as an alkylene group, an arylene group, a heteroarylene group and the like. The above-mentioned divalent organic group may have at least one heteroatom or heteroatomic group such as an oxygen atom, a carbonyl group, a sulfur atom, an imino group, a substituted imino group and the like in an arbitrary position of at the terminal position or in the chain of said organic group. A substituent on the substituted imino group is the same a substituent as described later.

The alkylene group includes, for example, an alkylene group having 1 to 10 carbon atom(s). Specific examples of the alkylene group include, for example, methylene, ethylene, trimethylene, propylene, tetramethylene, pentamethylene, hexamethylene, heptamethylene, octamethylene, nonamethylene, decamethylene and the like.

The arylene group includes, for example, an arylene group having 6 to 20 carbon atoms. Specific examples of the arylene group include, for example, phenylene, biphenyldiyl, binaphthalenediyl, bisbenzodioxolediyl and the like.

The heteroarylene group includes, for example, a heteroarylene group having 2 to 20 carbon atoms and a 3- to 8-membered, preferably 5- to 6-membered monocyclic, polycyclic or fused ring heteroarylene group containing at least 1, preferably 1 to 3 heteroatom(s) such as a nitrogen atom, an oxygen atom and/or a sulfur atom. Specific examples of the heteroarylene group include, for example, bipyridinediyl, bisbenzothioldiyl, bisthioldiyl and the like.

The divalent organic group having the heteroatom or the heteroatomic group includes —$CH_2$—O—$CH_2$—, —$C_6H_4$—O—$C_6H_4$— and the like.

These divalent organic groups may be substituted with the substituent as explained in the above-mentioned [1].

In the formula (24), the group represented by $R^{41}$ may be a metal atom such as an alkali metal and the like. The carboxy group and the sulfo group may also form a metal salt of a metal atom such as an alkali metal and the like. The alkali metal includes lithium, sodium, potassium, rubidium, caesium and the like.

These unsaturated compounds are particularly preferably prochiral compounds. Provided that, when the unsaturated compound is the prochiral compound, the groups represented by $R^{31}$ to $R^{45}$ in the above-mentioned formulae (21) to (25) may be such groups that the resulting hydrogenated compound of the prochiral compound is capable of forming the optically active compound.

Specific examples of the alkene of the unsaturated compounds used in the present invention include, for example, alkenes shown below:

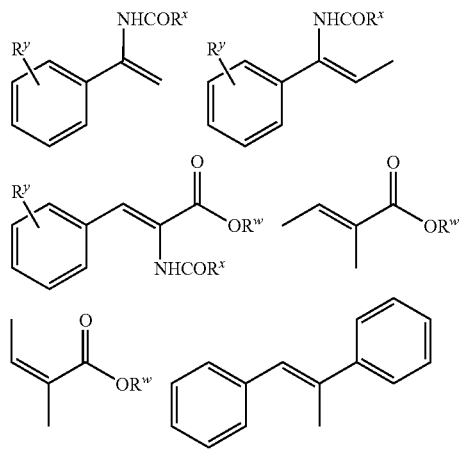

$R^w$: H, CH$_3$, C$_2$H$_5$, $^i$Pr, n-C$_4$H$_9$, Na, K, etc.
$R^x$: CH$_3$, C$_2$H$_5$, $^i$Pr, n-C$_4$H$_9$, etc.
$R^y$: H, 2-CH$_3$, 3-CH$_3$, 4-CH$_3$, 2-CH$_3$O, 3-CH$_3$O, 4-CH$_3$O, 2-$^t$Bu, 3-$^t$Bu, 4-$^t$Bu, 2-CN, 3-CN, 4-CN, 2-Cl, 3-Cl, 4-Cl, 2-Br, 3-Br, 4-Br, etc.

Specific examples of the ketone include, for example, methyl ethyl ketone, acetophenone, 1-indanone, 3,4-dihydro-(2H)-naphthalenone ferrocenyl methyl ketone and the like, and include, for example, ketones shown below:

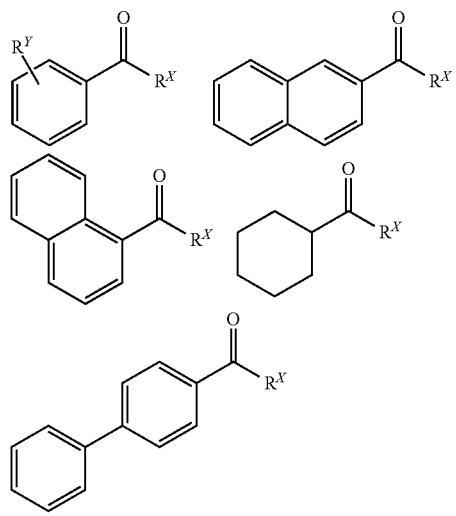

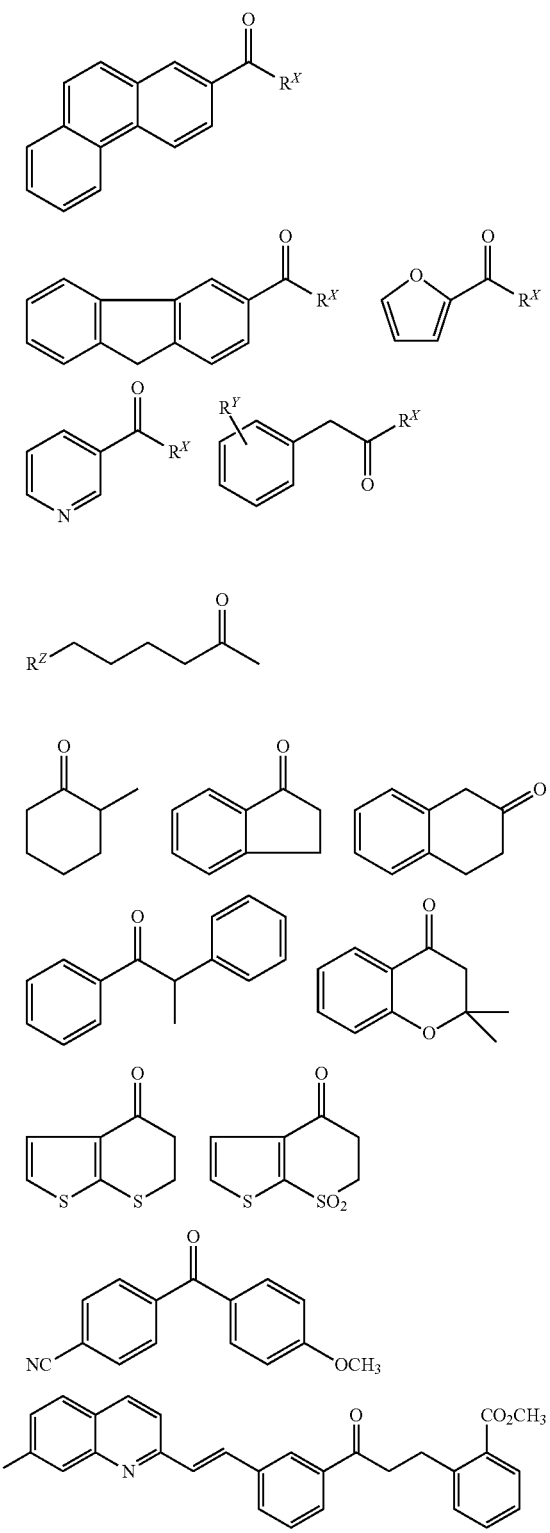

$R^x$: CH$_3$, C$_2$H$_5$, $^i$Pr, n-C$_4$H$_9$, etc.
$R^y$: H, 2-CH$_3$, 3-CH$_3$, 4-CH$_3$, 2-CH$_3$O, 3-CH$_3$O, 4-CH$_3$O, 2-$^t$Bu, 3-$^t$Bu, 4-$^t$Bu, 2-CN, 3-CN, 4-CN, 2-Cl, 3-Cl, 4-Cl, 2-Br, 3-Br, 4-Br, etc.
$R^z$: CH$_3$, C$_2$H$_5$, C$_3$H$_7$, $^i$Pr, n-C$_4$H$_9$, etc.

Specific examples of the imine include, for example, imines shown below:

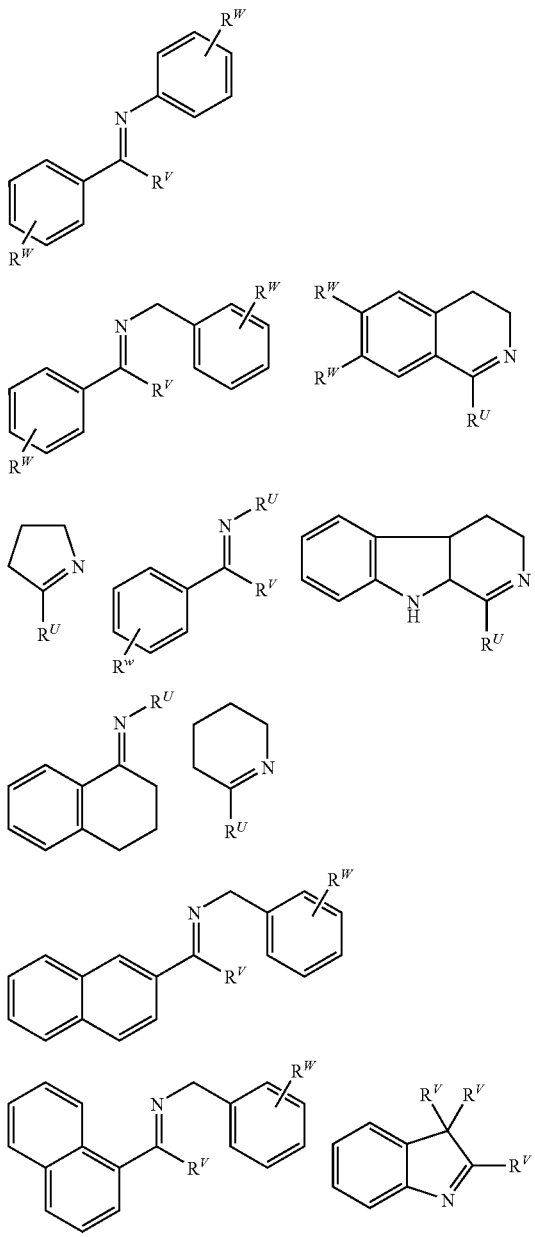

$R^U$: CH$_3$, C$_2$H$_5$, Pr, $^i$Pr, Bu, $^t$Bu, C$_6$H$_5$, CH$_2$C$_6$H$_5$, C$_6$H$_4$CH$_3$, C$_6$H$_4$OCH$_3$, OH, etc.
$R^V$: CH$_3$, C$_2$H$_5$, Pr, $^i$Pr, Bu, $^t$Bu, etc.
$R^W$: H, CH$_3$, CH$_3$O, C$_2$H$_5$O, Bu, $^t$Bu, Cl, Br, C$_6$H$_5$, etc.

Specific examples of the ketocarboxylic acid include, for example, ketocarboxylic acids shown below:

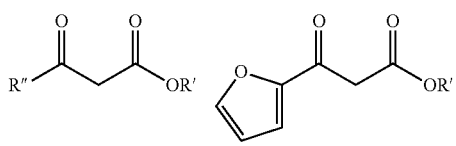

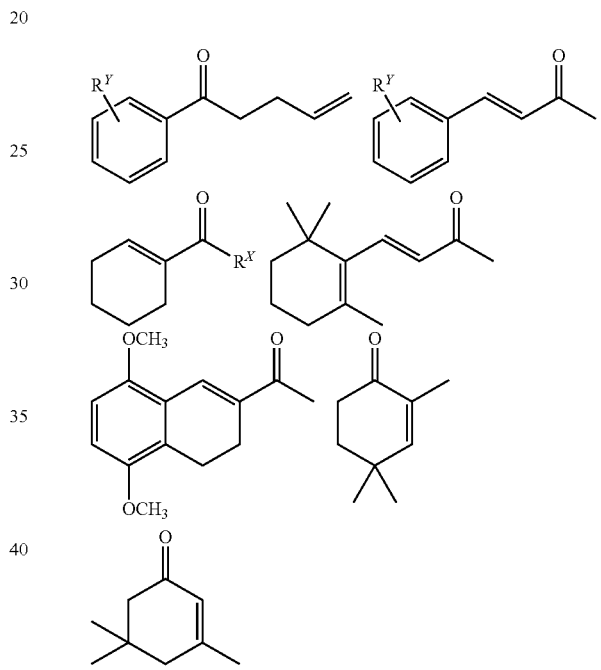

n = 2~5
R' : Me, Et etc.
R'' : Me, Et, $^i$Pr, ——CH$_2$CH(CH$_3$)$_2$ etc.

Specific examples of the ketoalkene include, for example, ketoalkenes shown below:

$R^X$: CH$_3$, C$_2$H$_5$, $^i$Pr, n-C$_4$H$_9$, etc.
$R^Y$: H, 2-CH$_3$, 3-CH$_3$, 4-CH$_3$, 2-CH$_3$O, 3-CH$_3$O, 4-CH$_3$O, 2-$^t$Bu, 3-$^t$Bu, 4-$^t$Bu, 2-CN, 3-CN, 4-CN, 2-Cl, 3-Cl, 4-Cl, 2-Br, 3-Br, 4-Br, etc.

Provided that, the above-mentioned unsaturated compound may further have a chiral center in a molecule thereof in addition to a moiety forming itself prochiral.

2) Homogeneous hydrogenation (Homogeneous asymmetric hydrogenation)

In the present invention, the homogeneous hydrogenation (homogenous hydrogenation method) is carried out in the presence of a hydrogen source. The hydrogen source includes hydrogen gas and a hydrogen donor. That is, the homogeneous hydrogenation in the present invention is a homogeneous hydrogenation carried out in the presence of hydrogen gas (preferably a homogeneous asymmetric hydrogenation) or a homogeneous transfer hydrogenation carried out in the presence of the hydrogen donor (preferably a homogeneous asymmetric transfer hydrogenation).

The amount of the catalyst for homogeneous hydrogenation used is not particularly limited. When the catalyst for homogeneous hydrogenation containing the chiral copper complex is used, the amount of the chiral copper complex used is suitably selected in the range of 0.00001 to 1 equivalent, preferably 0.0001 to 0.1 equivalents relative to the unsaturated compound. Also, when the catalyst for homogeneous hydrogenation containing the mixture of the chiral ligand and the copper compound is used, the amount of the copper compound used is suitably selected in the range of 0.00001 to 1 equivalent, preferably 0.0001 to 0.1 equivalents relative to the unsaturated compound.

A pressure of the hydrogen gas, in the case of in which the production process of the present invention is carried out in the presence of the hydrogen gas by the homogeneous hydrogenation, preferably the homogeneous asymmetric hydrogenation is sufficient in such a condition of hydrogen atmosphere or the pressure of 0.1 MPa or less. The pressure, in consideration of economically, operativity and the like, is suitably selected usually in the range of 0.1 to 20 MPa, preferably 0.2 to 10 MPa. Further, it is possible to maintain a high activity even at 1 MPa or less in consideration of economic efficiency.

The hydrogen donor includes, for example, formic acid or formates, a combination of formic acid and a base, hydroquinone, cyclohexadiene, phosphorous acid, an alcohol and the like. These compounds are particularly preferably formic acid or formates, a combination of formic acid and a base, the alcohol and the like.

The formates in formic acid and formates include a metal salt of formic acid such as an alkali metal formate and an alkaline earth metal formate, an ammonium salt, a substituted amine salt and the like.

Formic acid in the combination of formic acid and the base may be such formic acid as to form a formate or to substantially form a formate in a reaction system.

The base forming the metal formates such as alkali metal formates and alkaline earth metal formate, ammonium salt, the substituted amine salt; and the base in a combination of formic acid and a base, include ammonia, an inorganic base, an organic base and the like.

The alkali metal forming formates include lithium, sodium, potassium, rubidium, caesium and the like. The alkaline earth metals include magnesium, calcium, strontium, barium and the like.

The inorganic base includes, for example, the alkali metal salt or an alkaline earth metal salt such as potassium carbonate, potassium hydroxide, lithium hydroxide, sodium hydrogen carbonate, sodium carbonate, potassium hydrogen carbonate, sodium hydroxide, magnesium carbonate and calcium carbonate; metal hydrides such as sodium hydride; and the like.

The organic base includes, for example, alkali metal alkoxides such as potassium methoxide, sodium methoxide, lithium methoxide, sodium ethoxide, potassium isopropoxide, lithium tert-butoxide, sodium tert-butoxide and potassium tert-butoxide, alkali metal acetates or alkaline earth metal acetates such as sodium acetate, potassium acetate, magnesium acetate and calcium acetate; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organometallic compounds such as methyl magnesium bromide, ethyl magnesium bromide, propyl magnesium bromide, tert-butyl magnesium chloride, tert-butyl magnesium bromide, methyl lithium, ethyl lithium, propyl lithium, n-butyl lithium and tert-butyl lithium; and the like.

The alcohol as the hydrogen donor is preferably lower alcohols having a hydrogen atom at the α-position, and specific examples include, for example, methanol, ethanol, n-propanol, isopropanol, n-butanol, sec-butanol and the like. The alcohol as the hydrogen donor is particularly preferably propanol.

The amount of the hydrogen donor used is suitably selected usually in the range of 0.1 to 10000 equivalents, preferably 0.5 to 2000 equivalents, relative to the unsaturated compound.

The homogeneous hydrogenation in the present invention, that is, the process for producing a hydrogenated compound of an unsaturated compound, can be carried out in a solvent if necessary. The solvent includes, for example, aromatic hydrocarbons such as benzene, toluene and xylene; aliphatic hydrocarbons such as pentane, hexane, heptane and octane; halogenated hydrocarbons such as dichloromethane, chloroform, carbon tetrachloride and dichloroethane; ethers such as diethyl ether, diisopropyl ether, tert-butyl methyl ether, cyclopentyl methyl ether, dimethoxyethane, tetrahydrofuran, dioxane and dioxolane; alcohols such as methanol, ethanol, 2-propanol, n-butanol, tert-butanol and benzyl alcohol; polyhydric alcohols such as ethylene glycol, propylene glycol, 1,2-propanediol and glycerin; amides such as N,N-dimethylformamide and N,N-dimethylacetamide; ketones such as acetone and methyl isobutyl ketone; esters such as methyl acetate, ethyl acetate and butyl acetate; acetonitrile; N-methylpyrrolidone; dimethyl sulfoxide; water and the like. These solvents may be used alone or in a suitable combination of two or more thereof.

The amount of the solvent used is not particularly limited and varies depending on economical efficiency and the kind and solubility of the unsaturated compound used as a reaction substrate, and is suitably selected usually for example in a ratio of 0 to 200, preferably 0 to 40, relative to the reaction substrate. For example, when an alcohol is used as the solvent, the reaction can be carried out in the solvent at a low concentration of 1% or less or in a solvent-free or nearly solvent-free state, depending on the unsaturated compound used.

The reaction temperature is not particularly limited and varies depending on the kind and amount of the asymmetric catalyst and the kind of the unsaturated compound, and is suitably selected usually in the range of −30 to 250° C., preferably 0 to 100° C., in consideration of economical efficiency. For example, the reaction can be carried out even at a low temperature of −30 to 0° C. or at a high temperature of 100 to 250° C.

The reaction time varies depending on the kind and amount of the asymmetric catalyst used, the kind and concentration of the unsaturated compound used, and reaction conditions such as reaction temperature and hydrogen pressure, and is suitably selected usually in the range of 1 minute to 48 hours, preferably 10 minutes to 24 hours.

The homogeneous hydrogenation in the present invention can be carried out regardless of whether the reaction form is batch-wise or continuous. The reaction can be carried out in reaction containers known in the art, such as a flask, a reactor, an autoclave and the like.

The homogeneous hydrogenation can be carried out if necessary in the presence of an additive. The additive include an acid, a fluorine-containing alcohol, a base, a quaternary ammonium salt, a quaternary phosphonium salt, a phosphorus compound, a halogen, a reducing agent, water and the like.

The acid as the additive includes an inorganic acid, an organic acid, Lewis acid and the like.

The inorganic acid includes, for example, hydrochloric acid, hydrobromic acid, sulfuric acid, phosphoric acid, tetrafluoroboric acid, perchloric acid, periodic acid and the like.

The organic acid includes, for example, carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid and glycolic acid; sulfonic acids such as methanesulfonic acid, benzenesulfonic acid, p-toluenesulfonic acid and trifluoromethanesulfonic acid; and the like.

Lewis acid includes, for example, aluminum halides such as aluminum chloride and aluminum bromide; dialkylaluminum halides such as diethylaluminum chloride, diethylaluminum bromide and diisopropylaluminum chloride; trialkoxy aluminum such as triethoxy aluminum, triisopropoxy aluminum, and tri-tert-butoxy aluminum; titanium halides such as titanium tetrachloride; tetraalkoxy titanium such as tetraisopropoxy titanium; boron halides such as boron trifluoride, boron trichloride, boron tribromide, and a boron trifluoride-diethyl ether complex; zinc halides such as zinc chloride and zinc bromide; and the like.

These acids may be used alone or in a suitable combination of two or more thereof.

The amount of the acid used is suitably selected usually in the range of 0.0001 to 100 equivalents, preferably 0.001 to 10 equivalents, relative to the unsaturated compound.

The fluorine-containing alcohol as the additive is preferably a fluorine-containing aliphatic alcohol. Specific examples of the fluorine-containing alcohol include a saturated or unsaturated fluorine-containing aliphatic alcohol having 1 to 10 carbon atoms. Specific examples of the fluorine-containing aliphatic alcohol include, for example, 2,2,2-trifluoroethanol, 2,2-difluoroethanool, 3,3,3-trifluoropropanol, 2,2,3,3,3-pentafluoropropanol, 2,2,3,3-tetrafluoropropanol, 3,3,4,4,4-pentafluorobutanol, 4,4,5,5,5-pentafluoropentanol, 5,5,6,6,6-pentafluorohexanol, 3,3,4,4,5,5,6,6,6-nonafluorohexanol, 1,1,1,3,3,3-hexafluoro-2-propanol and the like. These fluorine-containing aliphatic alcohols may be used alone or in a suitable combination of two or more thereof.

The amount of the fluorine-containing alcohol used is suitably selected usually in the range of 0.01 to 100 equivalents, preferably 0.1 to 10 equivalents, relative to the unsaturated compound.

The base as the additive includes an inorganic base, an organic base and the like. The inorganic base includes, for example, alkali metal hydroxides such as lithium hydroxide, sodium hydroxide and potassium hydroxide; metal carbonates such as sodium carbonate, potassium carbonate, magnesium carbonate and calcium carbonate; metal hydrogen carbonates such as sodium hydrogen carbonate and potassium hydrogen carbonate; metal hydrides such as lithium hydride, sodium hydride and potassium hydride; ammonia; and the like. The organic base includes, for example, alkali metal salts or alkaline earth metal salts such as lithium methoxide, lithium ethoxide, lithium tert-butoxide, sodium methoxide, sodium ethoxide, sodium tert-butoxide, potassium methoxide, potassium ethoxide, potassium tert-butoxide, potassium naphthalenide, sodium acetate, potassiumacetate, magnesiumacetate, calciumacetate, lithium diethylamide, lithium diisopropylamide, lithium bis(trimethylsilyl)amide, sodium bis(trimethylsilyl)amide, potassium bis(trimethylsilyl) amide, lithium diphenylphosphide, sodium diphenylphosphide and potassium diphenylphosphide; organic amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine; organometallic compounds such as methyl lithium, ethyl lithium, n-propyl lithium, isopropyl lithium, n-butyl lithium, s-butyl lithium, tert-butyl lithium, phenyl lithium, methyl magnesium chloride, ethyl magnesium chloride, n-propyl magnesium chloride, isopropyl magnesium chloride, n-butyl magnesium chloride, s-butyl magnesium chloride, tert-butyl magnesium chloride, phenyl magnesium chloride, methyl magnesium bromide, ethyl magnesium bromide, n-propyl magnesium bromide, isopropyl magnesium bromide, n-butyl magnesium bromide, s-butyl magnesium bromide, tert-butyl magnesium bromide and phenyl magnesium bromide; optically active forms (optically active diamine compounds) of the diamine compounds illustrated above as the chiral ligands and racemic compounds thereof; and the like.

The amount of the base used is suitably selected usually in the range of 0 to 100 equivalents, preferably 0 to 10 equivalents, relative to the unsaturated compound.

The quaternary ammonium salt as the additive includes, for example, a quaternary ammonium salt having 4 to 24 carbon atoms. Specific examples of the quaternary ammonium salt include tetrabutyl ammonium fluoride, tetrabutyl ammonium chloride, tetrabutyl ammonium bromide, tetrabutyl ammonium iodide, triethyl benzyl ammonium chloride, tetrabutyl ammonium triphenyl difluorosilicate and the like.

The amount of the quaternary ammonium salt used is suitably selected usually in the range of 0.0001 to 100 equivalents, preferably 0.001 to 10 equivalents, relative to the unsaturated compound.

The quaternary phosphonium salt includes, for example, C4 to C36 quaternary phosphonium salts. Specific examples of the quaternary phosphonium salt include tetraphenyl phosphonium chloride, tetraphenyl phosphonium bromide, tetraphenyl phosphonium iodide, methyl triphenyl phosphonium chloride, methyl triphenyl phosphonium bromide, methyl triphenyl phosphonium iodide and the like.

The amount of the quaternary phosphonium salt used is suitably selected usually in the range of 0.0001 to 100 equivalents, preferably 0.001 to 10 equivalents, relative to the unsaturated compound.

The phosphorus compound may be the same as the phosphorus compound represented by the above-mentioned formula (P).

Specific examples of the phosphorus compound include phosphine compounds such as triphenylphosphine, tritolylphosphine, trimethylphosphine, triethylphosphine, methyl diphenylphosphine, dimethyl phenylphosphine, diphenyl phosphinomethane (dppm), diphenyl phosphinoethane (dppe), diphenyl phosphinopropane (dppp), diphenyl phosphinobutane (dppb) and diphenyl phosphinoferrocene (dppf), and phosphite compounds such as trimethyl phosphite, triethyl phosphite, triphenyl phosphite and the like.

The amount of the phosphorus compound used is suitably selected usually in the range of 0.00001 to 1 equivalent, preferably 0.0001 to 1 equivalent, relative to the unsaturated compound.

The halogen includes bromine, iodine and the like.

The amount of the halogen used is suitably selected usually in the range of 0.0001 to 100 equivalents, preferably 0.001 to 10 equivalents, relative to the unsaturated compound.

The reducing agent includes, for example, sodium borohydride, lithium aluminum hydride, diisobutylaluminum hydride and the like.

The amount of the reducing agent used is suitably selected usually in the range of 0.00001 to 1 equivalent, preferably 0.0001 to 1 equivalent, relative to the unsaturated compound.

These additives may be used alone or in a suitable combination of two or more thereof.

The hydrogenated compound of the unsaturated compound, obtained by the production method of the present invention, is a compound obtained by carrying out homogeneous hydrogenation of said unsaturated compound, and preferably an optically active compound thereof is obtained. That is, in the present invention, the homogeneous hydrogenation is preferably a homogeneous asymmetric hydrogenation. Accordingly, the hydrogenated compound of the unsaturated compound obtained in the present invention is preferably an optically active compound, and an optically active compound corresponding to each unsaturated compound is obtained. For example, the compound obtained by hydrogenation of the alkene is an optically active alkane; the compound obtained by asymmetric hydrogenation of the ketone is an optically active alcohol; the compound obtained by hydrogenation of the imine is an optically active amine; the compound obtained by hydrogenation of the ketocarboxylic acid is an optically active hydroxyester; and the compound obtained by hydrogenation of the ketoalkene is a hydroxyalkene, a hydroxyalkane and/or a ketoalkane, respectively.

The optically active alkane obtained by asymmetric hydrogenation of the alkene includes, for example, an optically active alkane represented by the following formula (31):

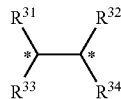

(31)

The optically active alcohol obtained by asymmetric hydrogenation of the ketone includes, for example, an optically active alcohol represented by the following formula (32):

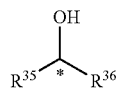

(32)

The optically active amine obtained by asymmetric hydrogenation of the imine includes, for example, an optically active amine represented by the following formula (33):

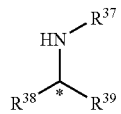

(33)

The optically active hydroxyester obtained by asymmetric hydrogenation of the ketocarboxylic acid includes, for example, an optically active hydroxyester represented by the following formula (34):

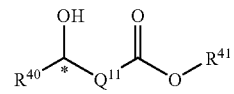

(34)

The optically active hydroxyalkene, the optically active hydroxyalkane and the optically active ketoalkane obtained by asymmetric hydrogenation of the ketoalkene are, for example, represented by the following formulae (35) to (37), respectively:

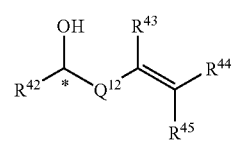

(35)

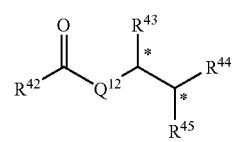

(36)

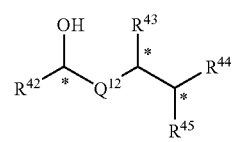

(37)

In the above formulae, the symbol * represents an asymmetric carbon atom; and $R^{31}$ to $R^{45}$, $Q^{11}$ and $Q^{12}$ are the same as described above. Provided that, the symbol * may not be an asymmetric carbon atom depending on the kind of $R^{31}$ to $R^{45}$ in the cases where $R^{35}$ is equal to $R^{36}$, or either $R^{35}$ or $R^{36}$ is a hydrogen atom in the formula (32) and the like.

Specific examples of the optically active compounds include optically active forms of the hydrogenated compounds of unsaturated compounds as exemplified by the above-mentioned hydrogenated compounds of unsaturated compounds as specific examples.

The resulting optically active compound may be subjected as necessary to post-treatment such as purification, isolation and the like, or to protection of functional group(s) and the like, followed by post-treatment such as purification, isolation and the like. Specific methods of post-treatment are the same methods as described above.

The catalyst for homogeneous hydrogenation of the present invention is not only obtained at a low price, but also improved workability because handled easily. The process for producing an optically active compound, using this catalyst for homogenous hydrogenation as the catalyst for homogenous asymmetric hydrogenation, becomes more able to control the asymmetric hydrogenation of an unsaturated compound, is able to give an intentional optically active compound, and is able to give a desired optically active compound that is a hydrogenated compound of an unsaturated compound with a high yield and a high optical purity, by changing the kind of the chiral ligand used.

Hydrogenated compounds of unsaturated compounds, particularly optically active compounds of the hydrogenated compounds, obtained according to the production process of the present invention are useful as intermediates of medicines and agrochemicals, perfumes and the like.

EXAMPLES

Hereinafter, the present invention will be described in more detail by way of the Examples, but the present invention is not limited thereto.

In the following Examples, instruments used for measurements of physical properties etc. are as follows:
NMR: DRX-500 manufactured by Bruker
Gas chromatography (GC): 5890-II manufactured by Hewlett Packard
Mass spectrometry: ESI-MS (LCMS-IT-TOF manufactured by Shimadzu Corporation), EI-MS (Poralis Q manufactured by Thermo Electron)

In the Examples below, the symbol "n" represents a natural number.

Example 1

Synthesis of [CuBr((S)-SEGPHOS)]$_n$

Into a reaction vessal was put 500 mg (0.819 mmol) of (S)-SEGPHOS and 176 mg (1.23 mmol, 1.5 equivalents) of copper(I) bromide (CuBr), followed by replacing with nitrogen in the vessal, and then 5 mL of toluene was added. The reaction was carried out with stirring at room temperature for 16 hours. The reaction solution was purified by column chromatography on silica gel, and then the solvent was distilled away, to give the title compound.
$^{31}$P-NMR (CDCl$_3$): δ; −8.1

Example 2

Synthesis of [CuCl((S)-SEGPHOS)]$_n$

Into a reaction vessal was put 1.0 g (1.64 mmol) of (S)-SEGPHOS and 2.44 mg (2.46 mmol, 1.5 equivalents) of copper (I) chloride (CuCl), followed by replacing with nitrogen in the vessal, and then 5 mL of toluene was added. The reaction was carried out with stirring at room temperature for 16 hours. The reaction solution was purified by column chromatography on silica gel, and then the solvent was distilled away, to give the title compound.
$^{31}$P-NMR (CDCl$_3$): δ; −7.0

Example 3

Synthesis of [CuI((S)-SEGPHOS)]$_n$

Into a reaction vessal was put 500 mg (0.819 mmol) of (S)-SEGPHOS and 234 mg (1.23 mmol, 1.5 equivalents) of copper(I) iodide (CuCl), followed by replacing with nitrogen in the vessal, and then 5 mL of toluene was added. The reaction was carried out with stirring at room temperature for 16 hours. The reaction solution was purified by column chromatography on silica gel, and then the solvent was distilled away, to give the title compound.
$^{31}$P-NMR (CDCl$_3$): δ; −9.2

Example 4

Synthesis of [Cu(OTf)((S)-SEGPHOS)]$_n$

Into a reaction vessal was put 500 mg (0.819 mmol) of (S)-SEGPHOS and 309 mg (1.23 mmol, 1.5 equivalents) of CuOTf.0.5C$_6$H$_6$, followed by replacing with nitrogen in the vessal, and then 5 mL of toluene was added. The reaction was carried out with stirring at room temperature for 16 hours. The reaction solution was filtered through Celite, and then the solvent was distilled away, to give the title compound.
$^{31}$P-NMR (CDCl$_3$): δ; −1.1
$^{19}$F-NMR (CDCl$_3$): δ; −77.4

Examples 5 to 8

Homogeneous Asymmetric Hydrogenation of Isophorone 1 Using Cu(I) Salt, Shown in the Following Scheme A Scheme A: Asymmetric hydrogenation of isophorone 1

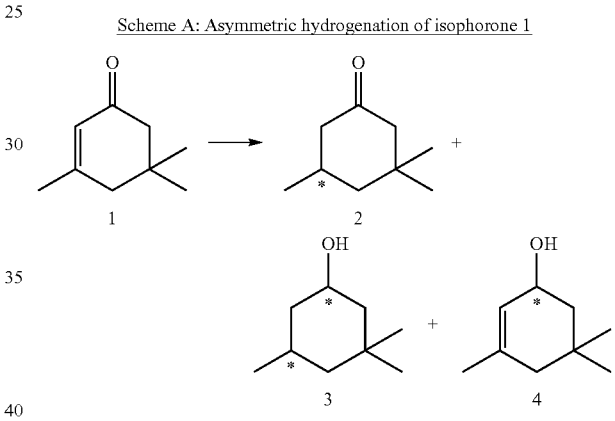

Into a 100-mL stainless-steel autoclave was put 0.03 mmol of the copper salt (CuX) shown in Table 1 below, 18.3 mg (0.03 mmol) of (S)-SEGPHOS and 28.8 mg (0.30 mmol) of sodium tert-butoxide (NaO-t-Bu), followed by replacing with nitrogen in the autoclave, and then 2 mL of a mixed solvent of toluene and tert-butyl alcohol (t-BuOH) by a ratio of 3:1, and isophorone 1 (0.15 mL, 1.0 mmol) were added. The reaction was carried out with stirring under a hydrogen pressure of 3.0 MPa at 50° C. for 16 to 17 hours. The reaction mixture was analyzed by using GC. The results are shown in Table 1.

TABLE 1

| | | | Yield (%) [Optical Purity (% ee)] | | |
|---|---|---|---|---|---|
| Example | CuX | Reaction Time (h) | 3,3,5-Trimethylcyclohexanone 2 | 3,3,5-Trimethylcyclohexanol 3 | 3,3,5-Trimethyl-2-cyclohexenol 4 |
| 5 | CuCl | 16 | 21[94] | 6 | trace |
| 6 | CuBr | 17 | 28[93] | 15 | trace |
| 7 | CuI | 17 | 12[88] | 1 | trace |
| 8 | CuOTf[c] | 17 | 26[93] | 11[96][b] (91/9)[a] | trace |

[a] dr (Diastereomer ratio)
[b] Optical purity (% ee) of main diastereomer
[c] Cu(OTf)•0.5C$_6$H$_6$

Examples 9 to 11

Homogeneous Asymmetric Hydrogenation Using Cu(II) Salt Shown in the Above Scheme A Into a 100-mL stainless-steel autoclave was put 0.03 mmol of the copper salt ($CuX_2$) shown in Table 2 below, 18.3 mg (0.03 mmol) of (S)-SEGPHOS and 28.8 mg (0.30 mmol) of NaO-t-Bu, followed by replacing with nitrogen in the autoclave, and then 2 mL of a mixed solvent of toluene and t-BuOH by a ratio of 3:1, and isophorone 1 (0.15 mL, 1.0 mmol) were added. The reaction was carried out with stirring under a hydrogen pressure of 5.0 MPa at 50° C. for 15 to 17 hours. The reaction mixture was analyzed by using GC. The results are shown in Table 2.

Example 17

Homogeneous Asymmetric Hydrogenation of Isophorone 1 Using $[CuBr((S)\text{-SEGPHOS})]_n$ Shown in the Above Scheme A Into a 100-mL stainless-steel autoclave was put 22.6 mmol (0.03 mmol; Cu reduced) of the chiral copper complex $[CuBr((S)\text{-SEGPHOS})]_n$ obtained in the same manner as described in Example 1, 18.3 mg (0.03 mmol) of (S)-SEGPHOS and 28.8 mg (0.30 mmol) of NaO-t-Bu, followed by replacing with nitrogen in the autoclave, and then 2 mL of a mixed solvent of toluene and t-BuOH in a ratio of 3:1, and isophorone 1 (0.15 mL, 1 mmol) were added. The reaction was carried out with stirring under a hydrogen pressure of 5.0 MPa

TABLE 2

| | | | Yield (%) [Optical Purity (% ee)] | | |
|---|---|---|---|---|---|
| Example | $CuX_2$ | Reaction Time (h) | 3,3,5-Trimethylcyclohexanone 2 | 3,3,5-Trimethylcyclohexanol 3 | 3,3,5-Trimethyl-2-cyclohexenol 4 |
| 9 | $CuCl_2$ | 17 | 28[94] | 22[96][b] (93/7)[a] | trace |
| 10 | $Cu(NO_3)_2$ | 15 | 20[95] | 3 | trace |
| 11 | $Cu(OTf)_2$ | 17 | 19[95] | 4 | trace |

[a] dr (Diastereomer ratio)
[b] Optical purity (% ee) of main diastereomer

Examples 12 to 16

Homogeneous Asymmetric Hydrogenation of Isophorone 1 Using $[CuX((S)\text{-SEGPHOS})]_n$ Represented by the Above Scheme A, Shown in the Above Scheme A Into a 100-mL stainless-steel autoclave was put 0.03 mmol (Cu reduced) of the chiral copper complex $[CuX((S)\text{-SEGPHOS})]_n$ obtained in each of Examples 1 to 4 and 28.8 mg (0.30 mmol) of NaO-t-Bu, followed by replacing with nitrogen in the autoclave, and then 2 mL of a mixed solvent of toluene and t-BuOH in a ratio of 3:1, and isophorone 1 (0.15 mL, 1.0 mmol) were added. The reaction was carried out with stirring under a hydrogen pressure of 5.0 MPa at 50° C. The reaction mixture was analyzed by using GC. The results are shown in Table 3.

at 50° C. for 17 hours. The reaction mixture was analyzed by using GC. The results indicated that the products shown in the scheme A, that is, 3,3,5-trimethylcyclohexanone 2 was obtained in a yield of 18% (optical purity 93% ee), 3,3,5-trimethylcyclohexanol 3 was obtained in a yield of 61% (dr: 93/7, optical purity of main diastereomer: 95% ee), and 3,3,5-trimethyl-2-cyclohexenol 4 was obtained in a trace amount, respectively.

Examples 18 and 19

Homogeneous Asymmetric Hydrogenation of Isophorone 1 Using $CuF(PPh_3)_3 \cdot 2EtOH$ Represented by the Above Scheme A, Shown in the Above Scheme A

TABLE 3

| | | | Yield (%) [Optical Purity (% ee)] | | |
|---|---|---|---|---|---|
| Example | X | Reaction Time (h) | 3,3,5-Trimethylcyclohexanone 2 | 3,3,5-Trimethylcyclohexanol 3 | 3,3,5-Trimethyl-2-cyclohexenol 4 |
| 12 | Cl | 17 | 28[90] | 37[92][b] (92/8)[a] | trace |
| 13 | Br | 17 | 27[90] | 43[92][b] (93/7)[a] | trace |
| 14 | Br | 48 | 13[91] | 78[92][b] (92/8)[a] | trace |
| 15 | I | 18 | 18[75] | 3 | trace |
| 16 | OTf | 17 | 21[93] | 6 | trace |

[a] dr (Diastereomer ratio)
[b] Optical purity (% ee) of main diastereomer

Into a 100-mL stainless-steel autoclave was put 28.8 mg (0.03 mmol) of CuF(PPh$_3$)$_3$·2EtOH, 0.03 mmol of chiral ligand and 28.8 mg (0.30 mmol) of NaO-t-Bu, followed by replacing with nitrogen in the autoclave, and then 2 ml of isopropyl alcohol (IPA) and isophorone 1 (0.45 mL, 3.0 mmol) were added. The reaction was carried out with stirring under a hydrogen pressure of 5.0 MPa at 30° C. for 16 hours. The reaction mixture was analyzed by using GC. The results are shown in Table 4.

TABLE 4

| | | Yield (%) [Optical Purity (% ee)] | | |
|---|---|---|---|---|
| Example | Chral Ligand | 3,3,5-Trimethylcyclohexanone 2 | 3,3,5-Trimethylcyclohexanol 3 | 3,3,5-Trimethyl-2-cyclohexenol 4 |
| 18 | (R,R)-SKEWPHOS | trace | 9[24][b) | 83[11] |
| 19 | (S)-SEGPHOS | trace | 14[81][b) | 10[6] |

[b)]Optical purity (% ee) of main diastereomer

Example 20

Homogeneous Asymmetric Hydrogenation of Acetophenone Using [CuBr((S)-SEGPHOS)]$_n$ Into a 20-ml Schrenck tube was put 21.3 mg (0.029 mmol (Cu reduced)) of [CuBr((S)-SEGPHOS)]$_n$ obtained in the same manner as described in Example 1 and 27.8 mg (0.29 mmol) of NaO-t-Bu, followed by replacing with nitrogen in the Schrenck tube, and then 1.4 mL of toluene was added. The reaction was carried out with stirring at room temperature for 1 hour. And then, a separate 100-mL stainless-steel autoclave was set, followed by replacing with nitrogen in the autoclave. Into this autoclave was put 113 µL (0.96 mmol) of acetophenone and 450 µL of t-BuOH, and then the previously prepared content of the Schrenck tube was added to the autoclave. The reaction was carried out with stirring under a hydrogen pressure of 3 MPa at 50° C. for 19 hours. The reaction mixture was analyzed by using GC. The results indicated that 1-phenethyl alcohol, which is a hydrogenated compound of acetophenone, was obtained in a yield of 65.4% and an optical purity of 65.7% ee.

Example 21

Homogeneous Asymmetric Hydrogenation of 2-Acetylfuran Using [CuBr((S)-SEGPHOS)]$_n$ Into a 100-mL stainless-steel autoclave was put 22.6 mg [0.03 mmol (Cu reduced)] of [CuBr((S)-SEGPHOS)]$_n$ obtained in the same manner as described in Example 1 and 28.8 mg (0.30 mmol) of NaO-t-Bu, followed by replacing with nitrogen in the autoclave, and then 1.5 mL of toluene, 500 µL of t-BuOH and 110.1 mg (1.0 mmol) of 2-acetylfuran were added. The reaction was carried out with stirring under a hydrogen pressure of 3.0 MPa at 50° C. for 17 hours. The reaction mixture was analyzed by using GC. The results indicated that 1-(2-furyl)ethanol, which is a hydrogenated compound of 2-acetylfuran, was obtained in a yield of 13% and an optical purity of 59.5% ee.

Example 22

Homogeneous Asymmetric Hydrogenation of Isophorone Using [CuH(PPh$_3$)]$_6$

Into a 100-mL stainless-steel autoclave was put 9.8 mg [0.03 mmol (Cu reduced)] of [CuH(PPh$_3$)]$_6$ and 18.3 mg (0.03 mmol) of (S)-SEGPHOS, followed by replacing with nitrogen in the autoclave, and then 2 ml of a mixed solvent of toluene and t-BuOH in a ratio of 3:1, and 0.15 mL (1.0 mmol) of isophorone, were added. The reaction was carried out with stirring under a hydrogen pressure of 5.0 MPa at 50° C. for 17 hours. The reaction mixture was analyzed by using GC. The results are shown in Table 5.

Example 23

Homogeneous Asymmetric Hydrogenation of Isophorone Using [CuH(PPh$_3$)]$_6$

In Example 22, the reaction was carried out in the same manner as described in Example 22 except for adding 28.8 mg (0.30 mmol) of NaO-t-Bu as a base thereto and changing the reaction time to 18 hours. The reaction mixture was analyzed by using GC. The results are also shown in Table 5.

TABLE 5

| | | Yield (%) [Optical Purity (% ee)] | |
|---|---|---|---|
| Example | Base | 3,3,5-Trimethyl-cyclohexanone 2 | 3,3,5-Trimethyl-cyclohexanol 3 |
| 22 | absent | 8[55] | 1 |
| 23 | present | 15[73] | 3 |

Example 24

Production of Methyl 2-methylbutanoate

Into a 100-mL stainless-steel autoclave was put 114 mg (1 mmol) of methyl tiglate, 22.6 mg [0.03 mmol (Cu reduced)] of [CuBr((S)-SEGPHOS)]$_n$ and 33.6 mg (0.3 mmol) of potassium tert-butoxide ($^t$BuOK), followed by replacing with nitrogen in the autoclave, and then 1.1 mL of a mixed solvent of toluene and t-BuOH in a ratio of 3:1 was added. The reaction was carried out with stirring under a hydrogen pressure of 3.0 MPa at 85° C. for 17 hours to give methyl 2-methylbutanoate, which is a hydrogenated compound of methyl tiglate, in a yield of 63.8%.

Example 25

Production of Methyl 2-methyl 3-phenylpropionate

Into a 100-mL stainless-steel autoclave was put 176 mg (1 mmol) of methyl 2-methyl-3-phenylpropenate, 22.6 mg (0.03 mmol (equivalent in Cu)) of [CuBr((S)-SEGPHOS)]$_n$ and 33.6 mg (0.3 mmol) of $^t$BuOK were introduced in to a 100- mL stainless-steel autoclave, followed by replacing with nitrogen in the autoclave, and then 1.8 mL of a mixed solvent of toluene and t-BuOH in a ratio of 3:1 was added. The reaction was carried out with stirring under a hydrogen pressure of 3.0 MPa at 85° C. for 17 hours to give methyl 2-methyl 3-phenylpropionate, which is a hydrogenated compound of methyl 2-methyl-3-phenylpropenate, in a yield of 54.7%.

Example 26

Production of Methyl 2-acetamidopropionate

Into a 100-mL stainless-steel autoclave was put 143 mg (1 mmol) of methyl 2-acetamido-2-propenate, 22.6 mg [0.03 mmol (Cu reduced)] of [CuBr((S)-SEGPHOS)]$_n$ and 33.6 mg (0.3 mmol) of $^t$BuOK, followed by replacing with nitrogen in the autoclave, and then 1.4 mL of a mixed solvent of toluene and t-BuOH in a ratio of 3:1 was added. The reaction was carried out with stirring under a hydrogen pressure of 3.0 MPa at 85° C. for 17 hours to give methyl 2-acetamidopropionate, which is a hydrogenated compound of methyl 2-acetamido-2-propenate in a yield of 52.5%.

Example 27

Synthesis of [CuCl((R,R)-SKEWPHOS)(PPh$_3$)]$_n$

Into a 20-ml Schrenck tube was put 131 mg (0.5 mmol) of triphenyl phosphine was introduced into a 20-ml Schrenck tube previously flushed with nitrogen, and then 1 mL of toluene was added to it to form a homogeneous solution. 49.5 mg (0.5 mmol) of CuCl and 5 mL of toluene were added to the solution and stirred at room temperature for 3 hours. Then, 220 mg (0.5 mmol) of (R,R)-SKEWPHOS was added thereto and stirred for 30 minutes, and then 2.5 mL of toluene was further added, and the mixture was stirred at room temperature for 3 hours. The resulting white suspension was filtered and solids were washed with toluene, whereby 320 mg of the objective title compound (yield 80%) was obtained as a white solid.

$^{31}$P-NMR (CDCl$_3$): δ; −10.0 (br, 1P), 2.3 (br, 2P)
EI-MS: 765.3[(M-Cl)+]
ESI-MS: 765.2[(M-Cl)+]

Examples 28 to 30

Homogeneous Asymmetric Hydrogenation of Acetophenone Using [CuCl ((R,R)-SKEWPHOS) (PPh$_3$)]$_n$ Into a 100-mL stainless-steel autoclave was put 24.0 mg (0.03 mmol) of [CuCl((R,R)-SKEWPHOS) (PPh$_3$)]$_n$ obtained in Example 27, triphenyl phosphine of the amount shown in Table 6 below, and 28.8 mg (0.30 mmol) of NaO-t-Bu, followed by replacing with nitrogen in the autoclave, and then 2.0 mL of isopropyl alcohol and 1.05 mL (9.0 mmol) of acetophenone were added. The reaction was carried out with stirring under a hydrogen pressure of 5 MPa at 30° C. for 16 to 17 hours to give 1-phenethyl alcohol which is a hydrogenated compound of acetophenone. The reaction mixture was analyzed by using GC. The results are shown in Table 6.

TABLE 6

| Example | Amount (equivalent) of triphenylphosphine used relative to 1 equivalent of Cu | 1-Phenethyl alcohol Yield (%) | Optical Purity (% ee) |
|---|---|---|---|
| 28 | 0 | 55 | 44 |
| 29 | 1 | 94 | 47 |
| 30 | 2 | 97 | 47 |

Examples 31 to 40

Homogeneous Asymmetric Hydrogenation of Acetophenone (Addition of a Base)

Into a 100-mL stainless-steel autoclave was put a copper compound [0.03 mmol (Cu reduced)], 13.2 mg (0.03 mmol) of (R,R)-SKEWPHOS and 28.8 mg (0.30 mmol) of NaO-t-Bu, followed by replacing with nitrogen in the autoclave, and then 2.0 mL of solvent and 1.05 mL (9.0 mmol) of acetophenone were added thereto. The reaction was carried out with stirring under a prescribed hydrogen pressure at a prescribed temperature for 16 to 17 hours. Table 7 shows the copper compound, the solvent, the hydrogen pressure and the reaction temperature used in the reaction, and the yield and optical purity of 1-phenethylalcohol which is a hydrogenated compound of acetophenone, as analyzed by using GC of the reaction mixture.

TABLE 7

| Example | Copper Compound | Solvent | Hydrogen Pressure (MPa) | Temperature (° C.) | Yield (%) | Optical Purity (% ee) |
|---|---|---|---|---|---|---|
| 31 | [CuCl(R,R)•SKEWPHOS]$_n$ | t-BuOH | 3.0 | 50 | >99 | 46 |
| 32 | CuF(PPh$_3$)$_3$•2EtOH | t-BuOH | 3.0 | 30 | >99 | 53 |
| 33 | CuF(PPh$_3$)$_3$•2EtOH | EtOH | 5.0 | 30 | >99 | 41 |
| 34 | CuF(PPh$_3$)$_3$•2EtOH | IPA | 3.0 | 30 | >99 | 47 |
| 35 | CuF(PPh$_3$)$_3$•2EtOH | t-Bu(Me)CHOH | 5.0 | 30 | >99 | 56 |
| 36 | CuF(PPh$_3$)$_3$•2EtOH | (R)-t-Bu(Me)CHOH | 5.0 | 30 | >99 | 55 |
| 37 | CuF(PPh$_3$)$_3$•2EtOH | CPME | 5.0 | 30 | >99 | 55 |
| 38 | CuCl(PPh$_3$)$_3$ | IPA | 3.0 | 30 | >99 | 47 |
| 39 | CuCl(P(m-tol)$_3$)$_3$ | CPME | 5.0 | 30 | 94 | 62 |
| 40 | Cu(NO$_3$)(PPh$_3$)$_2$ | IPA | 5.0 | 50 | >99 | 43 | t-BuOH: tert-butyl alcohol
EtOH: ethyl alcohol
IPA: isopropyl alcohol
t-Bu(Me)CHOH: 3,3-dimethylbutan-2-ol
(R)-t-Bu(Me)CHOH: (R)-3,3-dimethylbutan-2-ol
CPME: cyclopentyl methyl ether
tol: —C$_6$H$_4$CH$_3$

Examples 41 to 46

Homogeneous Asymmetric Hydrogenation of Acetophenone

Into a 100-mL stainless-steel autoclave was put 0.03 mmol of the copper halide (CuX), triphenyl phosphine (PPh$_3$), and (R,R)-SKEWPHOS shown in Table 8 below, respectively, and 28.8 mg (0.30 mmol) of NaO-t-Bu, followed by replacing with nitrogen in the autoclave, and then 2.0 mL of IPA and 1.05 mL (9.0 mmol) of acetophenone were added thereto. The reaction was carried out with stirring under a hydrogen pressure of 5.0 MPa at 30° C. for 16 to 17 hours. Table 8 shows the copper halide (CuX) used, the amount of (R,R)-SKEWPHOS used, the amount of triphenyl phosphine used, and the yield and optical purity of 1-phenethyl alcohol which is a hydrogenated compound of acetophenone, as analyzed by using GC analysis of the reaction mixture.

TABLE 8

| Example | CuX | Used amount (equivalent) of (R,R)-SKEWPHOS relative to CuX | Used amount (equivalent) of triphenyl phosphine relative to CuX | Yield (%) | Optical Purity (% ee) |
|---|---|---|---|---|---|
| 41 | CuI | 1 | 1 | 7 | 31 |
| 42 | CuBr | 1 | 1 | 12 | 43 |
| 43 | CuCl | 1 | 1 | 50 | 46 |
| 44 | CuCl | 1 | 2 | >99 | 47 |
| 45 | CuCl | 1 | 3 | >99 | 47 |
| 46 | CuCl | 2 | 0 | 53 | 45 |

Examples 47 to 60

Homogeneous Asymmetric Hydrogenation of Acetophenone

Into a 100-mL stainless-steel autoclave was put 3.0 mg (0.03 mmol) of CuCl, 0.09 mmol of ligand, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 1.05 mL (9.0 mmol) of acetophenone were added thereto. The reaction was carried out with stirring under a hydrogen pressure of 5.0 MPa at 30° C. for 16 to 17 hours. Table 9 shows the ligand used, and the yield and optical purity of 1-phenethyl alcohol which is a hydrogenated compound of acetophenone, as analyzed by using GC of the reaction mixture.

TABLE 9

| Example | Ligand | Yield (%) | Optical Purity (% ee) |
|---|---|---|---|
| 47 | PCy$_3$ | 25 | 35 |
| 48 | P(t-Bu)$_3$ | 16 | 47 |
| 49 | P(OPh)$_3$ | 3 | 37 |
| 50 | P(2-furyl)$_3$ | 7 | 47 |
| 51 | P(C$_6$F$_5$)$_3$ | 7 | 38 |
| 52 | PPh$_2$(2-naphthyl) | >99 | 50 |
| 53 | P(1-naphtyl)$_3$ | 32 | 20 |
| 54 | P(2-naphthy)$_3$ | 80 | 50 |
| 55 | P(o-tolyl)$_3$ | 29 | 40 |
| 56 | P(m-tolyl)$_3$ | 97 | 53 |
| 57 | P(p-tolyl)$_3$ | >99 | 50 |
| 58 | P(4-t-Bu-C$_6$H$_4$)$_3$ | 58 | 46 |
| 59 | P(3,5-xylyl)$_3$ | >99 | 57 |
| 60 | P(3,5-di-t-Bu-C$_6$H$_3$)$_3$ | 34 | 34 |

Examples 61 and 62

Homogeneous Asymmetric Hydrogenation of Acetophenone (Addition 5 of a Base)

Into a 100-mL stainless-steel autoclave was put 28.8 mg [0.03 mmol/Cu (Cu reduced)] of CuF(PPh$_3$)$_3$.2EtOH, 39.6 mg (0.09 mmol) of (R,R)-SKEWPHOS and 28.8 mg (0.30 mmol) of NaO-t-Bu, followed by replacing with nitrogen in the autoclave, and then 7.0 mL of solvent and 3.5 mL (30 mmol) of acetophenone were added thereto. The reaction was carried out with stirring under a hydrogen pressure of 5.0 MPa at 50° C. for 24 hours. Table 10 shows the solvent used, and the yield and optical purity of 1-phenethyl alcohol which is a hydrogenated compound of acetophenone, as analyzed by using GC of the reaction mixture.

TABLE 10

| Example | Solvent | Yield (%) | Optical Purity (% ee) |
|---|---|---|---|
| 61 | IPA | >99 | 43 |
| 62 | t-BuOH | >99 | 48 |

Example 63

Homogeneous Asymmetric Hydrogenation of Acetophenone (Silylenol Ether Addition)

Into a 100-mL stainless-steel autoclave was put 28.8 mg (0.03 mmol/Cu) of CuF(PPh$_3$)$_3$.2EtOH, 13.2 mg (0.03 mmol) of (R,R)-SKEWPHOS and 61.5 μL (0.30 mmol) of 1-phenyl-1-(trimethylsiloxy)ethylene, followed by replacing with nitrogen in the autoclave, and then 2.0 mL of t-BuOH and 1.05 mL (9.0 mmol) of acetophenone were added thereto. The reaction was carried out with stirring under a hydrogen pressure of 3.0 MPa at 50° C. for 16 hours. The reaction mixture was analyzed by using GC. The results revealed that 1-phenethyl alcohol, which is a hydrogenated compound of acetophenone, was obtained in a yield of 24% and in an optical purity of 50% ee.

Examples 64 and 65

Homogeneous Asymmetric Hydrogenation of Acetophenone Using [CuH(PPh$_3$)]$_6$

Into a 100-mL stainless-steel autoclave was put 9.8 mg (0.03 mmol (equivalent in Cu)) of [CuH(PPh$_3$)]$_6$, 13.2 mg (0.03 mmol) of (R,R)-SKEWPHOS and 28.8 mg (0.30 mmol) of NaO-t-Bu, followed by replacing with nitrogen in the autoclave, and then 2.0 mL of solvent and 1.05 mL (9.0 mmol) of acetophenone were added thereto. The reaction was carried out with stirring under a hydrogen pressure of 3.0 MPa at 30° C. for 16 hours. Table 11 shows the solvent used, and the yield and optical purity of 1-phenethyl alcohol which is a hydrogenated compound of acetophenone, as analyzed by using GC of the reaction mixture.

TABLE 11

| Example | Solvent | Yield (%) | Optical Purity (% ee) |
|---|---|---|---|
| 64 | IPA | >99 | 49 |
| 65 | toluene | 79 | 56 |

Examples 66 to 68

Homogeneous Asymmetric Hydrogenation of Substituted Acetophenone

Into a 100-mL stainless-steel autoclave was put 28.8 mg (0.03 mmol) of CuF(PPh$_3$)$_3$.2EtOH, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 9.0 mmol of substituted acetophenone were added thereto. The reaction was carried out with stirring under a hydrogen pressure of 5.0 MPa at 30° C. for 16 hours. Table 12 shows the substituted acetophenone used, and the yield and optical purity of a hydrogenated compound of substituted acetophenone, as analyzed by using GC of the reaction mixture.

TABLE 12

| Example | Substituted Acetophenone | Yield (%) | Optical Purity (% ee) |
|---|---|---|---|
| 66 | 4'-Bromoasetophenone | >99 | 48 |
| 67 | 2'-mrthylacetophenone | 89 | 60 |
| 68 | 3',5'-bis(trifluoromethyl)acetophenone | >99 | 5 |

Examples 69 to 79

Homogeneous Asymmetric Hydrogenation of Substituted Acetophenone

Into a 100-mL stainless-steel autoclave was put 3.0 mg (0.03 mmol) of CuCl, 31.1 mg (0.09 mmol) of tris(3,5-dimethylphenyl)phosphine, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 1.05 mL (9.0 mmol) of substituted acetophenone were added thereto. The reaction was carried out with stirring under a hydrogen pressure of 5 MPa at 30° C. for 16 to 17 hours. Table 13 shows the substituted acetophenone used, and the yield and optical purity of a hydrogenated compound of substituted acetophenone, as analyzed by using GC of the reaction mixture.

TABLE 13

| Example | Substituted Acetophenone | Yield (%) | Optical Purity (% ee) |
|---|---|---|---|
| 69 | 2'-Methylacetophenone | 87 | 86 |
| 70 (Note 1) | 2'-Methylacetophenone | 95 | 86 |
| 71 (Note 2) | 2'-Methylacetophenone | 23 | 90 |
| 72 | 2'-Bromoacetophenone | 19 | 74 |
| 73 | 2'-Trifluoromethylacetophenone | 47 | 89 |
| 74 | 2'-Methoxyacetophenone | 58 | 84 |
| 75 | 2'-Aminoacetophenone | 26 | 83 |
| 76 | 1-Acetonaphthone | 82 | 64 |
| 77 | 3'-Methylacetophenone | >99 | 63 |
| 78 | 3'-Bromoacetophenone | 48 | 44 |
| 79 | 4'-Methylacetophenone | 93 | 57 |

Note 1:
0.25 mmol of tris(3,5-dimethylphenyl)phosphine was used.
Note 2:
2,4-dimethyl-3-pentanol was used as solvent.

Examples 80

Homogeneous Asymmetric Hydrogenation of Pinacolin

Into a 100-mL stainless-steel autoclave was put 28.8 mg (0.03 mmol (equivalent in Cu)) of CuF(PPh$_3$) 32EtOH, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 1.13 mL (9.0 mmol) of pinacolin were added thereto. The reaction was carried out with stirring under a hydrogen pressure of 5.0 MPa at 30° C. for 16 hours. The reaction mixture was analyzed by using GC. The results revealed that 3,3-dimethylbutan-2-ol, which is a hydrogenated compound of pinacolin, was obtained in a yield of 79% and in an optical purity of 17% ee.

Examples 81

Homogeneous Asymmetric Hydrogenation of 2-acetylfuran

Into a 100-mL stainless-steel autoclave was put 28.8 mg (0.03 mmol (equivalent in Cu)) of CuF(PPh$_3$)$_3$.2EtOH, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 0.90 mL (9.0 mmol) of 2-acetylfuran were added thereto. The reaction was carried out with stirring under a hydrogen pressure of 5.0 MPa at 30° C. for 16 hours. The reaction mixture was analyzed by using GC. The results indicated that 1-(2-furyl)ethanol, which is a hydrogenated compound of 2-acetylfuran, was obtained in a yield of 99% and in an optical purity of 31% ee.

Examples 82

Homogeneous Asymmetric Hydrogenation of 2,3,3-trimethylindolenine

Into a 100-mL stainless-steel autoclave was put 26.5 mg (0.03 mmol) of CuCl(PPh$_3$)$_3$, 13.2 mg (0.03 mmol) of (R,R)-SKEWPHOS and 28.8 mg (0.30 mmol) of NaO-t-Bu, followed by replacing with nitrogen in the autoclave, and then 2.0 mL of IPA and 161 μL (1.0 mmol) of 2,3,3-trimethylindolenine were added thereto. The reaction was carried out with stirring under a hydrogen pressure of 5.0 MPa at 30° C. for 16 hours. The reaction mixture was analyzed by using GC. The results revealed that 2,3,3-trimethyl-2,3-dihydro-1H-indole, which is a hydrogenated compound of 2,3,3-trimethylindolene, was obtained in a yield of 7% and in an optical purity of 57% ee.

Examples 83 to 96

Homogeneous Asymmetric Hydrogenation of Acetophenone

Into a 100-mL stainless-steel autoclave was put 11.7 mg (0.018 mmol (equivalent in Cu)) of Cu(NO$_3$)$_2$(PPh$_3$)$_2$ and a chiral ligand (0.018 mmol), followed by replacing with nitrogen in the autoclave, and then 2.0 mL (0.18 mmol) of 0.09 M NaO-t-Bu IPA solution and 1.05 mL (9.0 mmol) of acetophenone were added thereto. The reaction was carried out with stirring under a hydrogen pressure of 5.0 MPa at 30° C. for 16 to 17 hours. The reaction mixture was analyzed by using GC. Table 14 shows the chiral ligand used, and the yield and optical purity of 1-phenethyl alcohol which is a hydrogenated compound of acetophenone.

TABLE 14

| Example | Chiral Ligand | Yield (%) | Optical Purity (% ee) |
|---|---|---|---|
| 83 | (S,S)-SKEWPHOS | >99 | 47 |
| 84 | (−)-DIOP | >99 | 12 |
| 85 | (S,S)-BPPM | >99 | 27 |
| 86 | (S,S)-BCPM | 18 | 13 |
| 87 | (R)-BINAP | 17 | 24 |
| 88 | (S)-H$_8$-BINAP | 10 | 17 |
| 89 | (S)-SEGPHOS | 73 | 11 |
| 90 | (R)-DM-SEGPHOS | 5 | 24 |
| 91 | (−)-DTBM-SEGPHOS | 22 | 72 |
| 92 | (R)-Xylyl-P-PHOS | 16 | 25 |
| 93 | (R,S)-Josiphos | 99 | 45 |
| 94 | (R,R)-Me-DuPHOS | 12 | 4 |
| 95 | (+)-IPR-BeePHOS | 9 | 13 |
| 96 | (S,S)-CHIRAPHOS | 2 | 14 |

BPPM: N-tert-butoxycarbonyl-4-diphenylphosphino-2-diphenyl phosphinomethyl pyrrolidine;
BCPM: N-tert-butoxycarbonyl-4-dicyclohexylphosphino-2-diphenyl phosphinomethyl pyrrolidine;
Xylyl-P-PHOS: 2,2',6,6'-tetramethoxy-4,4'-bis(di(3,5-xylyl)phosphino)-3,3'-bipyridine
Josiphos: [2-(diphenylphoshino)ferrocenyl]ethyldicyclohexylphosphine;
Me-DuPHOS: 1,2-bis(2,5-dimethylphospholano) benzene;
IPR-BeePHOS: 1,2-bis(2-isopropyl-2,3-dihydro-1H-phosphoindol-1-yl)benzene Example 97

Homogeneous Asymmetric Hydrogenation of Acetophenone

Into a 100-mL stainless-steel autoclave was put 5.9 mg (0.018 mmol (equivalent in Cu)) of [CuH(PPh$_3$)$_3$]$_6$ and 7.9 mg (0.018 mmol) of (S,S)-SKEWPHOS, followed by replacing with nitrogen in the autoclave, and then 2.0 mL of IPA and 1.05 mL (9 mmol) of acetophenone were added thereto. The reaction was carried out with stirring under a hydrogen pressure of 5.0 MPa at 30° C. for 16 hours. The reaction mixture was analyzed by using GC. The results revealed that 1-phenethyl alcohol, which is a hydrogenated compound of acetophenone, was obtained in a yield of 67% and in an optical purity of 47% ee.

Example 98

Homogeneous Asymmetric Hydrogenation of Acetophenone

Into a 100-mL stainless-steel autoclave was put 5.9 mg (0.018 mmol (equivalent in Cu)) of [CuH(PPh$_3$)$_3$]$_6$, 4.7 mg (0.018 mmol) of triphenyl phosphine and 7.9 mg (0.018 mmol) of (S,S)-SKEWPHOS, followed by replacing with nitrogen in the autoclave, and then 2.0 mL of IPA and 1.05 mL (9 mmol) of acetophenone were added thereto. The reaction was carried out with stirring under a hydrogen pressure of 5.0 MPa at 30° C. for 16 hours. The reaction mixture was analyzed by using GC. The results revealed that 1-phenethyl alcohol, which is a hydrogenated compound of acetophenone, was obtained in a yield of 99% and in an optical purity of 47% ee.

INDUSTRIAL APPLICABILITY

The catalyst for homogeneous hydrogenation according to the present invention is useful in hydrogenation carried out in a homogeneous system, and particularly when the asymmetric hydrogenation of an unsaturated compound is carried out with this catalyst as a catalyst for homogeneous asymmetric hydrogenation, a desired optically active compound can be produced not only in high yield and high optical purity but also with high economical efficiency and workability.

What is claimed is:

1. A chiral copper complex represented by the formula (61):

$$[L^{11}L^{12}CuL^{13}]_{n35} \qquad (61)$$

wherein $L^{11}$ represents a bidentate optically active phosphorus compound represented by the following formula (10):

$$R^6R^7P\text{-}Q^3\text{-}PR^8R^9 \qquad (10)$$

wherein $R^6$ to $R^9$ independently represent an optionally substituted hydrocarbon group having 1-20 carbon atoms, an optionally substituted 3- to 8-membered heterocyclic group having 2-14 carbon atoms and 1-3 heteroatoms selected from the group consisting of a nitrogen atom, an oxygen atom and a sulfur atom, an optionally substituted alkoxy group, an optionally substituted aryloxy group, or an optionally substituted aralkyloxy group; $Q^3$ represents a spacer; and $R^6$ and $R^7$ and P and/or $R^8$ and $R^9$ and P or $R^6$ and/or $R^7$ and $Q^3$ or $R^8$ and/or $R^9$ and $Q^3$ may be combined to form a ring, provided that $R^6$ to $R^9$ and $Q^3$ may be such a group that the phosphorus compound represented by the formula (10) is capable of forming the optically active phosphorus compound; $L^{12}$ represents a phosphorus compound represented by the formula (41):

$$PR^{151}_3 \qquad (41)$$

wherein three $R^{151}$s are the same or different and represent a hydrogen atom, an optionally substituted hydrocarbon group, an optionally substituted heterocyclic group, an optionally substituted alkoxy group, an optionally substituted aryloxy group, an optionally substituted aralkyloxy group, an amino group or a substituted amino group;

$L^{13}$ represents a ligand; and n35 represents a natural number, wherein, when the hydrocarbon, heterocyclic group, alkoxy group, aryloxy group, aralkyloxy group, or amino group is substituted, the substituent is selected from the group consisting of an alkyl group having 1 to 20 atoms, an alkenyl group having 2 to 20 carbon atoms, an alkynyl group having 2 to 20 carbon atoms, an alkadienyl group having 4 to 20 carbon atoms, an aryl group having 6 to 20 carbon atoms, an aralkyl group having 7 to 20 carbon atoms, an aliphatic heterocyclic group having 2 to 14 carbon atoms, an aromatic heterocyclic group having 2 to 15 carbon atoms, fluorine, chlorine, bromine, iodine, an halogenated alkyl group having 1 to 20 carbon atoms, an alkoxy group having 1 to 20 carbon atoms, an aryloxy group having 6 to 20 carbon atoms, an aralkyloxy group having 7 to 20 carbon atoms, a heteroaryloxy group having 2 to 20 carbon atoms, an alkylthio group having 1 to 20 carbon atoms, an arylthio group having 6 to 20 carbon atoms, an aralkylthio group having 7 to 20 carbon atoms, an heteroarylthio group having 2 to 20 carbon atoms, an acyl group having 1 to 20 carbon atoms, an acyloxy group having 2 to 20 atoms, an alkoxycarbonyl group having 2 to 20 carbon atoms, an aryloxycarbonyl group having 7 to 20 carbon atoms, an aralkyloxycarbonyl group having 8 to 20 carbon atoms, an alkylene group having 1 to 6 carbon atoms, an alkylenedioxy group having 2 to 20 carbon atoms, a nitro group, an amino group, a cyano group, sulfo group, a hydroxyl group, a carboxy group, an alkoxythiocarbonyl group having 2 to 20 carbon atoms, an aryloxythiocarbonyl group having 7 to 20 carbon atoms, an aralkyloxythiocarbonyl group having 8 to 20 carbon atoms, an alkylthiocarbonyl group having 2 to 20 carbon atoms, an arylthiocarbonyl group having 7 to 20 carbon atoms, an aralkyloxythiocarbonyl group having 8 to 20 carbon atoms, a carbamoyl group, a phosphino group and an oxo group.

2. A catalyst comprising the chiral copper complex according to claim 1.

3. The catalyst according to claim 2, which is a catalyst for homogeneous asymmetric hydrogenation.

4. A process for producing an optically active compound, which comprises subjecting a prochiral compound to a homogeneous asymmetric hydrogenation in the presence of the catalyst for homogeneous asymmetric hydrogenation as claimed in claim 3.

5. A homogeneous hydrogenation method comprising subjecting an unsaturated compound to a hydrogenation in the presence of the catalyst of claim 2 to produce a hydrogenated product of the unsaturated compound.

6. A homogeneous asymmetric hydrogenation method comprising subjecting an unsaturated compound to a hydrogenation in the presence of the catalyst of claim 3 to produce an optically active hydrogenated product.

7. The chiral copper complex according to claim 1, wherein the bidentate optically active phosphorus compound represented by the formula (10) is selected from the group consisting of 1,2-bis(anisylphenylphosphino)ethane, 1,2-bis(alkylmethylphosphino)ethane, 2,3-bis(diphenylphosphino)butane, 1,2-bis(diphenylphosphino)propane, 2,3-bis(diphenylphosphino)-5-norbornene, 2,3-0-isopropylidene-2,3-dihydroxy-1,4-bis(diphenylphosphino)butane, 1-cyclohexyl-1,2-bis(diphenylphosphino)ethane, 1-substituted-3,4-bis(diphenylphosphino)pyrrolidine, 2,4-bis(diphenylphosphino)pentane, 1,2-bis(substituted phospholano)benzene, 1,2-bis(substituted phospholano)ethane, 1-(substituted phospholano)-2-(diphenylphosphino)benzene, 1-(bis(3,5-dimethylphenyl)phosphino)-2-(substituted phospholano)benzene, 1-(substituted phospholano)-2-(bis(3,5-di(tert-butyl)-4-methoxyphenyl)phosphino)benzene, 1-(substituted phospholano)-2-(di-naphthalen-1-yl-phosphino)benzene, 2,2'-bis(diphenylphosphino)-1,1'-bicylopentane, 2,2'-bis(diphenylphosphino)-1,1'-binaphthyl, 2,2'-bis(diphenylphosphino)-1,1'-(5,5',6,6',7,7',8,8'-octahydronaphthyl), 2,2'-bis(d i-p-tolylphosphino)-1,1'-binaphthyl,2,2'-bis(di(3,5-dimethylphenyl)phosphino)-1,1'-binaphthyl, 2,2'-bis(diphenylphosphino)-6,6'-dimethyl-1,1'-biphenyl, (4,4'-bi-1,3-benzodioxol)-5,51-diylbis(diphenylphosphine), (4,4'-bi-1,3-benzodioxol) -5,5'-diylbisfbis(3,5-dimethylphenyl)phosphinel, and (4S)-4,4'-bi-1,3-benzodioxo1]-5,5'-diyllbis[bis[3,5-bis(1,1-dimethylethyl)-4-methoxyphenyliphosphine.

8. The chiral copper complex according to claim 1, wherein the phosphorus compound represented by the formula (41) is selected from the group consisting of triphenylphosphine, tritolyiphosphine, trimethylphosphine, triethylphosphine, methyl diphenylphosphine, dimethyl phenyiphosphine, diphenylphosphinomethane, diphenylphosphinoethane, diphenylphosphinopropane, diphenylphosphinobutane, diphenylphosphinoferrocene, trimethyl phosphite, triethyl phosphate, and triphenyl phosphate.

9. The chiral copper complex according to claim 1, wherein $L^{13}$ is selected from the group consisting of a nitrate ion, a nitrite ion, a halide ion, a sulfate ion, a sulfite ion, a sulfonate ion, a sulfamate ion, a carbonate ion, a hydroxide ion, a carboxylate ion, a sulfide ion, a thiocyanate ion, a phosphate ion, a pyrophosphate ion, an oxide ion, a phosphide ion, a chlorate ion, a perchlorate ion, an iodate ion, a hexafluorosilicate ion, a cyanide ion, a borate ion, a metaborate ion, a hydrido ion and a borofluoride ion.

10. The chiral copper complex according to claim 1, which is selected from the group consisting of $[CuF(PPh_3)(L^{20})]_n$, $[CuCl(PPh_3)(L^{20})]_n$, $[CuBr(PPh_3)(L^{20})]_n$, $[CuI(PPh_3)(L^{20})]_n$, $[CuH(PPh_3)(L^{20})]_n$, $[CuOTf(PPh_3)(L^{20})]_n$, $[Cu(NO_3)(PPh_3)(L^{20})]_n$, $[Cu(OAc)(PPh_3)(L^{20})]_n$ and $[CuCl(P(3,5-xylyl)_3)(L^{20})]_n$, wherein $L^{20}$ represents ((R)-2,2'-bis(diphenylphosphino)-1,1'-binaphthyl, (S)-2,2'-bis(diphenylphosphino)-1,1'-binaphthyl, (R)-2,2'-bis(di(3,5-dimethylphenyl)phosphino)-1,1'-binaphthyl, (S)-2,2'-bis(di(3,5-dimethylphenyl)phosphino)-1,1'-binaphthyl, (R)-(4,4'-bi-1,3-benzodioxol)-5,5'-diylbis(diphenylphosphine), (S)-(4,4'-bi-1,3-benzodioxol)-5,5'-diylbis(diphenylphosphine), (R)-(4,4'-bi-1,3-benzodioxol)-5,5'-diylbis[bis(3,5-dimethylphenyl)phosphine], (S)-(4,4'-bi-1,3-benzodioxol)-5,5'-diylbis[bis(3,5-dimethylphenyl)phosphine], [(4R)-[4,4'-bi-1,3-benzodioxol]-5,5'-diyl]bis[bis[3,5-bis(1,1-dimethylethyl)-4-methoxyphenyl]phosphine], [(4S)-[4,4'-bi-1,3-benzodioxol]-5,5'-diyl]bis[bis[3,5-bis(1,1-dimethylethyl)-4-methoxyphenyl]phosphine], (2R,4R)- 2,4-bis -(diphenylphosphino)pentane, 1,2-bis((2S,5S)-2,5-dimethylphospholano)benzene, (R)-1-[(S)-2-(diphenylphosphino)ferrocenyl]ethyldicyclohexylphosphine, or (S)-1-[(R)-2-(diphenylphosphino)ferrocenyl]ethyldicyclohexylphosphine); and n represents a natural number.

11. A process for producing an optically active compound, which comprises subjecting a prochiral compound to a homogeneous asymmetric hydrogenation in the presence of the catalyst for homogeneous hydrogenation as claimed in claim 2.

* * * * *